(12) United States Patent
Ognyanov et al.

(10) Patent No.: US 6,191,165 B1
(45) Date of Patent: *Feb. 20, 2001

(54) PHARMACEUTICAL FOR TREATMENT OF NEUROLOGICAL AND NEUROPSYCHIATRIC DISORDERS

(75) Inventors: Vassil Iliya Ognyanov, Franklin Park; Laurence A. Borden, Hackensack, both of NJ (US); Stanley Charles Bell, Narberth, PA (US); Jing Zhang, Parsippany, NJ (US)

(73) Assignee: Allelix Neuroscience Inc.

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/866,007

(22) Filed: May 30, 1997

Related U.S. Application Data

(63) Continuation-in-part of application No. 08/656,063, filed on May 31, 1996, now abandoned, and a continuation-in-part of application No. 08/655,912, filed on May 31, 1996, now abandoned, and a continuation-in-part of application No. 08/808,755, filed on Feb. 27, 1997, and a continuation-in-part of application No. 08/808,754, filed on Feb. 27, 1997, now abandoned.

(60) Provisional application No. 60/041,503, filed on May 31, 1996, provisional application No. 60/044,387, filed on Feb. 27, 1997, provisional application No. 60/041,504, filed on May 31, 1996, and provisional application No. 60/070,900, filed on Feb. 27, 1997.

(51) Int. Cl.[7] ................ A61K 31/24; A61K 31/275; C07C 211/00; C07C 255/00

(52) U.S. Cl. ................ 514/523; 514/114; 514/538; 514/539; 514/561; 514/576; 514/620; 558/166; 558/390; 560/12; 560/13; 560/17; 560/21; 562/16; 564/164; 564/165; 564/306; 564/316; 564/317; 564/319; 564/320; 564/322

(58) Field of Search ................ 558/166, 390; 560/12, 13, 17, 21; 562/16; 564/164, 165, 306, 316, 317, 319, 320, 322; 514/114, 523, 538, 539, 561, 576, 620

(56) References Cited

U.S. PATENT DOCUMENTS

| | | | |
|---|---|---|---|
| 3,929,813 | 12/1975 | Higuchi et al. | 260/296 M |
| 4,383,999 | 5/1983 | Bondinell et al. | 424/266 |
| 4,514,414 | 4/1985 | Bondinell et al. | 514/422 |
| 4,639,468 | 1/1987 | Roncucci et al. | 514/620 |
| 4,772,615 | 9/1988 | Pavia | 514/318 |
| 4,931,450 | 6/1990 | Sonnewald | 514/326 |
| 5,010,090 | 4/1991 | Gronvald et al. | 514/326 |
| 5,837,730 | 11/1998 | Javitt | 514/551 |

FOREIGN PATENT DOCUMENTS

| | | |
|---|---|---|
| 885 303 | * 3/1981 | (BE). |
| 2144475 | 3/1995 | (CA). |
| 30 10 599 | * 10/1980 | (DE). |
| 0 666 456 A1 | 12/1982 | (EP). |
| 0 068 544 A2 | 1/1983 | (EP). |
| 0 221 572 A2 | 5/1987 | (EP). |
| 0 231 996 A2 | 8/1987 | (EP). |
| 0 672 661 A1 | 9/1995 | (EP). |
| 672 677 | * 9/1995 | (EP). |
| 02129158 | * 5/1990 | (JP). |
| WO 95/04072 | 2/1995 | (WO). |

OTHER PUBLICATIONS

Grant & Hackh's Chemical Dictionary, pp. 366, 408, 415, 416 and 587, 1987.*

Cecil et al., Textbook of Medicine, pp. 1992–1994, 1996.*

Lewis et al., Photochemical Addition of Tertiary Amines to Stilbene. Free–Radical and Electron–Transfer Mechanisms for Amine Oxidation, Journal of the American Chemical Society, vol. 104, No. 7, pp. 1924–1929, Apr. 1982.*

Beal, M. F., Aging, Energy, and Oxidative Stress in Neuro-degenerative Diseases, Annals of Neurology, vol. 38, No. 3, pp. 357–366, Sep. 1995.*

Edlung, P. O., Identification of Amperozide Metabolites in Urine from Rats, Rabbits, Dogs and Man by Frit–FAB LC/MS Using Deuterated Solvents to Gain Additional Structural Information, Journal of Mass Spectrometry, vol. 30, pp. 1380–1392, 1995.*

Inayama et al., A Rapid and Simple Screening Method for Methamphetamine in Urine by Radioimmunoassay using a I–Labeled Methamphetamine Derivative, Chemical & Pharmaceutical Bulletin, vol. 28, No. 9, pp. 2779–2782, Sep., 1980.*

Lehmann, J., Synthese Dihydroxylierter Diphenylalky-lamine Uber Azalactone, Archiv der Pharmazie, vo.. 316, No. 4, pp. 339–346, Apr. 1983.*

Reyna J. Simon et al., *Proc. Natl. Acad. Sci.* USA, 89:9367–9371 (1992).

Fadia E. Ali et al., *J. Med. Chem.*, 28:653–660 (1985).

Michael R. Pavia et al., *J. Med. Chem.*, 35:4238–4248 (1992).

(List continued on next page.)

*Primary Examiner*—Richard L. Raymond
*Assistant Examiner*—Brenda Coleman
(74) *Attorney, Agent, or Firm*—Dechert

(57) ABSTRACT

The invention provides a pharmaceutical for treatment of neurological and neuropsychiatric disorders comprising a compound of the formula:

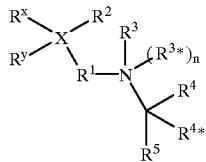

or a pharmaceutically acceptable salt thereof.

28 Claims, 4 Drawing Sheets

OTHER PUBLICATIONS

Computer Database Search, Search 1 Feb. 1996.
Computer Database Search, Search II 1996.
Computer Database Search, Search III 1996.
Computer Database Search, Search IV 1996.
Computer Database Search, Search V 1995.
Computer Database Search, Search VI Oct. 1995.
Computer Database Search, Search VII Jan. 1996.

* cited by examiner

PHARMACEUTICAL FOR TREATMENT OF NEUROLOGICAL AND NEUROPSYCHIATRIC DISORDERS

The present application is a continuation-in-part of: U.S. Ser. No. 08/656,063, filed May 31, 1996, now abandoned, U.S. Ser. No. 08/655,912, filed May 31, 1996, now abandoned, U.S. Ser. No. 08/808,755, filed Feb. 27, 1997, and U.S. Ser. No. 08/808,754, filed Feb. 27, 1997, now abandoned, each of which applications are now converted to provisional applications 60/041,503; 60/044,387; 60/041,504; and 60/070,900.

The present invention relates to a class of substituted amines, pharmaceutical compositions and methods of treating neurological and neuropsychiatric disorders.

Synaptic transmission is a complex form of intercellular communication that involves a considerable array of specialized structures in both the pre- and post-synaptic neuron. High-affinity neurotransmitter transporters are one such component, located on the pre-synaptic terminal and surrounding glial cells (Kanner and Schuldiner, CRC Critical Reviews in Biochemistry, 22, 1032 (1987)). Transporters sequester neurotransmitter from the synapse, thereby regulating the concentration of neurotransmitter in the synapse, as well as its duration therein, which together influence the magnitude of synaptic transmission. Further, by preventing the spread of transmitter to neighboring synapses, transporters maintain the fidelity of synaptic transmission. Last, by sequestering released transmitter into the presynaptic terminal, transporters allow for transmitter reutilization.

Neurotransmitter transport is dependent on extracellular sodium and the voltage difference across the membrane; under conditions of intense neuronal firing, as, for example, during a seizure, transporters can function in reverse, releasing neurotransmitter in a calcium-independent nonexocytotic manner (Attwell et al., Neuron, 11, 401–407 (1993)). Pharmacologic modulation of neurotransmitter transporters thus provides a means for modifying synaptic activity, which provides useful therapy for the treatment of neurological and psychiatric disturbances.

The amino acid glycine is a major neurotransmitter in the mammalian central nervous system, functioning at both inhibitory and excitatory synapses. By nervous system, both the central and peripheral portions of the nervous system are intended. These distinct functions of glycine are mediated by two different types of receptor, each of which is associated with a different class of glycine transporter. The inhibitory actions of glycine are mediated by glycine receptors that are sensitive to the convulsant alkaloid strychnine, and are thus referred to as "strychnine-sensitive." Such receptors contain an intrinsic chloride channel that is opened upon binding of glycine to the receptor, by increasing chloride conductance, the threshold for firing of an action potential is increased. Strychnine-sensitive glycine receptors are found predominantly in the spinal cord and brainstem, and pharmacological agents that enhance the activation of such receptors will thus increase inhibitory neurotransmission in these regions.

Glycine functions in excitatory transmission by modulating the actions of glutamate, the major excitatory neurotransmitter in the central nervous system. See Johnson and Ascher, Nature, 325, 529–531 (1987); Fletcher et al., Glycine Transmission, (Otterson and Storm-Mathisen, eds., 1990), pp. 193–219. Specifically, glycine is an obligatory co-agonist at the class of glutamate receptor termed N-methyl-D-aspartate (NMDA) receptor. Activation of NMDA receptors increases sodium and calcium conductance, which depolarizes the neuron, thereby increasing the likelihood that it will fire an action potential. NMDA receptors are widely distributed throughout the brain, with a particularly high density in the cerebral cortex and hippocampal formation.

Molecular cloning has revealed the existence in mammalian brains of two classes of glycine transporters, termed GlyT-1 and GlyT-2. GlyT-1 is found predominantly in the forebrain, and its distribution corresponds to that of glutamatergic pathways and NMDA receptors (Smith, et al., Neuron 8, 927–935 (1992)). Molecular cloning has further revealed the existence of three variants of GlyT-1, termed GlyT-1a, GlyT-1b and GlyT-1c (Kim, et al., Molecular Pharmacology, 45, 608–617 (1994)), each of which displays a unique distribution in the brain and peripheral tissues. These variants arise by differential splicing and exon usage, and differ in their N-terminal regions. GlyT-2, in contrast, is found predominantly in the brain stem and spinal cord, and its distribution corresponds closely to that of strychnine-sensitive glycine receptors (Liu et al., J. Biological Chemistry, 268, 22802–22808 (1993); Jursky and Nelson, J. Neurochemistry, 64, 1026–1033 (1995)). These data are consistent with the view that, by regulating the synaptic levels of glycine, GlyT-1 and GlyT-2 selectively influence the activity of NMDA receptors and strychnine-sensitive glycine receptors, respectively.

Compounds that inhibit or activate glycine transporters would thus be expected to alter receptor function, and provide therapeutic benefits in a variety of disease states. For example, inhibition of GlyT-2 can be used to diminish the activity of neurons having strychnine-sensitive glycine receptors via increasing synaptic levels of glycine, thus diminishing the transmission of pain-related (i.e., nociceptive) information in the spinal cord, which has been shown to be mediated by these receptors. Yaksh, Pain, 37, 111–123 (1989). Additionally, enhancing inhibitory glycinergic transmission through strychnine-sensitive glycine receptors in the spinal cord can be used to decrease muscle hyperactivity, which is useful in treating diseases or conditions associated with increased muscle contraction, such as spasticity, myoclonus, and epilepsy (Truong et al., Movement Disorders, 3, 77–87 (1988); Becker, FASEB J., 4, 2767–2774 (1990)). Spasticity that can be treated via modulation of glycine receptors is associated with epilepsy, stroke, head trauma, multiple sclerosis, spinal cord injury, dystonia, and other conditions of illness and injury of the nervous system.

NMDA receptors are critically involved in memory and learning (Rison and Stanton, Neurosci. Biobehav. Rev., 19, 533–552 (1995); Danysz et al., Behavioral Pharmacol., 6, 455–474 (1995)); and, furthermore, decreased function of NMDA-mediated neurotransmission appears to underlie, or contribute to, the symptoms of schizophrenia (Olney and Farber, Archives General Psychiatry, 52, 998–1007 (1996). Thus, agents that inhibit GlyT-1 and thereby increase glycine activation of NMDA receptors can be used as novel antipsychotics and anti-dementia agents, and to treat other diseases in which cognitive processes are impaired, such as attention deficit disorders and organic brain syndromes. Conversely, over-activation of NMDA receptors has been implicated in a number of disease states, in particular the neuronal death associated with stroke and possibly neurodegenerative diseases, such as Alzheimer's disease, multi-infarct dementia, AIDS dementia, Huntington's disease, Parkinson's disease, amyotrophic lateral sclerosis or other conditions in which neuronal cell death occurs, such as stroke or head trauma. Coyle & Puttfarcken, Science, 262, 689–695 (1993); Lipton and Rosenberg, New Engl. J. of Medicine, 330, 613–622 (1993); Choi, *Neuron*, 1, 623–634 (1988). Thus, pharmacological agents that increase the activity of GlyT-1 will result in decreased glycine-activation of NMDA receptors, which activity can be used to treat these and related disease states. Similarly, drugs that directly block the glycine site on the NMDA receptors can be used to treat these and related disease states.

SUMMARY OF THE INVENTION

By the present invention, a class of compounds has been identified that inhibit glycine transport via the GlyT-1 or GlyT-2 transporters, or are precursors, such as pro-drugs, to compounds that inhibit such transport, or are synthetic intermediates for preparing compounds that inhibit such transport. Thus, the invention provides a class of compounds formula:

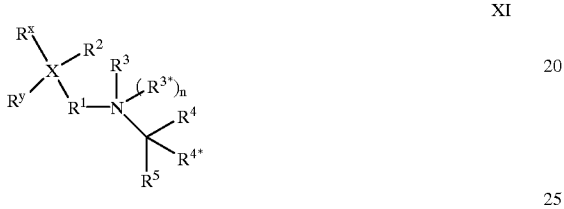

XI or a pharmaceutically acceptable salt thereof,
wherein:
(1) X is nitrogen or carbon, and $R^2$ is not present when X is nitrogen;
(2) $R^2$ (a) is hydrogen, (C1–C6) alkyl, (C1–C6) alkoxy, cyano, (C2–C7) alkanoyl, aminocarbonyl, (C1–C6) alkylaminocarbonyl or dialkylaminocarbonyl wherein each alkyl is independently C1 to C6, (b) comprises (where $R^1$ is not aminoethylene, —O—$R^8$ or —S—$R^{8*}$) hydroxy, fluoro, chloro, bromo or (C2–C7) alkanoyloxy, (c) forms a double bond with an adjacent carbon or nitrogen from one of either $R^1$, $R^{xb}$ or $R^{yb}$, or (d) is $R^{2a}$ linked by $R^{2b}$ to X;
($2^i$) $R^x$ is $R^{xa}$ linked by $R^{xb}$ to X;
($2^{ii}$) $R^y$ is $R^{ya}$ linked by $R^{yb}$ to X;
($2^{iii}$) $R^{xa}$, $R^{ya}$ and $R^{2a}$, are independently aryl, heteroaryl, adamantyl or a 5 to 7-membered non-aromatic ring having from 0 to 2 heteroatoms selected from the group consisting of oxygen, sulfur and nitrogen, wherein:
(a) aryl is phenyl or naphthyl,
(b) heteroaryl comprises a five-membered ring, a six-membered ring, a six-membered ring fused to a five-membered ring, a five-membered ring fused to a six-membered ring, or a six-membered ring fused to a six-membered ring, wherein the heteroaryl is aromatic and contains heteroatoms selected from the group consisting of oxygen, sulfur and nitrogen, with the remaining ring atoms being carbon,
(c) each of $R^{xa}$, $R^{ya}$ and $R^{2a}$ can be independently substituted with one of $R^q$, $R^rO$— or $R^sS$—, wherein each of $R^q$, $R^r$ and $R^s$ are independently aryl, heteroaryl, adamantyl or a 5 to 7-membered non-aromatic ring as these ring structures are defined for $R^{xa}$, and
(d) $R^{xa}$, $R^{ya}$, $R^{2a}$, $R^q$, $R^r$ and $R^s$ can be additionally substituted with one or more substituents selected from the group consisting of fluoro, chloro, bromo, nitro, hydroxy, cyano, trifluoromethyl, amidosulfonyl which can have up to two independent (C1–C6) N-alkyl substitutions, adamantyl, (C1–C12) alkyl, (C1–C12) alkenyl, amino, (C1–C6) alkylamino, dialkylamino wherein each alkyl is independently C1 to C6, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be substituted for hydrogen with up to two independent (C1–C6) alkyl, (C1–C6) alkylsulfonyl, amidino that can independently substituted with up to three (C1–C6) alkyl, or methylenedioxy or ethylenedioxy with the two oxygens bonded to adjacent positions on the aryl or heteroaryl ring structure, which methylenedioxy or ethylenedioxy can be substituted with up to two independent (C1–C6) alkyl, wherein:
(i.) the substitutions of $R^{xa}$, $R^{ya}$ and $R^{2a}$ can be combined to form a second bridge between two of $R^{xa}$, $R^{ya}$ and $R^{2a}$ comprising (1) (C1–C2) alkyl or alkenyl, which can be independently substituted with one or more (C1–C6) alkyl, (2) sulfur, (3) oxygen, (4) amino, which can be substituted for hydrogen with one (C1–C6) alkyl (5) carbonyl, (6) —CH$_2$C(=O)—, which can be substituted for hydrogen with up to two independent (C1–C6) alkyl, (7) —C(=O)—O—, (8) —CH$_2$—O—, which can be substituted for hydrogen with up to two independent (C1–C6) alkyl, (9) —C(=O)N($R^{24}$), wherein $R^{24}$ is hydrogen or (C1–C6) alkyl, (10) —CH$_2$—NH—, which can be substituted for hydrogen with up to three (C1–C6) alkyl, or (11) —CH=N—, which can be substituted for hydrogen with (C1–C6) alkyl, or wherein two of $R^{xa}$, $R^{ya}$ and $R^{2a}$ can be directly linked by a single bond;
($2^{iv}$) $R^{xb}$ and $R^{2b}$ are independently a single bond or (C1–C2) alkylene;
($2^v$) $R^{yb}$ is a singe bond, oxa, (C1–C2) alkylene, ethenylene or —CH= (where the double bond is with X), thia, methyleneoxy or methylenethio, or either —N($R^6$) or —CH$_2$—N($R^{6*}$)—, wherein $R^6$ and $R^{6*}$ are hydrogen or (C1–C6) alkyl, wherein when X is nitrogen X is not bonded to another heteroatom;
(3) $R^1$ comprises: a straight-chained (C2–C3) aliphatic group; where X is carbon, =N—O-(ethylene), wherein the unmatched double bond is linked to X; (where X is carbon and $R^{yb}$ does not include a heteroatom attached to X), —O—$R^8$or —S—$R^{8*}$ wherein $R^8$ or $R^{8*}$ is a ethylene or ethenylene and O or S is bonded to X; (where X is carbon and $R^{yb}$ does not include a heteroatom attached to X), aminoethylene where the amino is bonded to X:
wherein $R^1$ can be substituted with up to one hydroxy, up to one (C1–C6) alkoxy or up to one (C2–C7) alkanoyloxy, with up to two independent (C1–C6) alkyl, with up to one oxo, up to one (C1–C6) alkylidene, with the proviso that the hydroxy, alkoxy, alkanoyloxy or oxo substituents are not bonded to a carbon that is bonded to a nitrogen or oxygen;
wherein the alkyl or alkylidene substituents of $R^1$ can be linked to form a 3 to 7-membered non-aromatic ring; and
wherein if X is nitrogen, X is linked to $R^1$ by a single bond and the terminal carbon of $R^1$ that links $R^1$ to N is saturated;

(4) $R^3$ (a) is hydrogen, (C1–C6) alkyl, or phenyl or phenylalkyl wherein the alkyl is C1 to C6 and either such phenyl can be substituted with the same substituents defined above for the aryl or heteroaryl of $R^{xa}$, (b) is $-R^{12}Z(R^{xx})(R^{yy})(R^{11})$, wherein $R^{12}$ is bonded to N, Z is independently the same as X, $R^{xx}$ is independently the same as $R^x$, $R^{yy}$ is independently the same as $R^y$, $R^{11}$ is independently the same as $R^2$ and $R^{12}$ is independently the same as $R^1$, or (c) forms, together with $R^4$, a ring C, as follows:

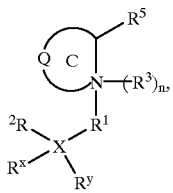

wherein $R^{4*}$ is hydrogen when ring C is present;

(5) n is 0 or 1, and where if n is 1, $R^{3*}$ is either (C1–C6) alkyl (with the attached nitrogen having a positive charge) or oxygen (forming an N-oxide) and X is carbon;

(5') Q together with the illustrated ring nitrogen and ring carbon bearing $R^5$ form ring C, wherein ring C is a 3 to 8-membered ring, a 3 to 8-membered ring substituted with a 3 to 6-membered spiro ring, or a 3 to 8-membered ring fused with a 5 to 6-membered ring, wherein the fused ring lacking the illustrated ring nitrogen can be aromatic or heteroaromatic, wherein for each component ring of ring C there are up to two heteroatoms selected from oxygen, sulfur or nitrogen, including the illustrated nitrogen, and the rest carbon, with the proviso that the ring atoms include no quaternary nitrogens other than the illustrated nitrogen, with the proviso that, in saturated rings, ring nitrogen atoms are separated from other ring heteroatoms by at least two intervening carbon atoms:

wherein the carbon and nitrogen ring atoms of ring C can be substituted with substituents selected from (C1–C6) alkyl, (C2–C6) alkenylene, cyano, nitro, trifluoromethyl, (C2–C7) alkyloxycarbonyl, (C1–C6) alkylidene, hydroxyl, (C1–C6) alkoxy, oxo, hydroxycarbonyl, aryl wherein the aryl is as defined for $R^{xa}$ or heteroaryl wherein the heteroaryl is as defined for $R^{xa}$, with the proviso that ring atoms substituted with alkylidene, hydroxycarbonyl or oxo are carbon, with the further proviso that ring atoms substituted with hydroxyl or alkoxy are separated from other ring heteroatoms by at least two intervening carbon atoms;

(6) $R^4$ and $R^{4*}$ are independently hydrogen or (C1–C6) alkyl, or one of $R^4$ and $R^{4*}$ can be (C1–C6) hydroxyalkyl; and (7) $R^5$ is $(CO)NR^{13}R^{14}$, $(CO)OR^{15}$, $(CO)SR^{16}$, $(SO_2)NR^{17}R^{18}$, $(PO)(OR^{19})(OR^{20})$, $(CR^{22})(OR^{23})(OR^{24})$, CN or tetrazol-5-yl, wherein $R^{13}$, $R^{14}$, $R^{15}$, $R^{16}$, $R^{17}$, $R^{18}$ $R^{19}$ and $R^{20}$ are independently hydrogen, (C1–C6) alkyl which can include a (C3–C8) cycloalkyl, wherein the carbon linked to the oxygen of $R^{15}$ or the sulfur of $R^{16}$ has no more than secondary branching and, (C2–C6) hydroxyalkyl, aminoalkyl where the alkyl is C2 to C6 and the amino can be substituted with up to two independent (C1–C6) alkyls, arylalkyl wherein the alkyl is C1–C6, heteroarylalkyl wherein the alkyl is C1 to C6, aryl or heteroaryl, $R^{22}$ is hydrogen or $OR^{25}$ and $R^{23}$, $R^{24}$ and $R^{25}$ are (C1–C6) alkyl, phenyl, benzyl, acetyl or, where $R^{22}$ is hydrogen, the alkyls of $R^{23}$ and $R^{24}$ can be combined to include 1,3-dioxolane or 1,3-dioxane:

wherein the aryl is phenyl or naphthyl and the heteroaryl is a five-membered ring, a six-membered ring, a six-membered ring fused to a five-membered ring, a five-membered ring fused to a six-membered ring, or a six-membered ring fused to a six-membered ring, wherein the heteroaryl is aromatic and contains heteroatoms selected from the group consisting of oxygen, sulfur and nitrogen, with the remaining ring atoms being carbon;

wherein the aryl, heteroaryl, aryl or arylalkyl or the heteroaryl of heteroarylalkyl can be substituted with [preferably up to three] substituents selected from the group consisting of fluoro, chloro, bromo, nitro, cyano, hydroxy, trifluoromethyl, amidosulfonyl which can have up to two independent (C1–C6) N-alkyl substitutions, (C1–C6) alkyl, (C2–C6) alkenyl, (C1–C6) alkylamine, dialkylamine wherein each alkyl is independently C1 to C6, amino, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be N-substituted with up to two independent (C1–C6) alkyl, (C1–C6) alkylsulfonyl, amidino that can substituted with up to three (C1–C6) alkyl, or methylenedioxy or ethylenedioxy with the two oxygens bonded to adjacent positions on the aryl or heteroaryl ring structure, which methylenedioxy or ethylenedioxy can be substituted with up to two independent (C1–C6) alkyl; and wherein $R^{13}$ and $R^{14}$ together with the nitrogen can form a 5 to 7-membered ring that can contain one additional heteroatom selected from oxygen and sulfur.

In a preferred embodiment, the ring Q is a 4 to 8-membered ring that includes the illustrated ring nitrogen, with the remaining ring atoms being carbon.

Preferably, (A) at least one of $R^{xa}$, $R^{ya}$ and $R^{2a}$ is substituted with fluoro, chloro, bromo, hydroxy, trifluoromethyl, trifluoromethoxy, nitro, cyano, (C3–C8) alkyl, $R^q$, $R^rO-$, $R^sS-$, (B) $R^3$ is hydrogen, (C1–C6) alkyl, or phenyl or phenylalkyl wherein the alkyl is C1 to C6 and either such phenyl can be substituted with the same substituents defined for the aryl or heteroaryl of $R^{xa}$ or (C) the ring structures of $R^{xa}$, $R^{ya}$ and $R^{2a}$, including substituents thereto, otherwise include at least two aromatic ring structures that together include from 15 to 20 ring atoms. Examples of preferred structures under clause (C) include A45, A53, A56, A57, A60–5, A73–74, A78–81, A86–89, A93–96, A99, A100, A102, A105–106, A108–109, A116, A122–123 and A176. Preferably, at least one of $R^{xa}$, $R^{ya}$ and $R^{2a}$ is substituted with fluoro, trifluoromethyl, trifluoromethoxy, nitro, cyano, or (C3–C8) alkyl. Preferably, $R^{xa}$, $R^{ya}$ and $R^{2a}$ is substituted with $R^q$, $R^rO-$, or $R^sS-$. Preferably, an aryl or heteroaryl of at least one of $R^{xa}$, $R^{ya}$ and $R^{2a}$ is phenyl. Preferably, $R^{yb}$ is oxa, methyleneoxy, thia, methylenethia. Preferably, $R^{yb}$ is oxa or thia. Preferably, $R^5$ is $(CO)NR^{13}R^{14}$, $(CO)OR^{15}$ or $(CO)SR^{16}$.

In one embodiment, $R^{15}$ is (C2–C6) alkyl, (C2–C4) hydroxyalkyl, phenyl, phenylalkyl wherein the alkyl is C1–C3, or aminoalkyl where the alkyl is C2–C6 and the amino can be substituted with up to two independent (C1–C3) alkyls, wherein the phenyl or the phenyl of phenylalkyl can be substituted as recited above. Preferably, n is zero. Preferably, $R^{15}$ is hydrogen. Preferably, $R^4$ is hydrogen, methyl or hydroxymethyl and $R^{4*}$ is hydrogen. Preferably, at least one of $R^{xa}$, $R^{ya}$ and $R^{2a}$ is a heteroaryl comprising diazolyl, triazolyl, tetrazolyl, thiazolyl, isothiazolyl, oxazolyl, isoxazolyl, thiolyl, diazinyl, triazinyl, benzoazolyl, benzodiazolyl, benzothiazolyl, benzoxazolyl, benzoxolyl, benzothiolyl, quinolyl, isoquinolyl, benzodiazinyl, benzotriazinyl, pyridyl, thienyl, furanyl, pyrrolyl, indolyl, isoindoyl or pyrimidyl. Preferably, $R^1$ is —O—$R^8$ or —S—$R^{8*}$. Preferably, the second bridge between two of $R^{xa}$, $R^{ya}$ and $R^{2a}$ (of Section ($2^{iii}$)(d)(i.)) is L, and satisfies the following formula:

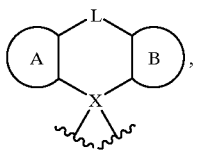

wherein A and B are aryl or heteroaryl groups of $R^{xa}$ and $R^{ya}$, respectively. Preferably, $R^{xa}$—$R^{xb}$—, $R^{ya}$—$R^{yb}$— and X form:

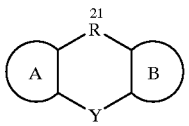

wherein Y is a carbon bonded to $R^1$ by a single or double bond or a nitrogen that is bonded to $R^1$ and wherein $R^{21}$ either (i.) completes a single bond linking two aryl or heteroaryl rings of $R^x$ and $R^y$, (ii.) is (C1–C2) alkylene or alkenylene, (iii.) is sulfur or (iv.) is oxygen, and wherein $R^x$ and $R^y$ can be substituted as set forth above. Preferably, $R^{21}$ is $CH_2CH_2$ or CH=CH. Preferably, the alkylenedioxy substitution of $R^{xa}$, $R^{ya}$, $R^{2a}$, $R^q$, $R^r$ or $R^s$ is as follows:

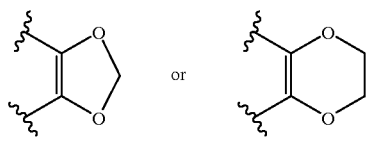

wherein the alkylenedioxy can be substituted with up to two independent (C1–C3) alkyl.

In one preferred embodiment, $R^{xa}$ and $R^{ya}$ together can be substituted with up to six substituents, $R^{2a}$, $R^q$, $R^r$ and $R^s$ can each be substituted with up to 3 substituents, and wherein the presence of each of $R^q$, $R^r$ or $R^s$ is considered a substitution to the respective ring structure of $R^{xa}$, $R^{ya}$ and $R^{2a}$. Preferably, a phenyl of $R^3$ is substituted with up to three substituents. Preferably, the compound is an optically pure enantiomer (i.e., at least about 80% ee, preferably at least about 90% ee, more preferably at least about 95% ee). Preferably, the compound is part of a pharmaceutical composition comprising a pharmaceutically acceptable excipient. Preferably, the compound of the composition is present in an effective amount for:

(1) treating or preventing schizophrenia,
(2) enhancing treating or preventing dementia,
(3) treating or preventing epilepsy,
(4) treating or preventing spasticity,
(5) treating or preventing muscle spasm,
(6) treating or preventing pain,
(7) preventing neural cell death after stroke,
(8) preventing neural cell death in an animal suffering from a neurodegenerative disease
(9) treating or preventing mood disorders such as depression,
(10) enhancing memory or learning, or
(11) treating or preventing learning disorders.

In another embodiment, the invention provides a method (1) of treating or preventing schizophrenia comprising administering a schizophrenia treating or preventing effective amount of a compound, (2) of treating or preventing dementia comprising administering a dementia treating or preventing effective amount of a compound, (3) of treating or preventing epilepsy comprising administering an epilepsy treating or preventing effective amount of a compound, (4) of treating or preventing spasticity comprising administering a spasticity treating or preventing effective amount of a compound, (5) of treating or preventing muscle spasm comprising administering a muscle spasm treating or preventing effective amount of a compound, (6) of treating or preventing pain comprising administering a pain treating or preventing effective amount of a compound, (7) of preventing neural cell death after stroke comprising administering a neural cell death preventing effective amount of a compound, (8) of preventing neural cell death in an animal suffering from a neurodegenerative disease, (9) treating or preventing mood disorders such as depression, (10) enhancing memory or learning, or (11) treating or preventing learning disorders, comprising administering an amount effective for said treating, preventing or enhancing of a compound of formula XI or a pharmaceutically acceptable salt thereof, wherein the substituents are as defined above, except that $R^{25}$ differs from $R^1$ in that it can be a straight-chained C4 aliphatic group. Preferably, the spasticity treated or prevented is associated with epilepsy, stroke, head trauma, multiple sclerosis, spinal cord injury or dystonia. Preferably, the neurodegenerative disease treated or prevented is Alzheimer's disease, multi-infarct dementia, AIDS dementia, Parkinson's disease, Huntington's disease, amyotrophic lateral sclerosis or stroke or head trauma (such as can result in neuronal cell death).

In another embodiment, the invention provides a method of synthesizing a compound of the invention comprising:

A) reacting a compound of one of the following formulas
1)

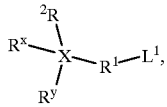

wherein $L^1$ is a nucleophilic substitution leaving group, with a compound of the formula
2)

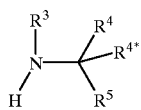

or

B) reacting a compound of the formula
1)

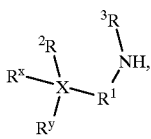

with a compound of the formula
2)

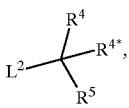

wherein $L^2$ is a nucleophilic substitution leaving group.

In another embodiment, the invention provides a method of synthesizing a compound of the invention comprising:

A) reductively alkylating a compound of the formula
1)

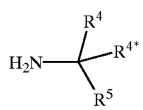

with a compound of the formula
2)

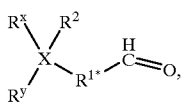

where $R^{1*}$ differs from $R^1$ in that it lacks the carbon that is part of the illustrated aldehyde carbonyl,

OR

B) reductively alkylating a compound of the formula
1)

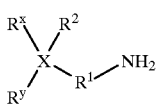

with a compound of the formula
2)

In another embodiment, the invention provides a method of synthesizing a compound of the invention comprising reductively alkylating $R^d NH_2$ with a compound of the formula

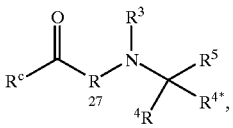

wherein $R^d$ and $R^c$ are independently the same as defined for $R^x$, and wherein $R^{27}$ has the same definition as $R^1$ except that it does not include a nitrogen, oxygen or sulfur and does not include any double bonds conjugated with the above-illustrated carbonyl.

In another embodiment, the invention provides a method of synthesizing a compound of the invention comprising reacting $R^f OH$ or $R^{f*} SH$ with a compound of the formula

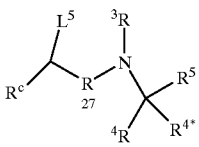

to form an ether or a thioether, respectively, wherein $R^f$ and $R^{f*}$ are independently the same as defined for $R^x$, wherein $R^{27}$ has the same definition as $R^1$ except that it does not include a nitrogen, oxygen or sulfur and does not include any double bonds at the atom bonded to the above-illustrated $L^5$-substituted carbon and wherein $L^5$ is a nucleophilic substitution leaving group.

The method of claim 28, further comprising synthesizing the compound of formula

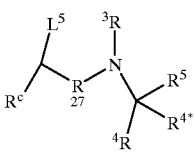

by replacing the hydroxyl of formula

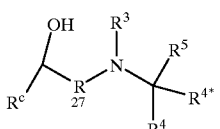

with another nucleophilic substitution leaving group. Preferably, the method comprises reacting a compound of formula

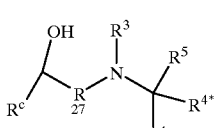

with an azodicarboxylate in the presence of a phosphine compound.

In another embodiment, the invention provides a method of synthesizing a compound of the invention comprising reacting $R^e M$ with a compound of the formula

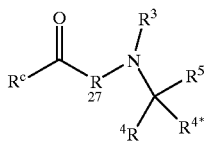

to form a compound of the formula

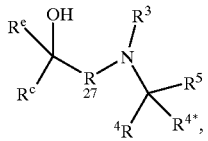

wherein $R^e$ is independently the same as defined for $R^x$, wherein M is a metal-containing substituent such that $R^eM$ is a organometallic reagent.

In another embodiment, the invention provides a method of synthesizing a compound of the invention comprising dehydrating a compound of the formula

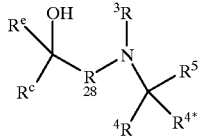

to form a compound of the formula

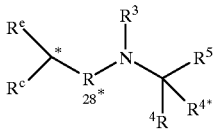

wherein C* (the tertiary carbon marked with an adjacent "*") has a double bond with an adjacent carbon, $R^{28*}$ and $R^{28}$ have the same definition as $R^1$ except that $R^{28*}$ and $R^{28}$ do not include a heteroatom.

In another embodiment, the invention provides a method of synthesizing a compound of the invention comprising reducing a compound of the formula

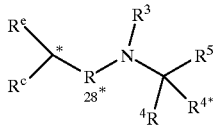

wherein C* has a double bond with an adjacent carbon and $R^c$ is independently the same as defined for $R^x$, to form a compound of the formula

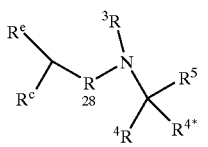

In another embodiment, the invention provides a method of synthesizing a compound that can be used to synthesize the compound of the invention, the method comprising synthesizing the compound of formula:

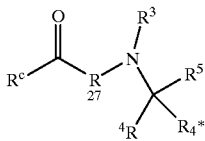

with a compound of formula

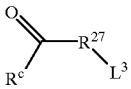

with a compound of formula

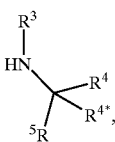

wherein $L^3$ is a nucleophilic substitution leaving group.

In another embodiment, the invention provides a method of synthesizing of a compound of the invention, the method comprising reacting a compound of formula

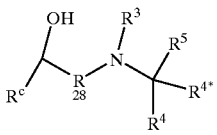

with Ar-Q wherein Ar is aryl which is substituted with an electron-withdrawing group or heteroaryl which is substituted with an electron-withdrawing group, and wherein Q is halide (preferably fluoro or chloro), to form

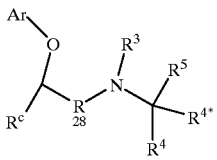

In another embodiment, the invention provides a method of synthesizing a compound that can be used to synthesize the compound of the invention, the method comprising synthesizing a compound of formula X:

X

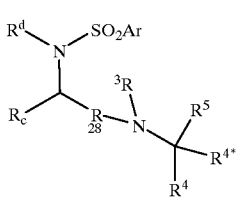

by reacting a compound of formula:

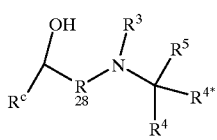

with R$^d$NHSO$_2$Ar. The method can further comprise converting the compound of formula X to:

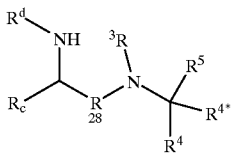

In another embodiment, the invention provides a method of synthesizing a compound that can be used to synthesize the compound of the invention, the method comprising reacting a compound of formula

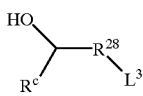

with a compound of formula

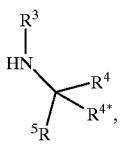

to form a compound of formula

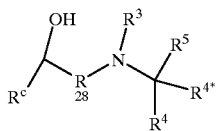

In another embodiment, the invention provides a method of synthesizing a compound that can be used to synthesize the compound of the invention, the method comprising synthesizing the compound of formula:

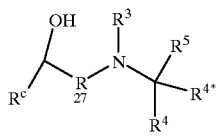

said synthesis comprising reducing the ketone of a compound of formula

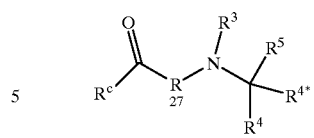

DEFINITIONS

Figure 1:
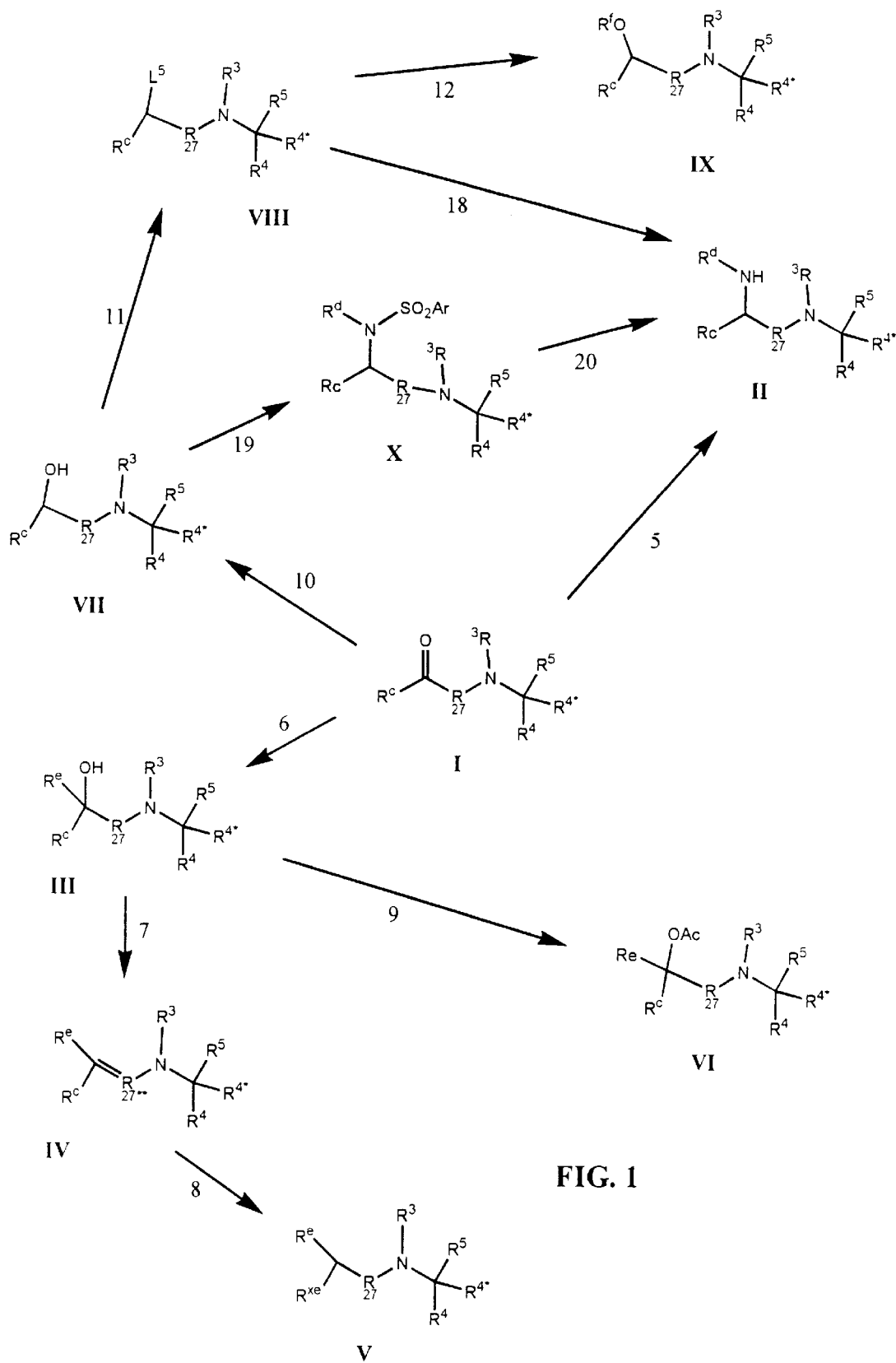
FIG. 1 depicts several reactions that can be employed in the synthesis of the compounds of the invention.

The following terms shall have the meaning set forth below:

excipient
  Excipients are pharmaceutically acceptable organic or inorganic carrier substances suitable for parenteral, enteral (e.g., oral or inhalation) or topical application that do not deleteriously react with the active compositions. Suitable pharmaceutically acceptable carriers include but are not limited to water, salt solutions, alcohols, gum arabic, benzyl alcohols, gelatine, carbohydrates such as lactose, amylose or starch, magnesium stearate, talc, silicic acid, hydroxymethylcellulose, polyvinylpyrrolidone, and the like.

effective amount
  The meaning of "effective amount" will be recognized by clinicians but includes amount effective to (1) reduce, ameliorate or eliminate one or more symptoms of the disease sought to be treated, (2) induce a pharmacological change relevant to treating the disease sought to be treated, or (3) prevent or lessen the frequency of occurrence of a disease.

neuronal cell death prevention
  Neuronal cell death is "prevented" if there is a reduction in the amount of cell death that would have been expected to have occurred but for the administration of a compound of the invention.

oxo substitution
  References to oxo as a "substituent" refer to "=O" substitutions.

DETAILED DESCRIPTION

The compounds of the invention are generally prepared according to one of the following synthetic schemes, although alternative schemes will be recognized by those of ordinary skill.

Reaction 1

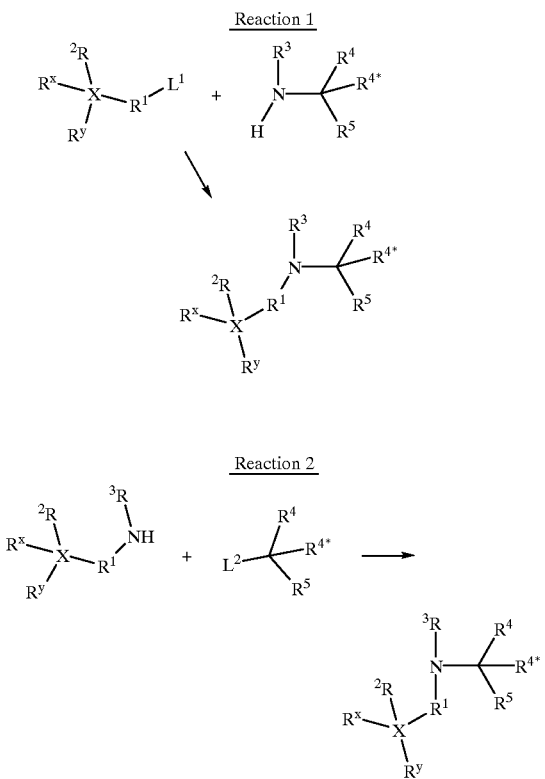

Reaction 2

In Reaction 1 or Reaction 2, $L^1$ and $L^2$ are good nucleophilic substitution leaving groups such as a halide, especially a bromide, a tosylate, a brosylate (p-bromobenzenesulfonate), and the like. The reaction is preferably conducted in the presence of a base such as potassium carbonate or a tertiary amine such as diisopropylethylamine. Where the leaving group is a halide, the reaction is preferably conducted in the presence of an iodide salt such as potassium iodide. Suitable organic solvents include, for example, methanol, dioxane, acetonitrile or dimethyformamide. Reaction 1 is favorably conducted at a temperature range of about 50° C. to about 100° C. Reaction 2 is favorably conducted at a temperature range of about 15° C. to about 40° C. Avoiding more elevated temperatures helps decrease the formation of additional alkylation products. Those of ordinary skill will recognize that reaction 2 should be conducted with compounds that lack ring C.

Reaction 3

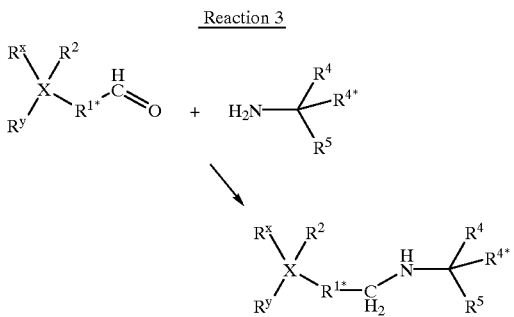

Reaction 4

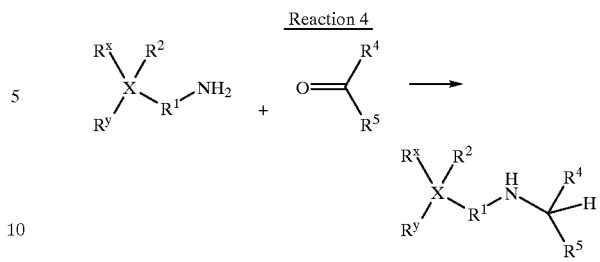

In Reaction 3, $R^{1*}$ satisfies the definition of $R^1$ except for the absence of the carbon that is part of an aldehyde group in the starting material. The reductive alkylation of Reaction 3 or Reaction 4 can be effected by several known methods (see, for example, "Reductive Alkylation," W. S. Emerson in *Organic Reactions*, Vol. 4, John Wiley & Sons, 1948, p. 174 et seq.) including reaction with hydrogen in the presence of a catalyst such as palladium on carbon, reaction with sodium cyanoborohydride or reaction with sodium triacetoxyborohydride when groups labile to catalytic hydrogenation are present. It will be recognized that an intermediate Schiff's base is formed in the reaction, which Schiff's base is reduced to form the linkage. The intermediate Schiff's base can be isolated and then reduced in a separate reaction. Solvent selection will vary with such factors as the solubility of the starting materials, the degree to which the solvent favors the dehydration reaction forming the Schiff's base, and the suitability of the solvent in the reduction process. Suitable solvents using catalytic hydrogenation to reduce the Schiff's base include ethanol. Suitable solvents using a borohydride to reduce the Schiff's base include alcoholic solvents such as methanol or ethanol. In some cases, a drying process can be employed during the reaction to promote the dehydration reaction that forms the Schiff's base that is reduced. Such drying processes include refluxing under conditions selected to remove water as an azeotrope or the use of molecular sieves or other drying reagents. Suitable reaction temperatures include the range from about 20° C. to the reflux temperature of the solvent employed.

In Reaction 5, shown in FIG. 1, $R^c$ is independently the same as defined for $R^x$. The starting material I can be synthesized, for instance, using the chemistry of Reaction 13 (similar to Reaction 1), as follows:

Reaction 13

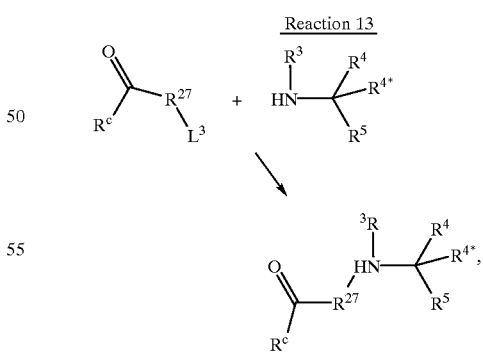

wherein $R^{27}$ has the same definition as $R^1$ except that it does not include a nitrogen, oxygen or sulfur and does not include any double bonds conjugated with the above-illustrated carbonyl, and wherein $L^3$ is a good nucleophilic substitution leaving group such as a halide, especially a bromide, a tosylate, a brosylate (p-bromobenzenesulfonate), and the like. In Reaction 5 shown in FIG. 1, $R^d$—$NH_2$ is reacted with I to give II under conditions that effect a reductive alkylation, as described for Reaction 3 and Reaction 4. $R^d$ is independently the same as defined for $R^x$. Alternatively, II can be synthesized via Reaction 18 by reacting $R^d$—$NH_2$ with VIII under the conditions described for Reaction 1.

In Reaction 6, shown in FIG. 1, $R^e$ is independently the same as defined for $R^x$. In Reaction 6, I is reacted with a organometallic reagent such as an aryllithium or an aryl or arylalkyl Grignard reagent to form III, as described, for instance, in Section 5.1.2 of Cary and Sundberg, Advanced Organic Chemistry, Part 2, Plenum, New York, 1977, pp. 170–180, and references cited therein. This reaction is described below in more detail for the synthesis of compound A32 (step 2 of Example 5A). Those of ordinary skill will be aware that in some cases where $R^5$ includes an ester, the organometallic reagent may react with the ester group; in those such cases where the yield of the desired product is too low, the solvent, the organometallic reagent or the ester substitution can be varied.

In Reaction 7, shown in FIG. 1, III is subjected to conditions suitable for dehydration to form the double bond of IV. Such conditions are, for instance, those described in H. Weiland, Ber. 45: 484 et seq. (1912), wherein III is refluxed with acetic anhydride. In the illustration, the double bond forms with the adjacent carbon atom of $R^{27}$. The double bond will typically form with this orientation where $R^c$ and $R^e$ are aryl or heteroaryl and the adjacent carbon of $R^{27}$ is saturated and not fully substituted, but other orientations are possible depending on the composition of $R^c$, $R^e$ and $R^{27}$.

In Reaction 8, shown in FIG. 1, IV is reduced to form V, for instance using any of a number of known methods for reducing carbon—carbon double bonds, such as catalytic hydrogenation in the presence of an appropriate hydrogenation catalyst. An example of this process is described below for compound A4 (Example 10).

In Reaction 9, shown in FIG. 1, III is acylated, for instance, with acetic anhydride in the presence of an acylation catalyst such as 4-dimethylaminopyridine. In this context, $R^3$ should not be hydrogen, though a hydrogen substituent can be restored to this position after Reaction 9 by using a suitable protecting group to mask the nitrogen.

In Reaction 10, shown in FIG. 1, the ketone moiety of I is reduced, for instance by any of a number of known methods for selectively reducing ketones, such as reaction with lithium tri-tert-butoxyaluminohydride. An example of this process is described below for the preparation of compound A31 (step 1 of Example 8A).

For Reaction 11, shown in FIG. 1, the hydroxyl of VII is replaced by a leaving group $L^5$, wherein the leaving group is, for instance, chloro or bromo, by reacting VII with, for instance, thionyl chloride or thionyl bromide. An example of this process is described below for the preparation of compound A31 (step 2 of Example 8A).

For Reaction 12, shown in FIG. 1, $R^f$ is independently the same as defined for $R^x$. VIII is reacted with $R^fOH$ in the presence of a base such as potassium carbonate or sodium hydride. Alternatively, the thio-containing analog of IX can be synthesized by reacting VIII with $R^fSH$. An example of this process is described below for the synthesis of compound A31 (step 3 of Example 8A). The transformations of Reactions 11 and 12 can be conducted in a single pot, for instance by a Mitzunobu reaction such as described in Examples 8C, Step 1 and 8D, Step 2. Alternatively, VII can be directly reacted with an aryl halide or chloride, preferably an aryl fluoride or chloride, to form IX, such as is described in U.S. Pat. Nos. 5,166,437 and 5,362,886. It will be recognized that typically the aryl halide used in this reaction will typically have an electron-withdrawing group that facilitates the reaction, such as a trifluoromethyl or nitro group in the para position. 1-fluoronaphthalene is also suitable for this reaction, since the ring fused to the fluoro-substituted ring is the electron withdrawing group.

In reaction 19, VII is reacted with $R^dNHSO_2Ar$ to yield X, as described for example in Example 8C, Step 1. In reaction 20, X is coverted to II as described, for example, in Example 8C, Step 2.

A number of other well-known synthetic approaches can be applied. For instance, acids can be formed by the hydrolysis of the corresponding esters. Amine derivatives can be formed by the alkylation of primary, secondary or tertiary amines. A number of double bond containing compounds can be hydrogenated to form the corresponding single bond. The N-oxide compounds of the invention are typically formed from the corresponding tertiary nitrogen by known methods.

In some cases, the chemistries outlined above may have to be modified, for instance by use of protective groups, to prevent side reactions due to reactive groups, such as reactive groups incorporated into heterocyclic rings or attached as substituents.

Compounds of the invention may also be prepared by adapting the classical solution chemistries outlined above into solid-phase synthetic techniques. For example, $R^{13}$, $R^{15}$, $R^{16}$, $R^{17}$ and $R^{20}$ can be residues other than hydrogen representing functionalized resin or suitably selected linker attached to functionalized resin. The linker and the functional group represented by $R^5$ should be stable under the conditions employed for the above-described reactions. The compounds of the invention where $R^{13}$, $R^{15}$, $R^{16}$, $R^{17}$ is $R^{20}$ is hydrogen, are then cleaved from the resin or the linker leaving the remainder of the molecule intact. For example, solid-phase synthesis of peptoids [oligo(N-substituted glycines)] using robotic synthesizer was described by Zuckermann et al., J. Am. Chem. Soc., 114, 10646–10647, (1992) and Spellmeyer et al., WO 95/04072. Under analogous conditions, acylation reaction of Rink amide polystyrene resin with bromoacetic acid in the presence of N,N'-diisopropylcarbodiimide followed by displacement of the bromine with N-substituted amine (Reaction 2) and cleavage can provide N-substituted glycinamides ($R^{13}$ and $R^{14}$ are hydrogen).

Using the reactions described herein, including hydrolysis of esters, alkylation of amines, or hydrogenation reactions, the following compounds of the invention have been synthesized:

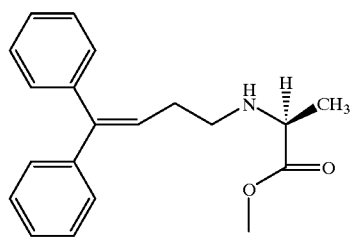

A1

A2
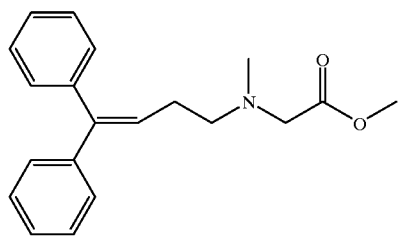
A3
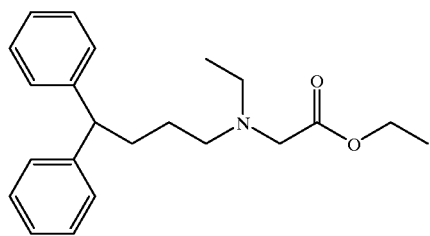
A4
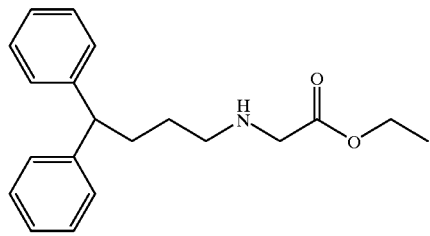
A5
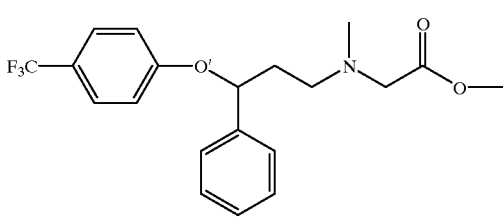
A6
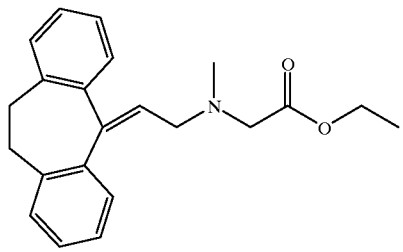
A7
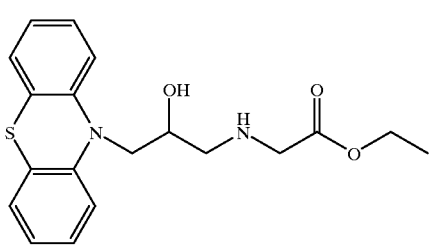
A8
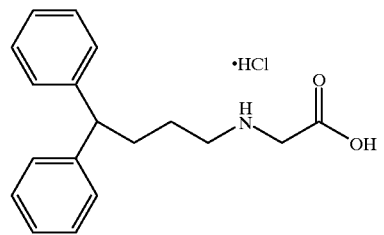
A9
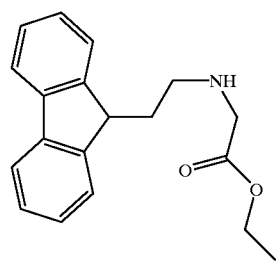
A10
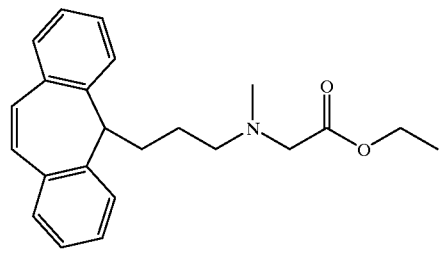
A11
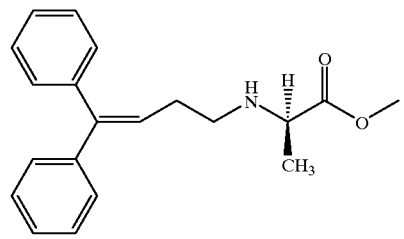
A12
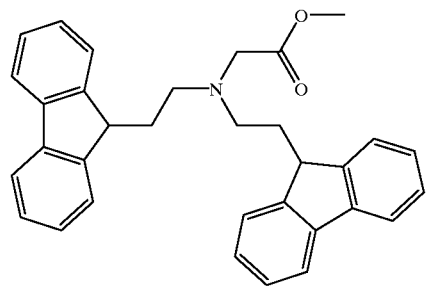
A13
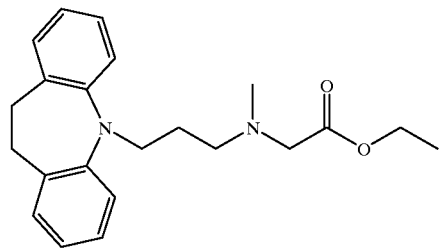

-continued
A14
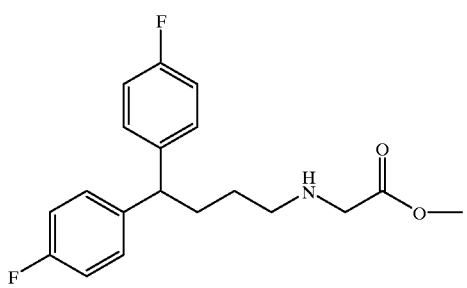
A15
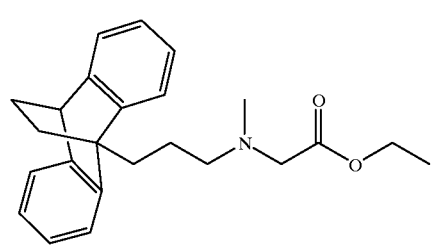
A16
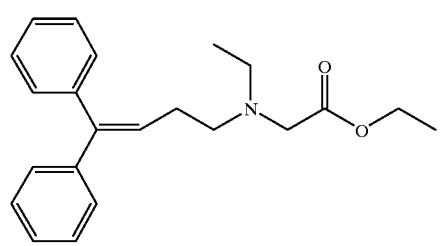
A17
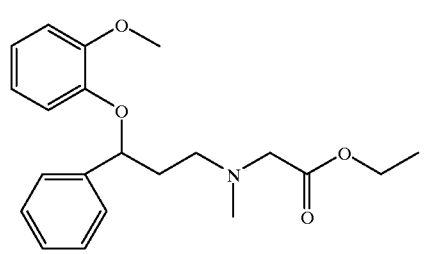
A18
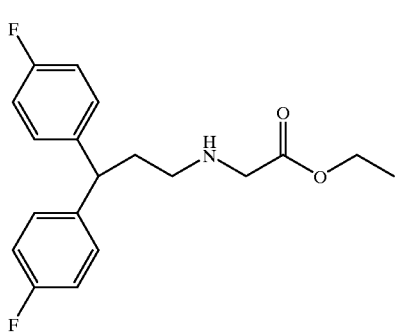
A19
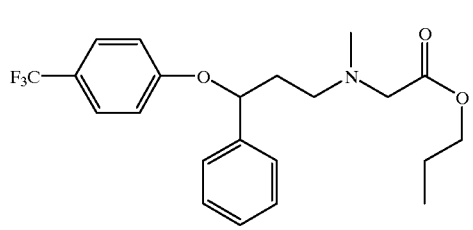
-continued
A20
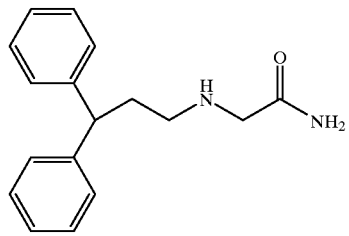
A21
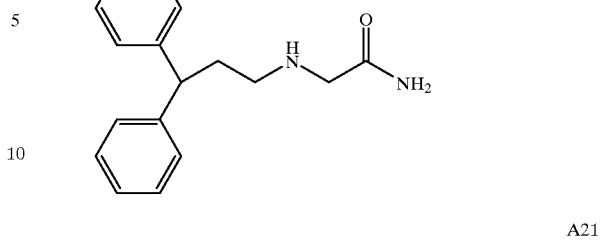
A22
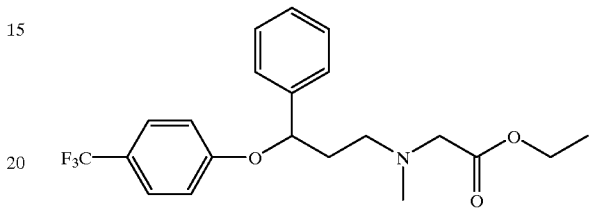
A23
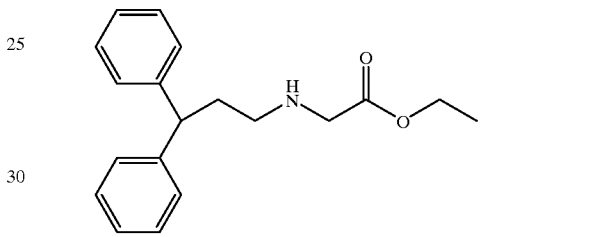
A24
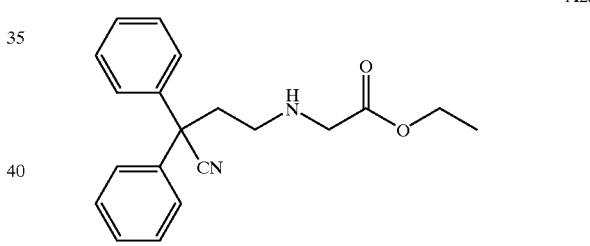
A25
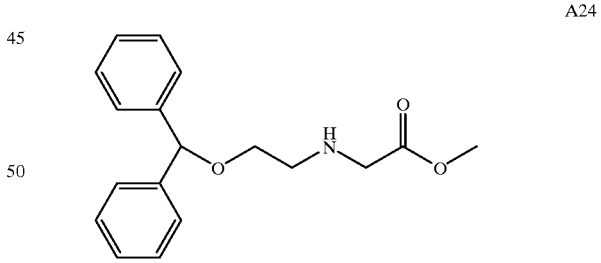
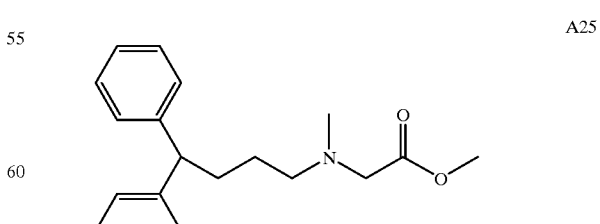

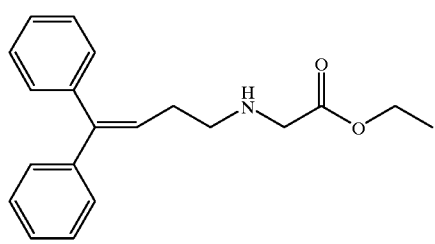
A26
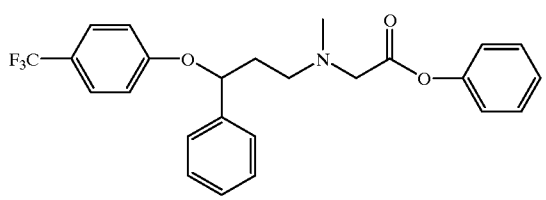
A33
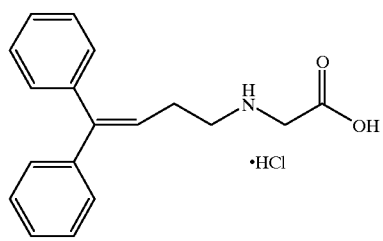
A27
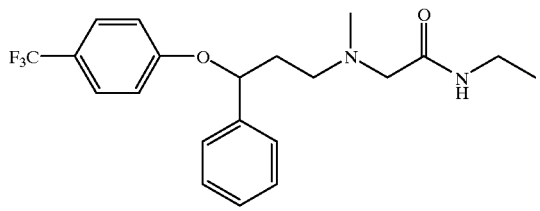
A34
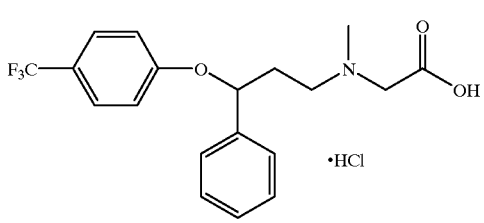
A29
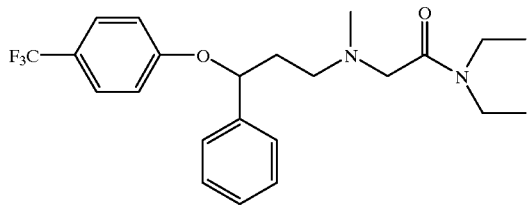
A35
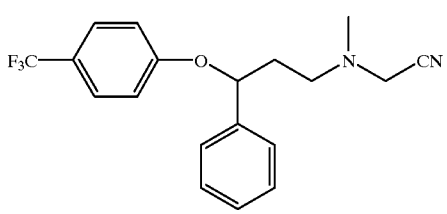
A30
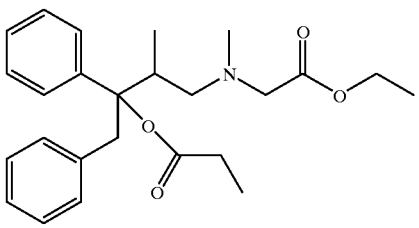
A36
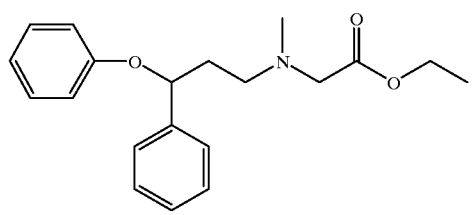
A31
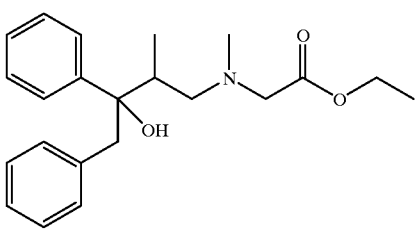
A37
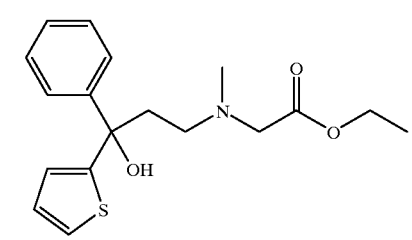
A32
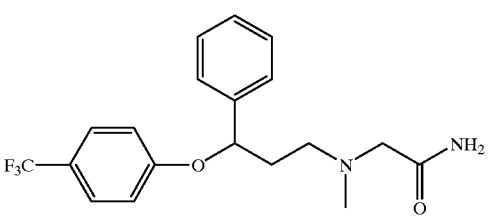
A38

-continued
A39
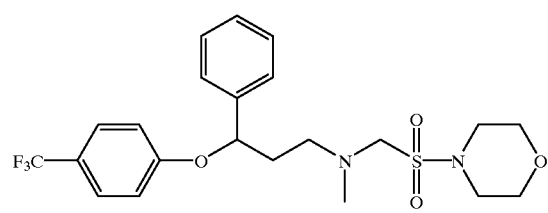
A40
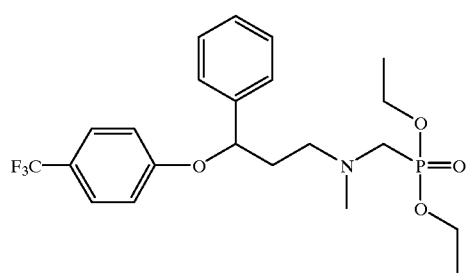
A41
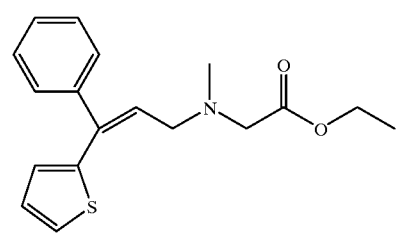
A42
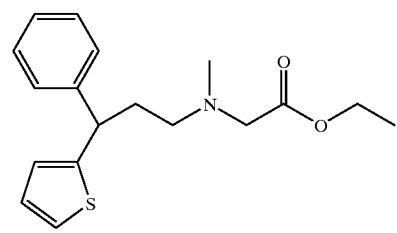
A43
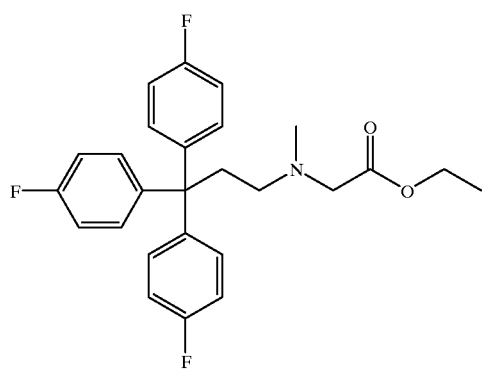
-continued
A44
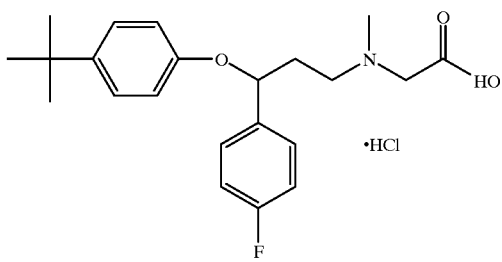
A45
A46
A47
A48
A49

A50
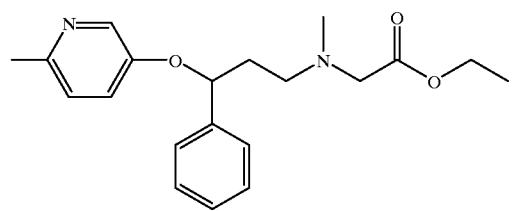
A51
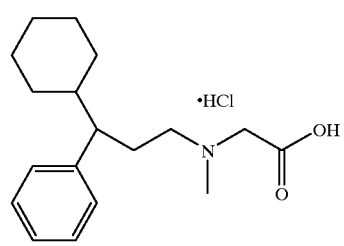
A52
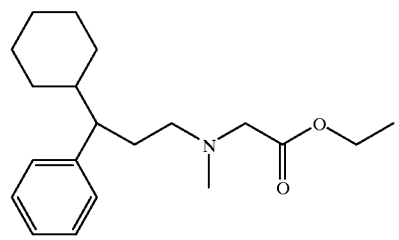
A53
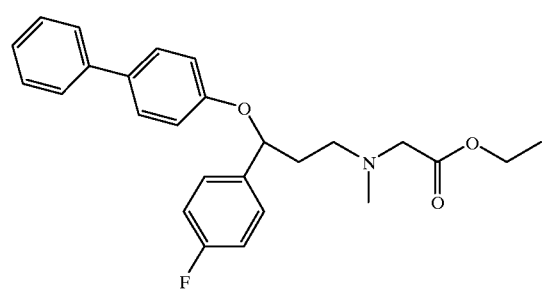
A54
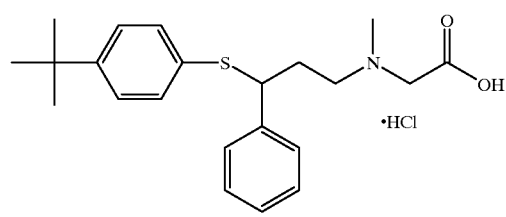
A55
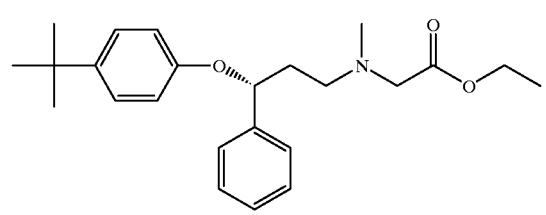
A56
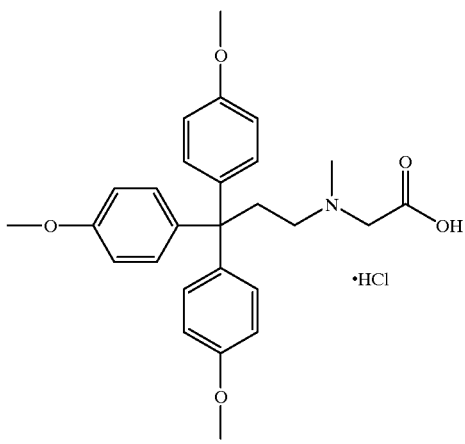
A57
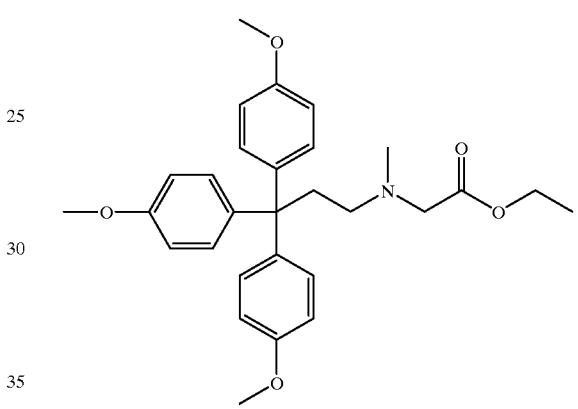
A58
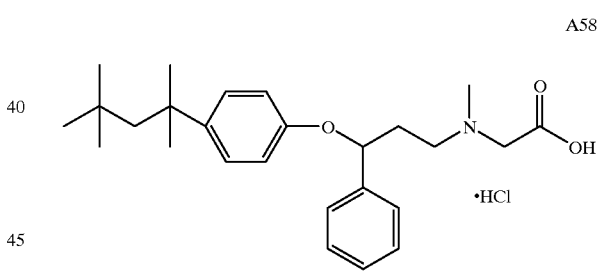
A59
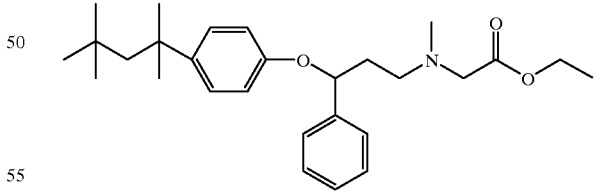
A60
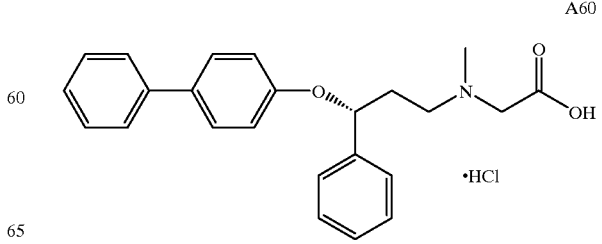

-continued

A61 A62 A63 A64 A65 A66 A67 A68 A69 A70 A71 A72

A73 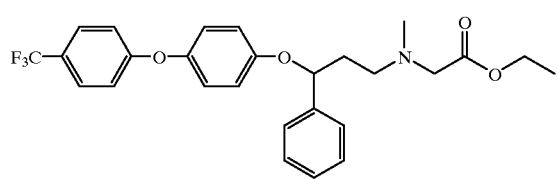
A74 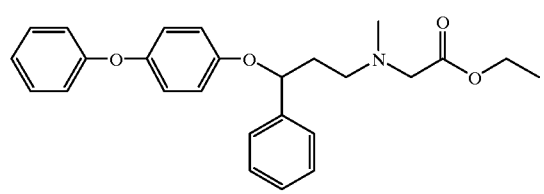
A75 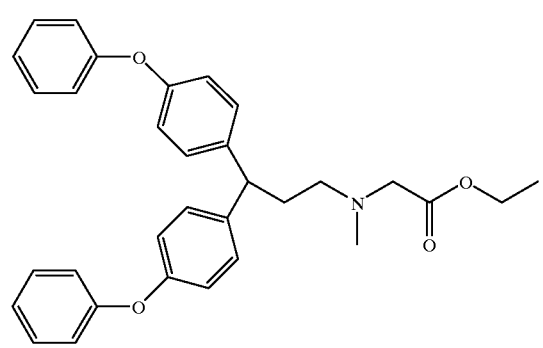
A76 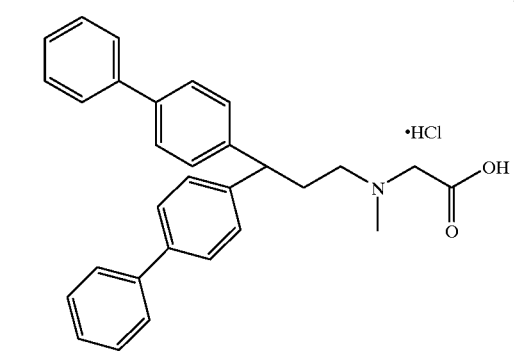
A77 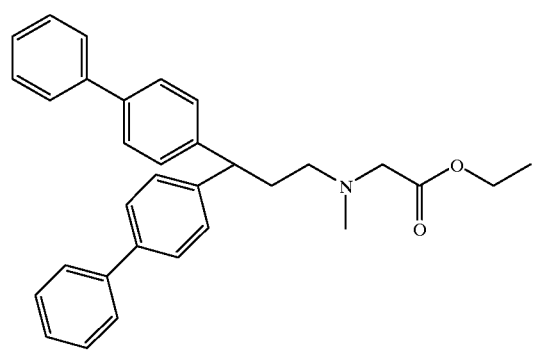
A78 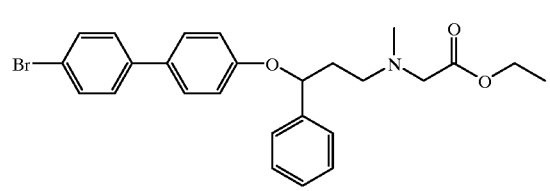
A79 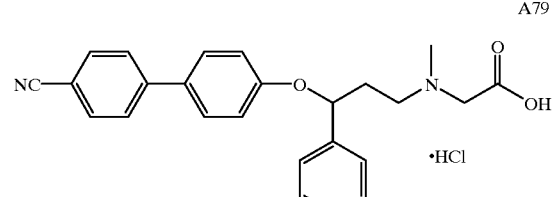
A80 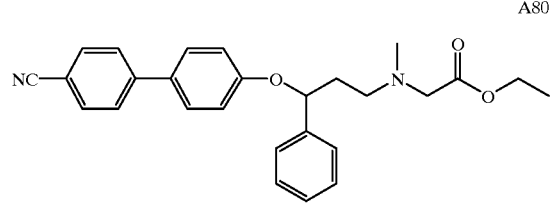
A81 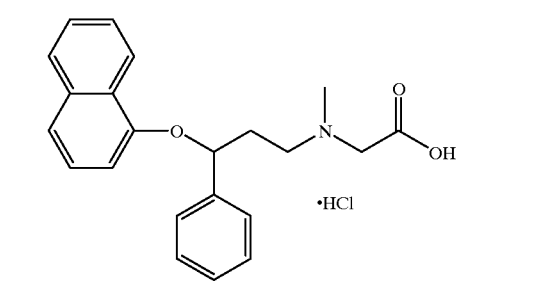
A82 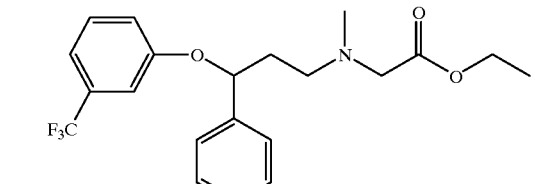
A83 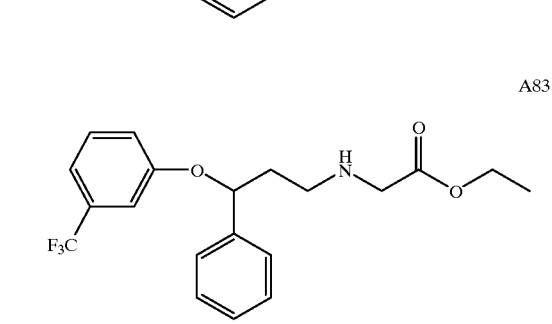

A84 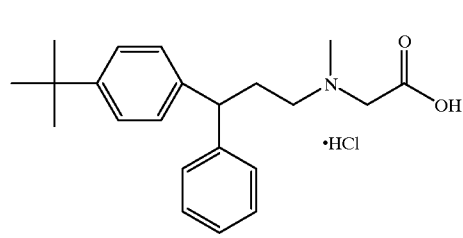
A85 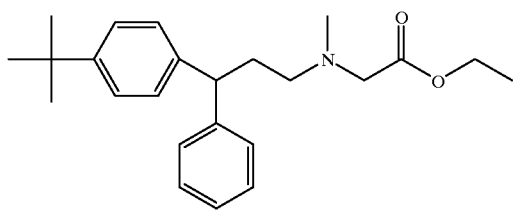
A86 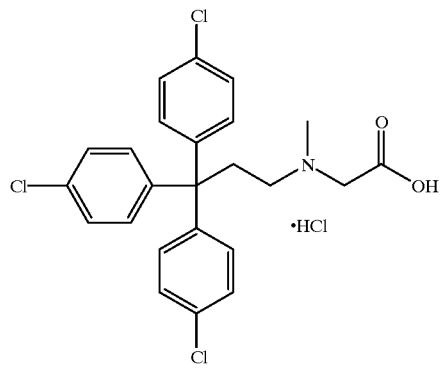
A87 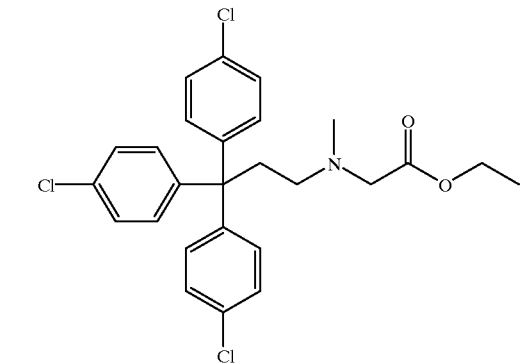
A88 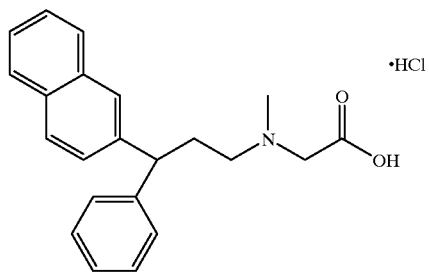
A89 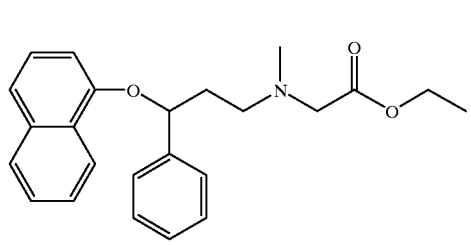
A90 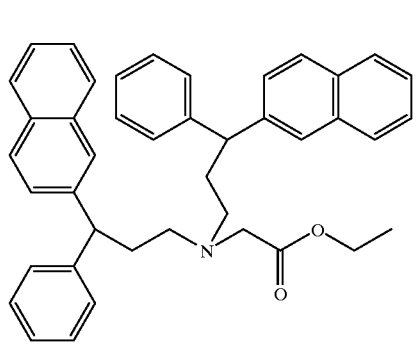
A91 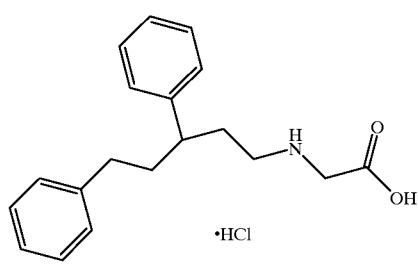
A92 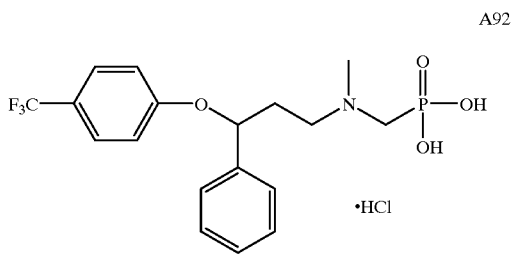
A93

A94
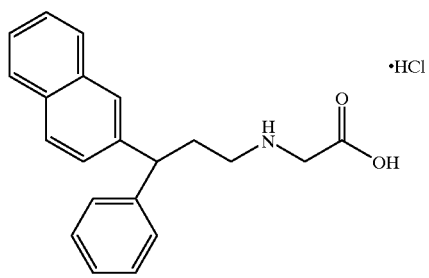
A95
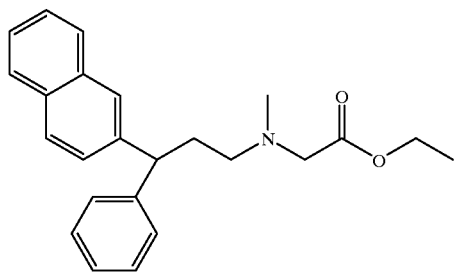
A96
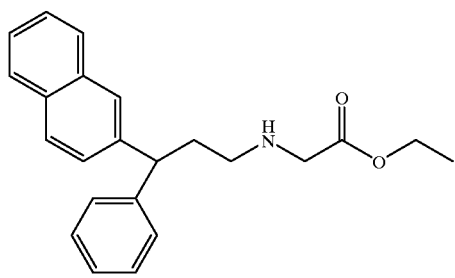
A98
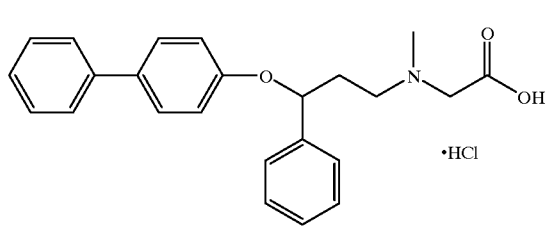
A99
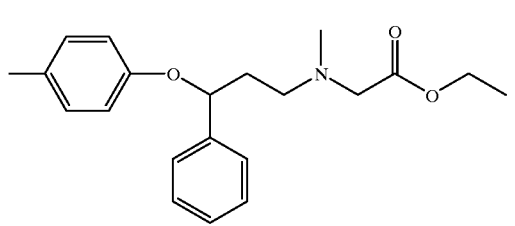
A100
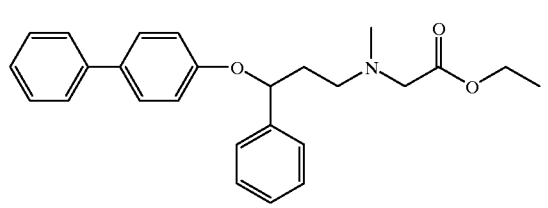
A101
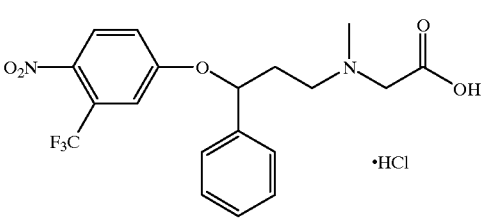
A102
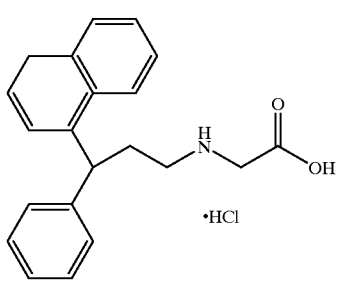
A103
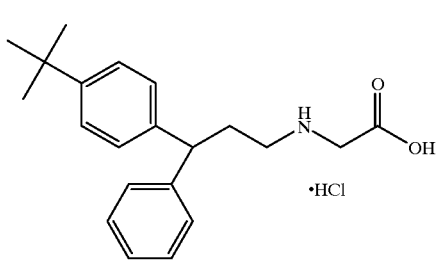
A104
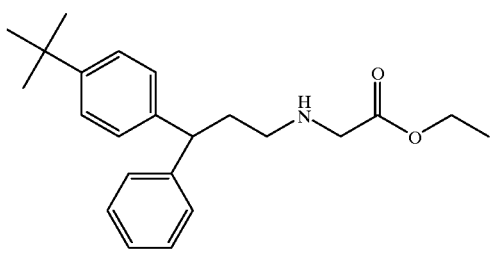
A105
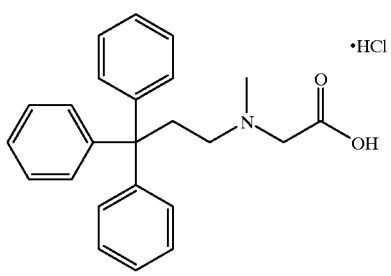

-continued
A106
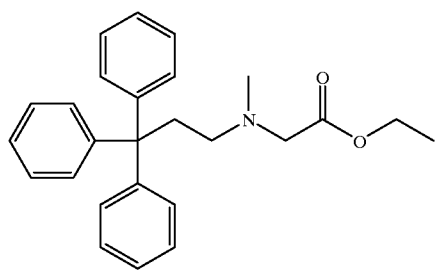
A107
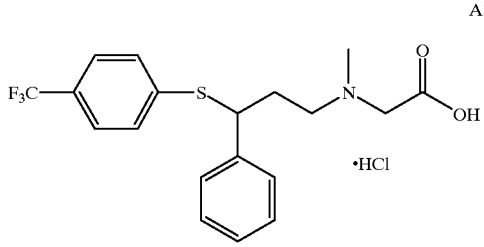
A108
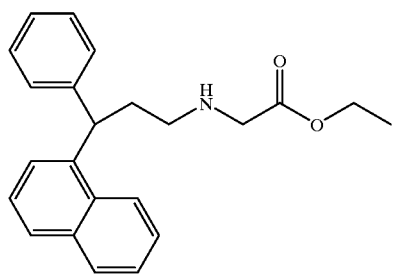
A109
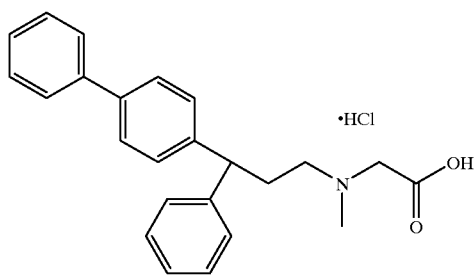
A110
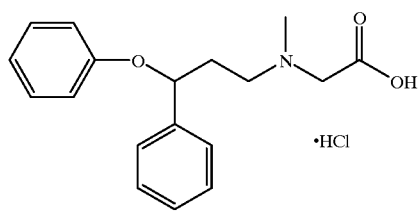
A111
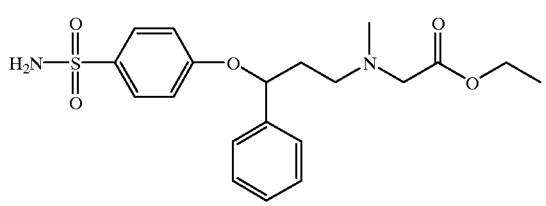
-continued
A112
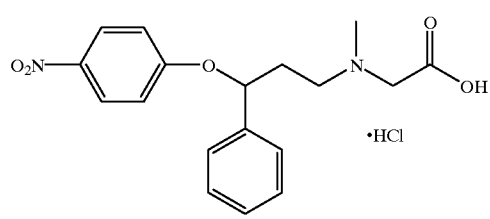
A113
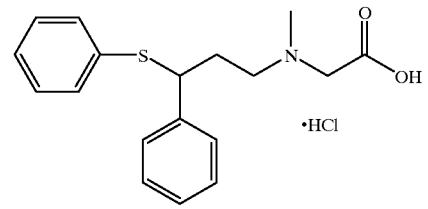
A114
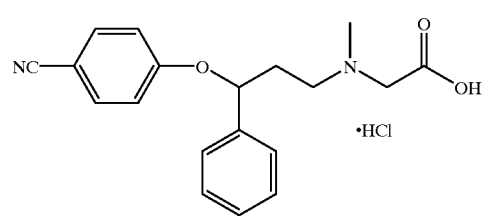
A115
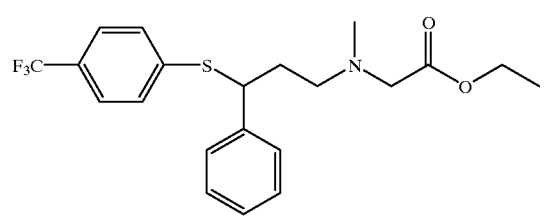
A116
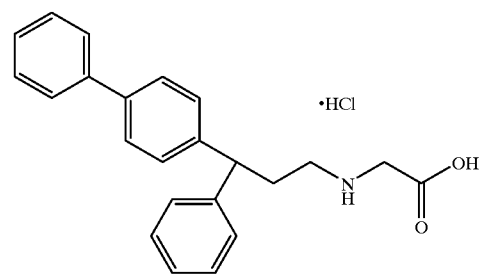
A117
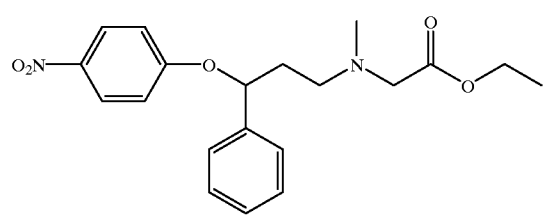

A118
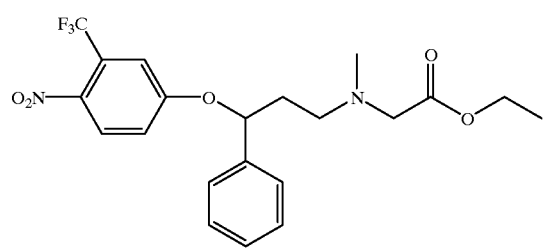
A119
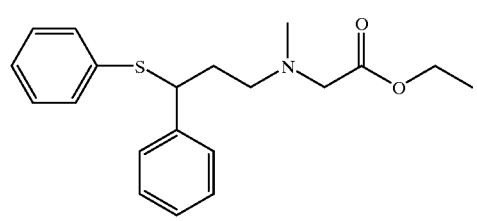
A120
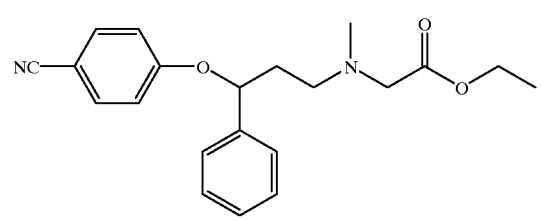
A121
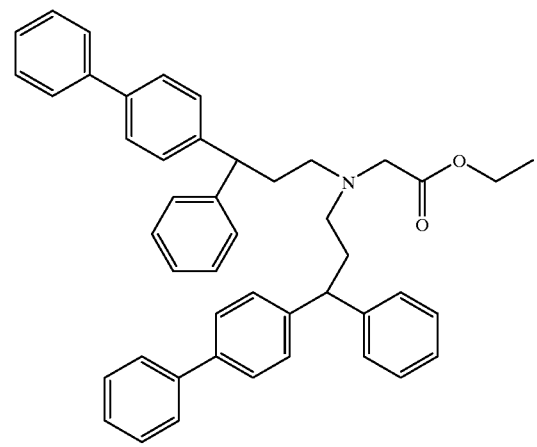
A122
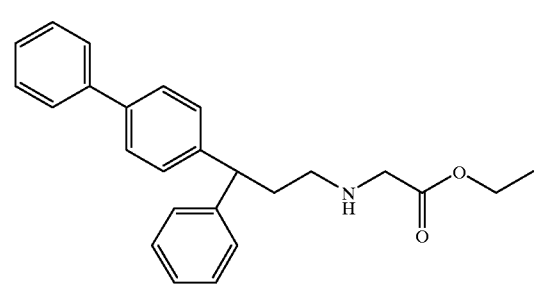
A123
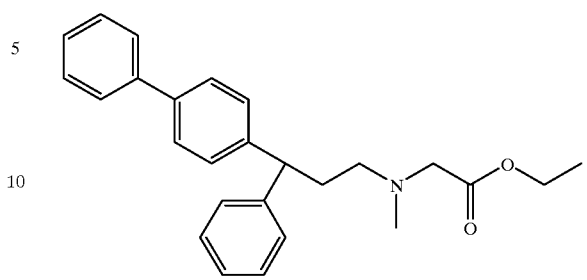
A124
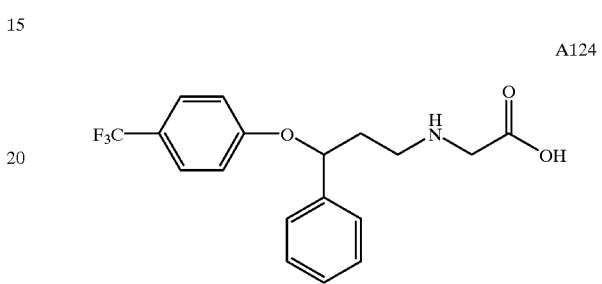
A125
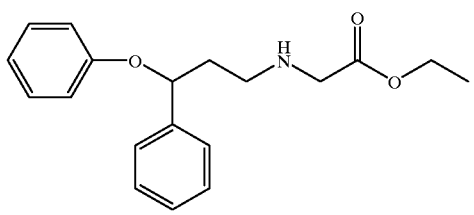
A126
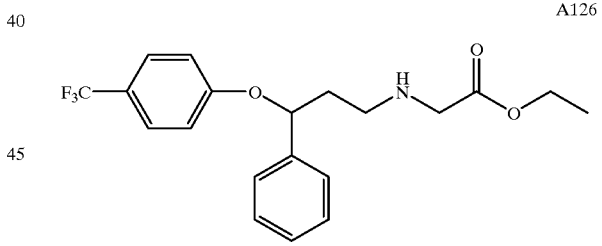
A127
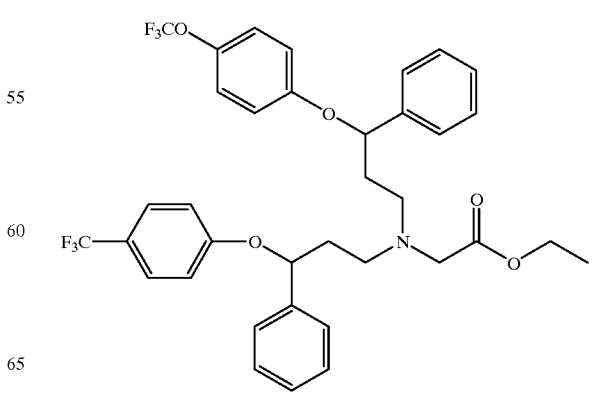

-continued
A128
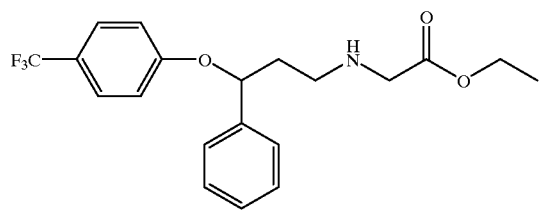
A129
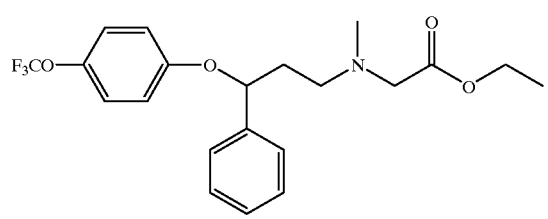
A130
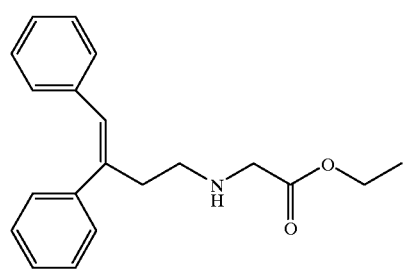
A131
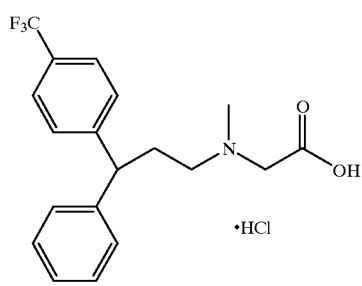
A132
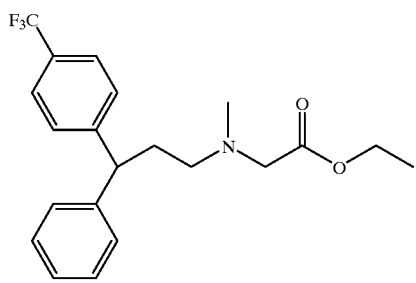
A133
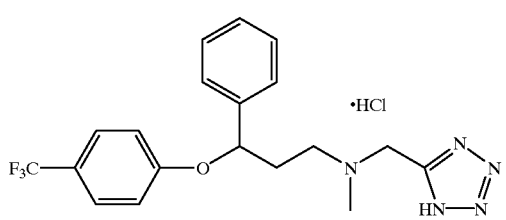
-continued
A134
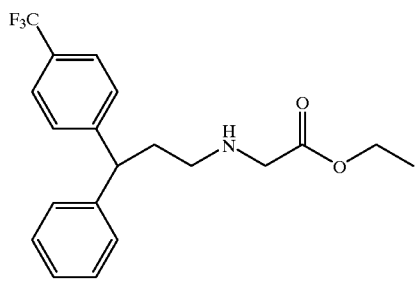
A135
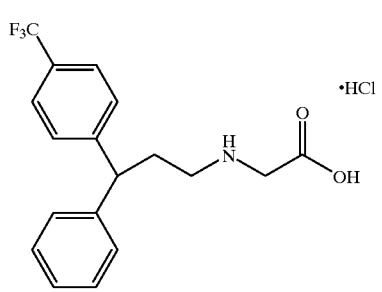
A136
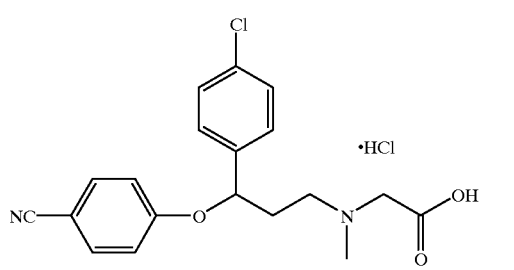
A137
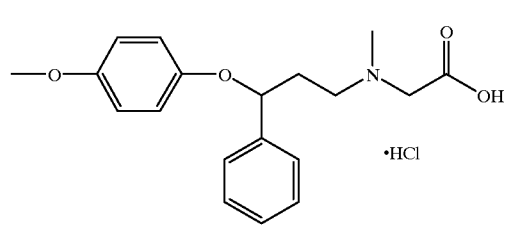
A138
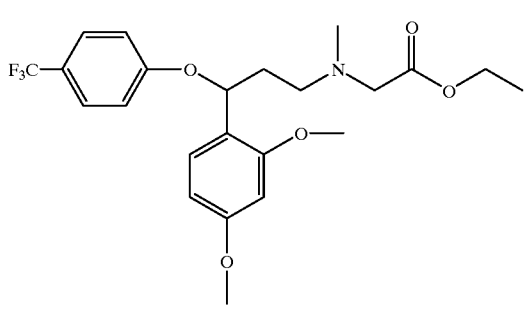

A140 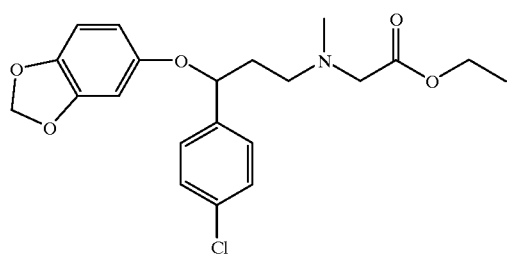
A141 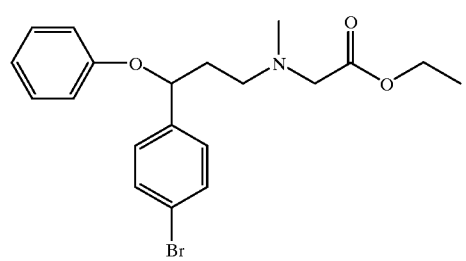
A142 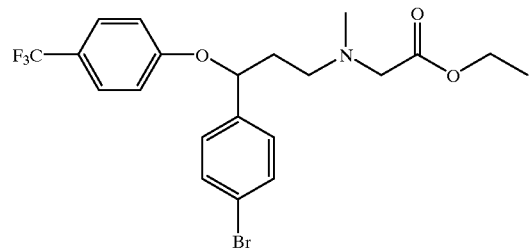
A143 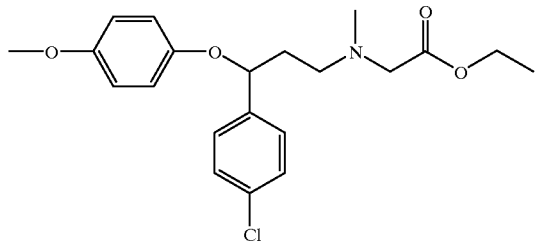
A144 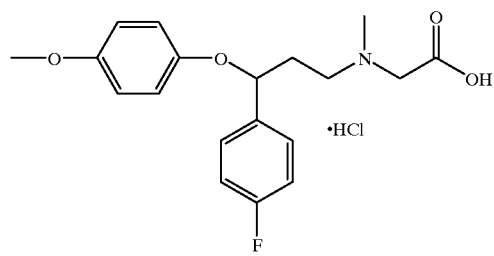
A145 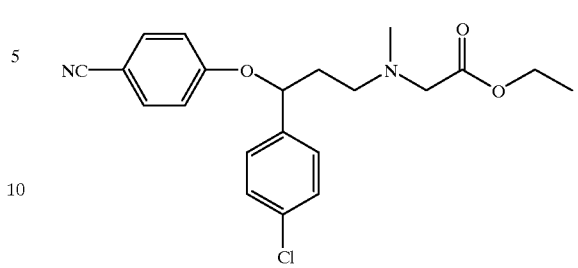
A146 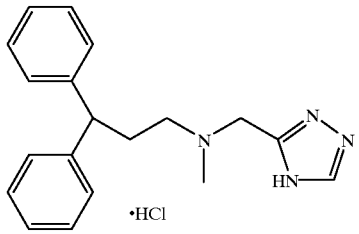
A147 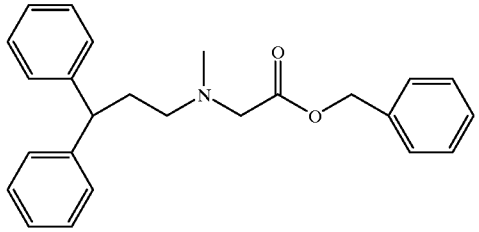
A148 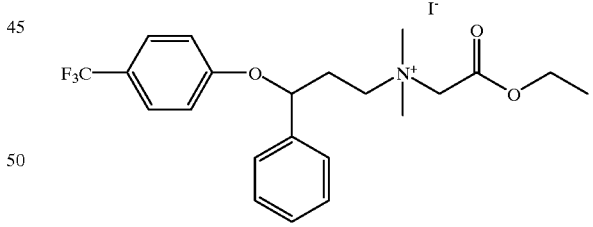
A150 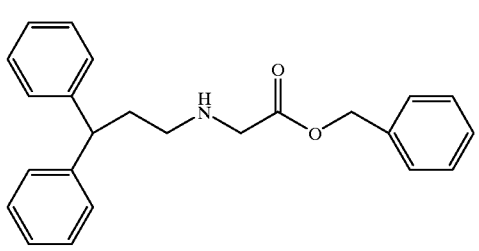

A152 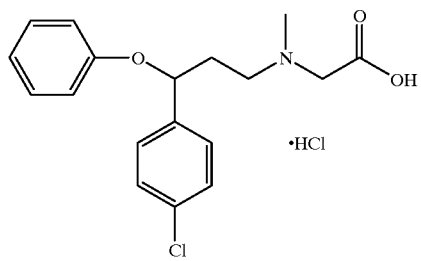
A154 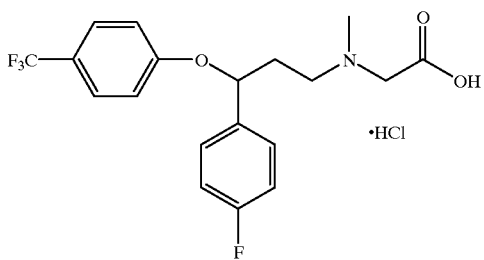
A155 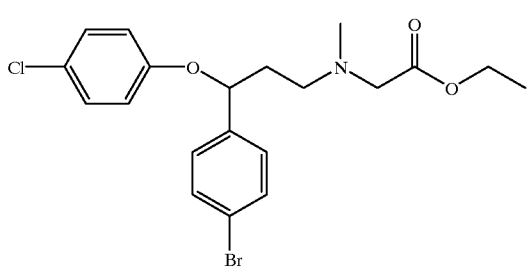
A156 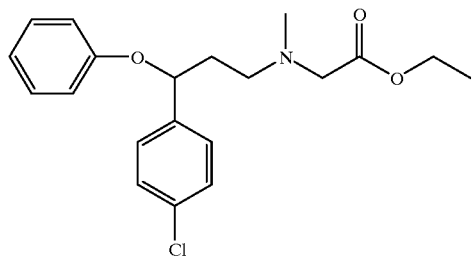
A157 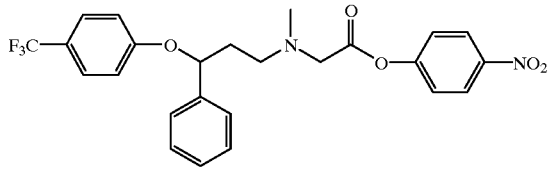
A158 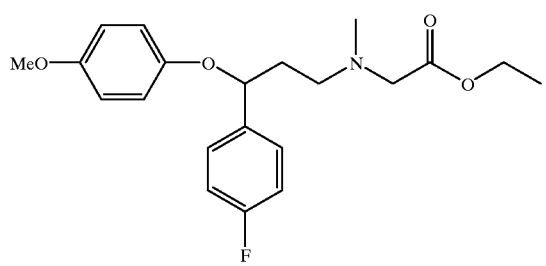
A159 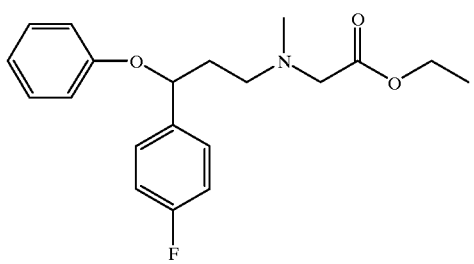
A160 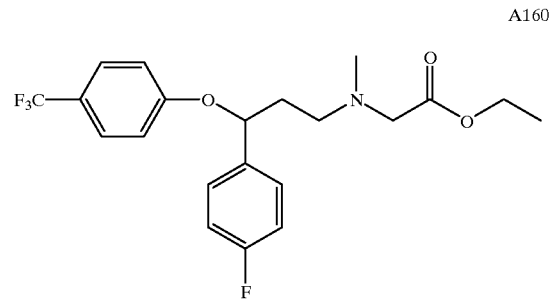
A161 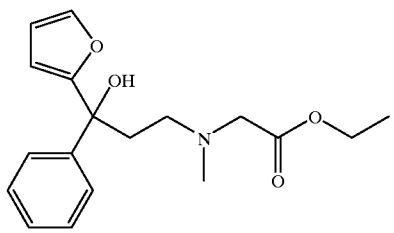
A162 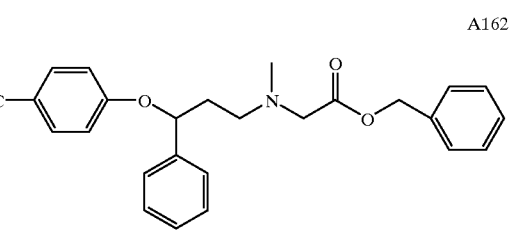
A164 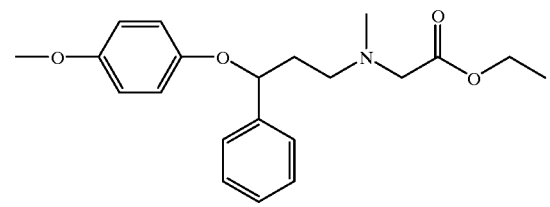
A165 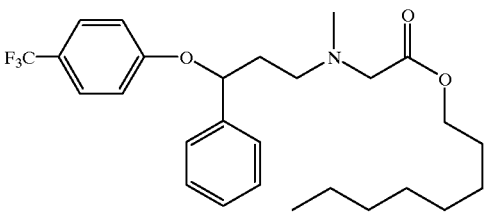

-continued
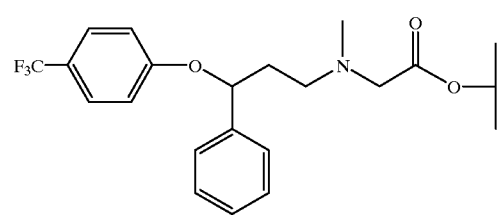
A166
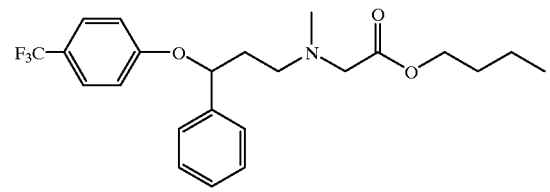
A167
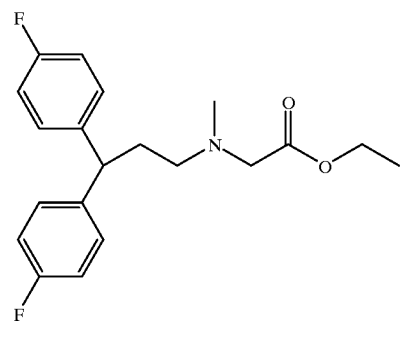
A170
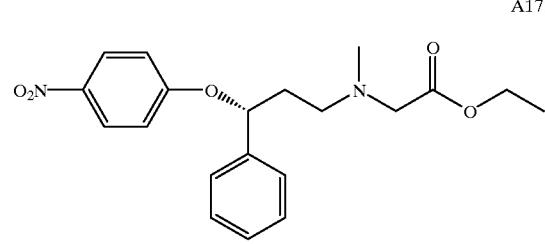
A171
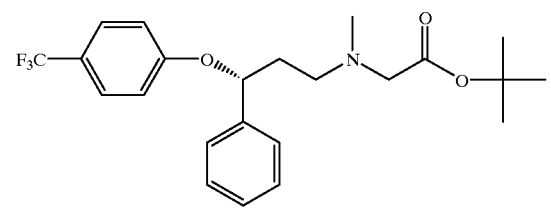
A172
-continued
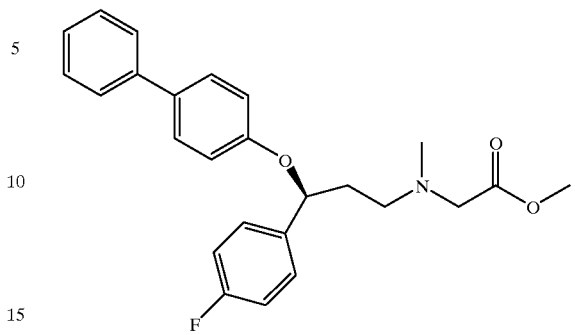
A173
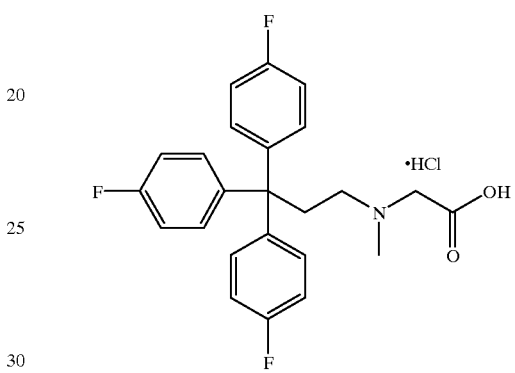
A174
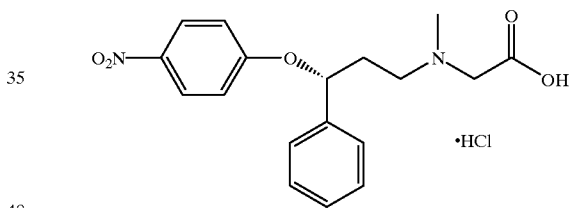
A175
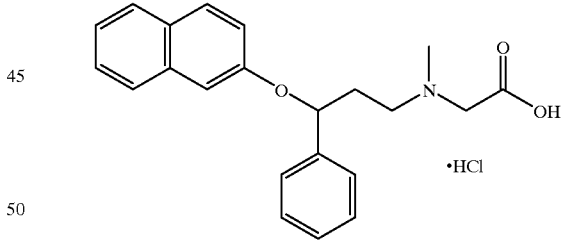
A176
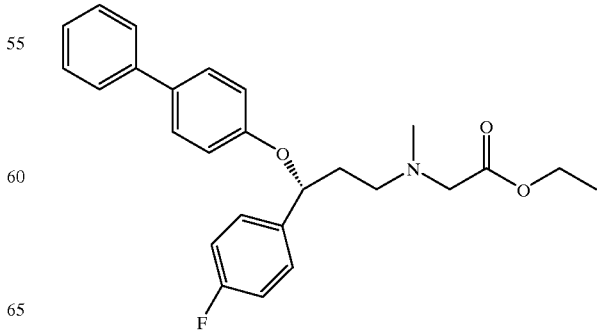
A177

A178

A179

A180

A181

A182

A183

A184

B1

-continued
B1
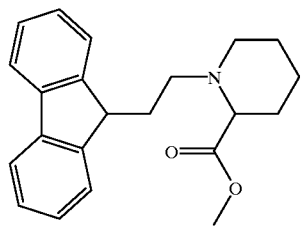
B2
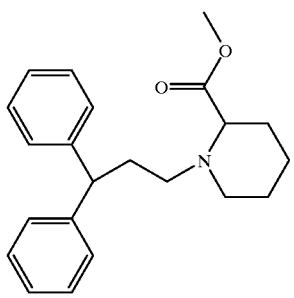
B3
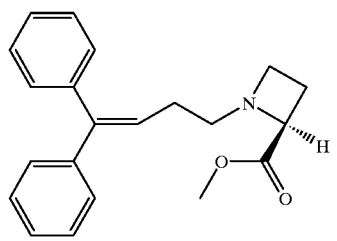
B8
B4
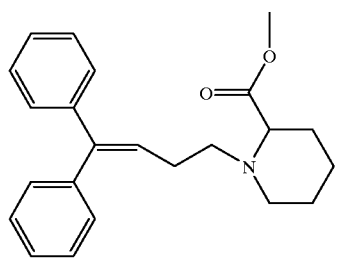
B9
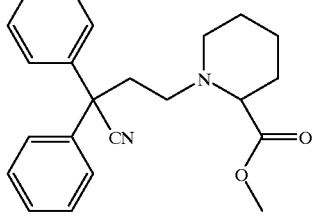
B5
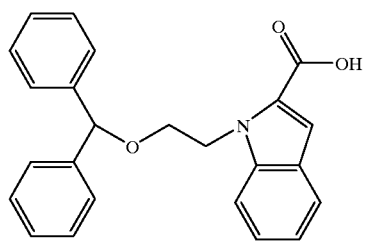
B10
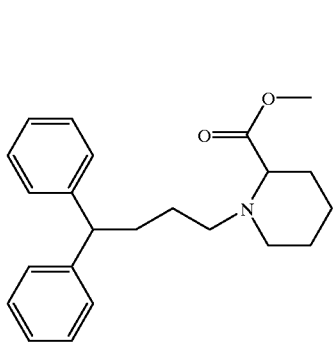
B6
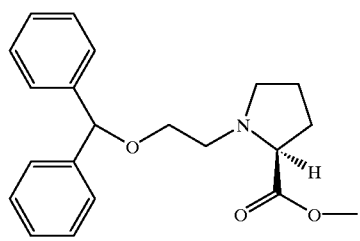
B11
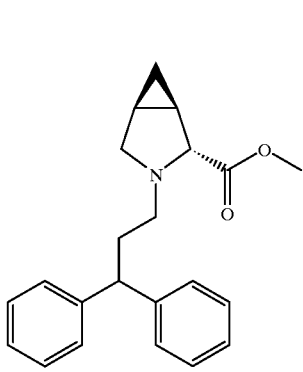
B7
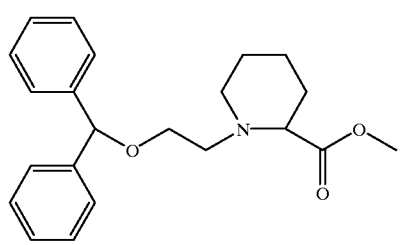
B12
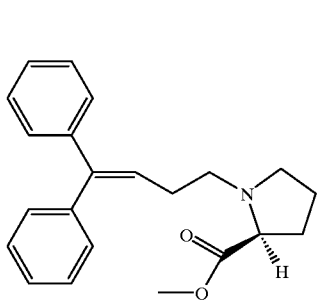

B13 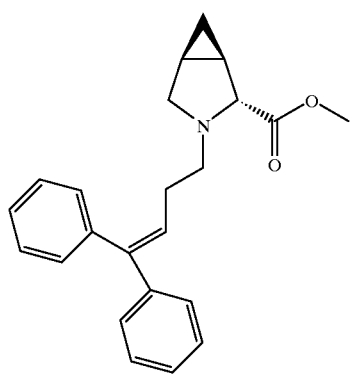
B14 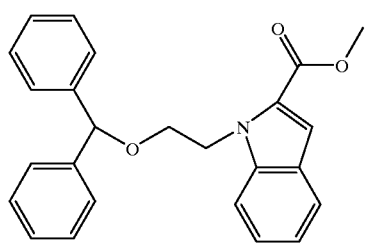
B15 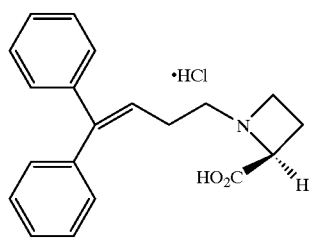
B16 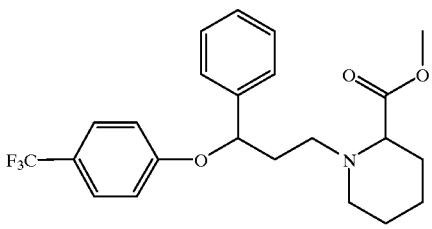
B17 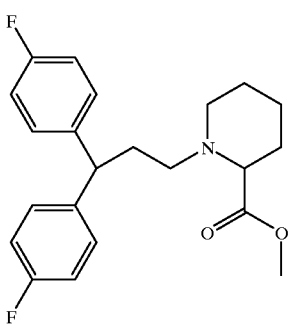
B18 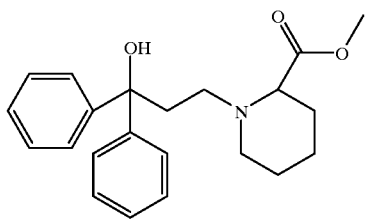
B19 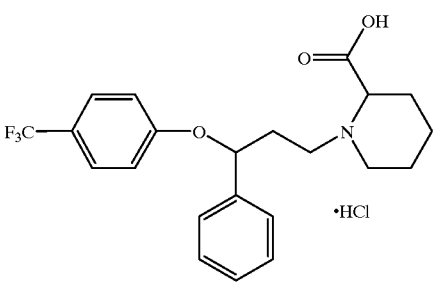
B20 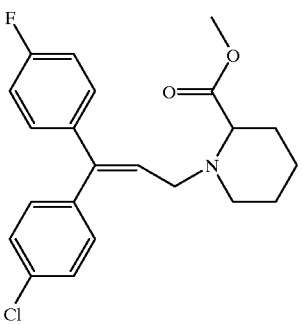
B21 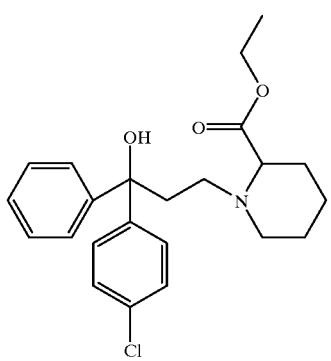
B22 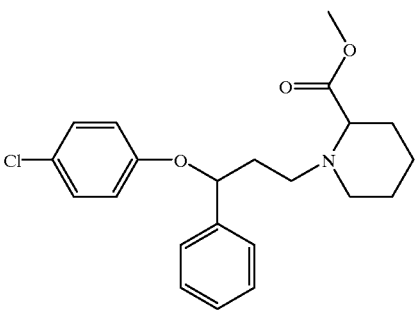

B23
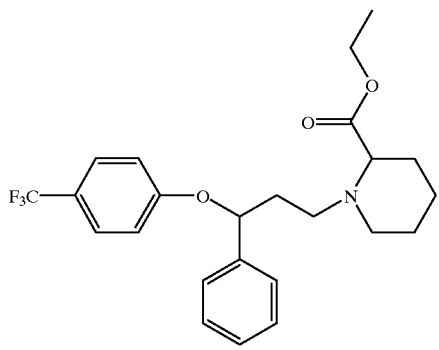

B24
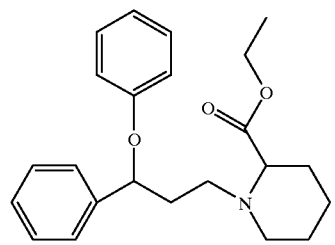

B25
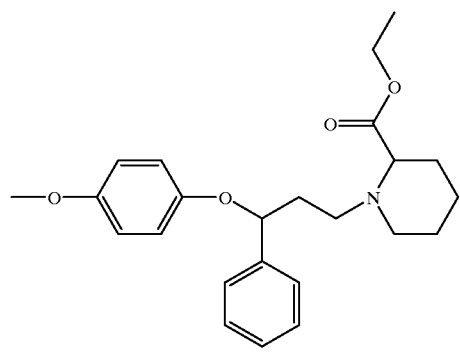

B29
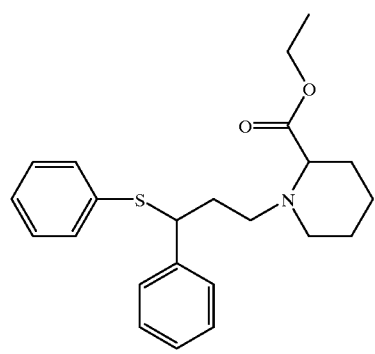

B30
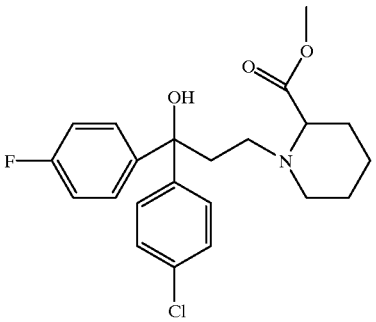

Compound A12 is a bis-alkylation byproduct of the synthesis of A9 using reaction I.

The compounds of the invention that incorporate =N—O— can be prepared, for example, by alkylating an amine (such as sarcosine or glycine) with O-(2-halogenethyl)alkanone oximes, which can be prepared by condensing alkanones with hydroxylamine, followed by O-alkylation (such as with 1,2-dihaloethane).

It will be recognized that numerous salt forms of the compounds herein described are available and suitable for use in the invention or during the synthesis of compounds of the invention. The invention contemplates that in certain instances where stereoisomers are available that one such isomer can be more active than another; in such a case, it will be desirable to isolate the particular isomeric form. The invention, of course, encompasses both the particular stereoisomers and racemic mixtures. As described herein, chemical approaches, starting with for example commercially available, optically pure starting materials (or made using enantioselective reactions), can also used to synthesize optically pure versions of the compounds of the invention. It will be recognized that such optically pure compounds are within the invention. Enantiomeric excess ("ee") can be enhanced by purification techniques such as crystallization or chromatography on chiral supports. Enantiomeric excess can be quantitated by a number of analytic techniques including NMR, optical rotation measures and appropriate chromatography.

Additional, related compounds are described in two U.S. patent applications were filed concurrently with a parent hereof as U.S. Ser. No. 08/655,912 (Ognyanov et al.), U.S. Ser. No. 08/655,847 (Ognyanov et al.), U.S. Ser. No. 08/808,755 (PHARMACEUTICAL FOR TREATMENT OF NEUROPSYCHIATRIC AND NEUROLOGICAL DISORDERS, Ognyanov et al.) and U.S. Ser. No. 08/807,681 (PHARMACEUTICAL FOR TREATING OF NEUROLOGICAL AND NEUROPSYCHIATRIC DISORDERS, Ognyanov et al.), which applications are also incorporated herein by reference in their entirety. Further incorporated by reference in its entirety are U.S. application Ser. No. 08/655,912 (Ognyanov et al.) and are U.S. application Ser. No. 08/808,754 (Ognyanov et al.) the parents of the present application.

In a preferred embodiment, at least one of the following applies:

if $R^{15}$ is hydrogen and $R^1$ is propylene, then at least one [preferably at least two, more preferably at least three] of the following applies (1) both $R^x$ and $R^y$ are not p-fluorophenyl, (2) one of $R^x$ and $R^y$ includes a heteroaryl, (3) $R^y$ is arylalkyl, heteroarylalkyl, aryloxy, heteroaryloxy, arylmethoxy, heteroarylmethoxy, arylthio, heteroarylthio, arylmethylthio, heteroarylmethylthio, Ar—N($R^6$)— or Ar—CH$_2$—N($R^{6*}$)—, (4) $R^2$ is $R^{xa}$ $R^{xb}$—, (5) $R^{2*}$ is not hydrogen, (6) $R^3$ is not hydrogen, (7) n is one, or (8) $R^3$ and $R^4$ form ring Q;

if $R^{15}$ is hydrogen and $R^1$ is ethylene or X—$R^1$ is prop-1-enylene, then at least one [preferably at least two, more preferably at least three] of the following applies (1) an aryl of at least one of $R^x$ and $R^y$ is substituted with a radical different from hydrogen, (2) one of $R^x$ and $R^y$ comprises a heteroaryl, (3) $R^y$ is arylalkyl, heteroarylalkyl, aryloxy, heteroaryloxy, arylmethoxy, heteroarylmethoxy, arylthio, heteroarylthio, arylmethylthio, heteroarylmethylthio, Ar—N($R^6$)— or Ar—CH$_2$—N($R^{6*}$)—, (4) $R^2$ is $R^{xa}$ $R^{xb}$—, (5) $R^{2*}$ is not hydrogen, (6) $R^3$ is not hydrogen, (7) n is one, or (8) $R^3$ and $R^4$ form ring Q;

if $R^5$ is C(O)NH$_2$, then at least one [preferably at least two, more preferably at least three] of the following applies (1) an aryl of at least one of $R^x$ and $R^y$ is substituted with a radical different from hydrogen, (2) one of $R^x$ and $R^y$ comprises a heteroaryl, (3) $R^y$ is arylalkyl, heteroarylalkyl, aryloxy, heteroaryloxy, arylmethoxy, heteroarylmethoxy, arylthio, heteroarylthio, arylmethylthio, heteroarylmethylthio, Ar—N($R^6$)— or Ar—CH$_2$—N($R^{6*}$)—, (4) $R^2$ is $R^{xa}$ $R^{xb}$—, (5) $R^{2*}$ is not hydrogen, (6) $R^3$ is not hydrogen, (7) n is one, (8) $R^1$ is not ethylene, or (9) $R^3$ and $R^4$ form ring Q;

if $R^{13}$ is hydrogen and $R^{14}$ is (3,4-dihydro-2H-1-benzopyran-4-yl)methylene, then at least one [preferably at least two, more preferably at least three] of the following applies (1) an aryl of at least one of $R^x$ and $R^y$ is substituted with a radical different from hydrogen, (2) one of $R^x$ and $R^y$ comprises a heteroaryl, (3) $R^y$ is arylalkyl heteroarylalkyl, aryloxy, heteroaryloxy, arylmethoxy, heteroarylmethoxy, arylthio, heteroarylthio, arylmethylthio, heteroarylmethylthio, Ar—N($R^6$)— or Ar—CH$_2$—N($R^{6*}$)—, (4) $R^2$ is $R^{xa}$ $R^{xb}$—, (5) $R^{2*}$ is not hydrogen, (6) $R^3$ is not ethyl, (7) n is one, or (8) $R^3$ and $R^4$ form ring Q; and if $R^2$ is phenyl, p-methylphenyl or p-methoxyphenyl, then at least one [preferably at least two, more preferably at least three] of the following applies (1) the aryls of $R^x$ and $R^y$ are not substituted with p-methylphenyl or p-methoxyphenyl, (2) an aryl of at least one of $R^x$ and $R^y$ is substituted with a radical different from hydrogen, (3) one of $R^x$ and $R^y$ comprises a heteroaryl, (4) $R^y$ is arylalkyl, heteroarylalkyl, aryloxy, heteroaryloxy, arylmethoxy, heteroarylmethoxy, arylthio, heteroarylthio, arylmethylthio, heteroarylmethylthio, Ar—N($R^6$)— or Ar—CH$_2$—N($R^{6*}$)—, (5) $R^1$ is not aminoethylene, O$R^8$ or S$R^{8*}$, (6) n is one, or (7) $R^3$ and $R^4$ form ring Q.

In one preferred embodiment of the the methods, particularly treating or preventing epilepsy or spasticity or enhancing memory, the compound conforms with paragraph (f), above.

The glycine transporter genes and their respective gene products are responsible for the reuptake of glycine from the synaptic cleft into presynaptic nerve endings or glial cells, thus terminating the action of glycine. Neurological disorders or conditions associated with improperly controlled glycine receptor activity, or which could be treated with therapeutic agents that modulate glycine receptor activity, include spasticity (Becker, *FASEB Journal*, 4, 2767–2774 (1990)) and pain realization (Yaksh, *Pain*, 37, 111–123 (1989)). Additionally, glycine interacts at N-methyl-D-aspartate (NMDA) receptors, which have been implicated in learning and memory disorders and certain clinical conditions such as epilepsy, Alzheimer's and other cognition-related diseases, and schizophrenia. See Rison and Stanton, *Neurosci. Biobehav. Rev.*, 19, 533–552 (1995); Danysz et al., *Behavioral Pharmacol.*, 6, 455–474 (1995).

Compounds that inhibit GlyT-1 mediated glycine transport will increase glycine concentrations at NMDA receptors, which receptors are located in the forebrain, among other locations. This concentration increase elevates the activity of NMDA receptors, thereby alleviating schizophrenia and enhancing cognitive function. Alternatively, compounds that interact directly with the glycine receptor component of the NMDA receptor can have the same or similar effects as increasing or decreasing the availability of extracellular glycine caused by inhibiting or enhancing GlyT-1 activity, respectively. See, for example, Pitkänen et al., *Eur. J. Pharmacol.*, 253, 125–129 (1994); Thiels et al., *Neuroscience*, 46, 501–509 (1992); and Kretschmer and Schmidt, *J. Neurosci.*, 16, 1561–1569 (1996). Compounds that inhibit GlyT-2 mediated glycine transport will increase glycine concentrations at receptors located primarily in the brain stem and spinal cord, where glycine acts as an inhibitor of synaptic transmission. These compounds are effective against epilepsy, pain and spasticity, myospasm and other such conditions. See, for example, Becker, *FASEB J.* 4, 2767–2774 (1990) and Yaksh, *Pain*, 37, 111–123 (1989).

The compounds of the invention are, for instance, administered orally, sublingually, rectally, nasally, vaginally, topically (including the use of a patch or other transdermal delivery device), by pulmonary route by use of an aerosol, or parenterally, including, for example, intramuscularly, subcutaneously, intraperitoneally, intraarterially, intravenously or intrathecally. Administration can be by means of a pump for periodic or continuous delivery. The compounds of the invention are administered alone, or are combined with a pharmaceutically-acceptable carrier or excipient according to standard pharmaceutical practice. For the oral mode of administration, the compounds of the invention are used in the form of tablets, capsules, lozenges, chewing gum, troches, powders, syrups, elixirs, aqueous solutions and suspensions, and the like. In the case of tablets, carriers that are used include lactose, sodium citrate and salts of phosphoric acid. Various disintegrants such as starch, and lubricating agents such as magnesium stearate and talc, are commonly used in tablets. For oral administration in capsule form, useful diluents are lactose and high molecular weight polyethylene glycols. If desired, certain sweetening and/or flavoring agents are added. For parenteral administration, sterile solutions of the compounds of the invention are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchromium chloride, and the usual quantities of diluents and/or carriers. For pulmonary administration, diluents and/or carriers will be selected to be appropriate to allow the formation of an aerosol.

Suppository forms of the compounds of the invention are useful for vaginal, urethral and rectal administrations. Such suppositories will generally be constructed of a mixture of substances that is solid at room temperature but melts at body temperature. The substances commonly used to create such vehicles include theobroma oil, glycerinated gelatin, hydrogenated vegetable oils, mixtures of polyethylene glycols of various molecular weight and fatty acid esters of polyethylene glycol. See, Remington's Pharmaceutical Sciences, 16th Ed., Mack Publishing, Easton, Pa., 1980, pp. 1530–1533 for further discussion of suppository dosage forms. Analogous gels or cremes can be used for vaginal, urethral and rectal administrations.

Numerous administration vehicles will be apparent to those of ordinary skill in the art, including without limitation slow release formulations, liposomal formulations and polymeric matrices.

Examples of pharmaceutically acceptable acid addition salts for use in the present invention include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic and arylsulphonic acids, for example. Examples of pharmaceutically acceptable base addition salts for use in the present invention include those derived from non-toxic metals such as sodium or potassium, ammonium salts and organoamino salts such as triethylamine salts. Numerous appropriate such salts will be known to those of ordinary skill.

The physician or other health care profesional can select the appropriate dose and treatment regimen based on the subjects weight, age, and physical condition. Dosages will generally be selected to maintain a serum level of compounds of the invention between about 0.01 µg/cc and about 1000 µg/cc, preferably between about 0.1 µg/cc and about 100 µg/cc. For parenteral administration, an alternative measure of preferred amount is from about 0.001 mg/kg to about 10 mg/kg (alternatively, from about 0.01 mg/kg to about 10 mg/kg), more preferably from about 0.01 mg/kg to about 1 mg/kg (from about 0.1 mg/kg to about 1 mg/kg), will be administered. For oral administrations, an alternative measure of preferred administration amount is from about 0.001 mg/kg to about 10 mg/kg (from about 0.1 mg/kg to about 10 mg/kg), more preferably from about 0.01 mg/kg to about 1 mg/kg (from about 0.1 mg/kg to about 1 mg/kg). For administrations in suppository form, an alternative measure of preferred administration amount is from about 0.1 mg/kg to about 10 mg/kg, more preferably from about 0.1 mg/kg to about 1 mg/kg.

For use in assaying for activity in inhibiting glycine transport, eukaryokic cells, preferably QT-6 cells derived from quail fibroblasts, have been transfected to express one of the three known variants of human GlyT-1, namely GlyT-1a, GlyT-1b or GlyT-1c, or human GlyT-2. The sequences of these GlyT-1 transporters are described in Kim et al., *Molec. Pharm.* 45: 608–617, 1994, excepting that the sequence encoding the extreme N-terminal of GlyT-1a was merely inferred from the corresponding rat-derived sequence. This N-terminal protein-encoding sequence has now been confirmed to correspond to that inferred by Kim et al. The sequence of the human GlyT-2 is described by Albert et al., U.S. application Ser. No. 08/700,013, filed Aug. 20, 1996, which is incorporated herein by reference in its entirety. Suitable expression vectors include pRc/CMV (Invitrogen), Zap Express Vector (Stratagene Cloning Systems, LaJolla, Calif.; hereinafter "Stratagene"), pBk/CMV or pBk-RSV vectors (Stratagene), Bluescript II SK+/− Phagemid Vectors (Stratagene), LacSwitch (Stratagene), pMAM and pMAM neo (Clontech), among others. A suitable expression vector is capable of fostering expression of the included GlyT DNA in a suitable host cell, preferably a non-mammalian host cell, which can be eukaryotic, fungal, or prokaryotic. Such preferred host cells include amphibian, avian, fungal, insect, and reptilian cells.

As discussed above, the compounds of the invention have a number of pharmacological actions. The relative effectiveness of the compounds can be assessed in a number of ways, including the following:

comparing the activity mediated through GlyT-1 and GlyT-2 transporters. This testing identifies compounds (a) that are more active against GlyT-1 transporters and thus more useful in treating or preventing schizophrenia, increasing cognition and enhancing memory or (b) that are more active against GlyT-2 transporters and thus more useful in treating or preventing epilepsy, pain, spasticity or myospasm.

testing for NMDA receptor binding. This test establishes whether there is sufficient binding at this site, whether antagonist or agonist activity, to warrant further examination of the pharmacological effect of such binding.

testing the activity of the compounds in enhancing or diminishing calcium fluxes in primary neuronal tissue culture. A test compound that increases calcium flux either (a) has little or no antagonist activity at the NMDA receptor and should not affect the potentiation of glycine activity through GlyT-1 transporter inhibition or (b), if marked increases are observed over GlyT-1 inhibitors used for comparison and that have little direct interaction with NMDA receptors, then the compound is a receptor agonist. In either of the above-described cases, the test confirms activity in treating or preventing schizophrenia, increasing cognition, or enhancing memory. In contrast, a test compound that decreases calcium flux has a net effect wherein receptor antagonist activity predominates over any activity the compound has in increasing glycine activity through inhibiting glycine transport. In this case, the test confirms activity in limiting or preventing the cell damage and cell death arising after stroke or other ischemia-inducing conditions, or in limiting or preventing the cell damage associated with neurodegenerative diseases.

All animal methods of treatment or prevention described herein are preferably applied to mammals, most preferably humans.

The following examples further illustrate the present invention, but of course, should not be construed as in any way limiting its scope.

EXAMPLE 1

Synthesis of N-[(4,4-Diphenyl)but-3-enyl]glycine Ethyl Ester (Compound A26)

A mixture of 5.95 g (20.7 mmol) 4-bromo-1,1-diphenyl-1-butene (prepared as described in F. A. Ali et al., *J. Med. Chem.* 28: 653–660, 1985), 4.71 g (33.7 mmol) glycine ethyl ester hydrochloride (Aldrich, Milwaukee, Wis.), 11.62 g (84 mmol) potassium carbonate and 1.06 g (6.38 mmol) potassium iodide in 50 ml acetonitrile was refluxed with stirring under argon for seven hours. The reaction mixture was filtered, the solvent evaporated and the residue chromatographed on silica gel column with 20% ethyl acetate in hexanes to give 3.70 g (yield 58%) of N-[(4,4-diphenyl)but-3-enyl]glycine ethyl ester (compound A26) as an oil. NMR spectra of the product showed: $^1$H NMR (CDCl$_3$, 300 MHz)

7.60–7.00 (m, 10 H), 6.09 (t, 1 H), 4.16 (q, 2 H), 3.35 (s, 2 H), 2.71 (t, 2 H), 2.32 (dt, 2 H), 1.25 (t, 3 H), $^{13}$C NMR (CDCl$_3$, 75 MHz) 172.29, 143.25, 142.37, 139.82, 129.72, 128.13, 128.04, 127.97, 127.13, 126.92, 126.88, 126.68, 60.56, 50.73, 49.32, 30.33, 14.14.

EXAMPLE 2

Additional Syntheses According to Reaction 1

Additional compounds were synthesized using Reaction 1, as follows:

| Compound | Reagent | Amino acid or precusor | Solvent | Yield |
|---|---|---|---|---|
| A1 | 1 | B | X | 27% |
| A2 | 1 | C | X | 35% |
| A7 | 7 | E | X | 9% |
| A9 | 4 | E | X | 47% |
| A11 | 1 | A | X | 70% |
| A12 | 4 | E | X | 7% |
| A14 | 2 | D | X | 15% |
| A18 | 6 | E | X | 50% |
| A23 | 5 | E | X | 26% |
| A24 | 3 | D | Y | 20% |
| A43 | 8 | F | X | 12% |
| A52 | 9 | F | X | 28% |
| A57 | 10 | F | X | 31% |
| A67 | 11 | F | X | 10% |
| A71 | 12 | E | X | 28% |
| A75 | 13 | F | X | 73% |
| A77 | 14 | F | X | 36% |
| A85 | 15 | F | X | 86% |
| A87 | 16 | F | X | 59% |
| A90 | 17 | E | X | 16% |
| A95 | 17 | F | X | 65% |
| A96 | 17 | E | X | 50% |
| A104 | 15 | E | X | 62% |
| A106 | 18 | F | X | 65% |
| A121 | 19 | E | X | 3% |
| A122 | 19 | E | X | 40% |
| A123 | 19 | F | X | 72% |
| A130 | 20 | E | X | 6% |
| A132 | 21 | F | X | 90% |
| A134 | 21 | E | X | 67% |
| A170 | 6 | F | X | 72% |
| A48 | 22 | F | x | 87% |
| A50 | 23 | F | X | 81% |
| A53 | 24 | F | X | 76% |
| A59 | 25 | F | X | 77% |
| A61 | 26 | F | X | 91% |
| A63 | 27 | F | X | 91% |
| A70 | 28 | F | X | 89% |
| A73 | 29 | F | X | 86% |
| A74 | 30 | F | X | 76% |
| A78 | 31 | F | X | 49% |
| A80 | 32 | F | X | 66% |
| A82 | 33 | F | X | 38% |
| A83 | 33 | E | X | 25% |
| A88 | 34 | F | X | 55% |
| A89 | 35 | F | X | 75% |
| A99 | 36 | F | X | 56% |
| A100 | 37 | F | X | 67% |
| A111 | 38 | F | X | 34% |
| A117 | 39 | F | X | 58% |
| A118 | 40 | F | X | 89% |
| A120 | 41 | F | X | 62% |
| A125 | 42 | F | X | 46% |
| A126 | 43 | E | X | 57% |
| A127 | 44 | E | X | 5% |
| A128 | 44 | E | X | 53% |
| A129 | 44 | F | X | 66% |
| A138 | 45 | F | X | 48% |
| A140 | 46 | F | X | 69% |
| A141 | 47 | F | X | 51% |
| A142 | 48 | F | X | 67% |
| A143 | 49 | F | X | 61% |
| A145 | 50 | F | X | 98% |
| A155 | 51 | F | X | 70% |
| A156 | 52 | F | X | 65% |
| A158 | 53 | F | X | 59% |
| A159 | 54 | F | X | 85% |
| A160 | 55 | F | X | 87% |
| A171 | 56 | F | X | 88% |
| A173 | 57 | F | X | 81% |
| A177 | 58 | F | X | 84% |
| A178 | 58 | F | X | 60% |
| A179 | 59 | F | X | 68% |
| A180 | 24 | G | X | 85% |

Reagent: 1) 4-bromo-1,1-diphenyl-1-butene, (prepared as described in F. A. Ali et al., *J. Med. Chem.*, 28: 653–660, 1985); 2) 1,1'-(4-chlorobutylidene)bis(4-fluorobenzene), (Acros Organics, Pittsburgh, Pa.); 3) benzhydryl 2-bromoethyl ether, (prepared as described in M. R. Pavia et al., *J. Med. Chem.* 35: 4238–4248, 1992); 4) 9-fluorenylethanol p-toluenesulfate, [prepared by LiAlH$_4$ reduction of 9-fluoreneacetic acid methyl ester (Aldrich) to 2-(9-fluorenyl)ethanol, followed by tosylation[; 5) 4-bromo-2,2-diphenyl butyronitrile (Aldrich); 6) 3-bis(4-fluorophenyl)propanol p-toluenesulfate [prepared by alkylation of diethyl malonate (Aldrich) with chlorobis(4-fluorophenyl)methane (Aldrich) followed by hydrolysis and decarboxylation, LiAlH$_4$ reduction of the monocarboxylic acid, and tosylation of the formed alcohol]; 7) 10-(3-bromo-2-hydroxypropyl)phenothiazine [prepared essentially as described in British Patent 800,635]; 8) 3-tris(4-fluorophenyl)propanol p-toluenesulfonate prepared by alkylation of diethyl malonate (Aldrich) with 4,4',4"-trifluorotrityl bromide (TCI America, Portland, Oreg.) followed by hydrolysis and decarboxylation, LiAlH$_4$ reduction of the monocarboxylic acid, and tosylation of the formed alcohol]; 9) 3-cyclohexyl-3-phenylpropanol p-toluenesulfonate [prepared by Horner-Emmons reaction of the sodium ylide of triethyl phosphonoacetate (Aldrich) with cyclohexyl phenyl ketone (Aldrich) followed by catalytic hydrogenation of the intermediate α,β-unsaturated ester, LiAlH$_4$ reduction and tosylation of the formed alcohol]; 10) 3-tris(4-methoxyphenyl)propanol p-toluenesulfonate [prepared by alkylation of diethyl malonate (Aldrich) with 4,4',4"-trimethoxytrityl chloride (Aldrich) followed by hydrolysis and decarboxylation, LiAlH$_4$, reduction of the monocarboxylic acid, and tosylation of the formed alcohol]; 11) 3-bis(3-fluorophenyl)propanol p-toluenesulfonate prepared by Horner-Emmons reaction of the sodium ylide of triethyl phosphonoacetate (Aldrich) with 3,3'-difluorobenzophenone (Aldrich) followed by catalytic hydrogenation of the intermediate α,β-unsaturated ester, LiAlH$_4$ reduction and tosylation of the formed alcohol]; 12) 3,5-diphenylpentanol p-toluenesulfonate [prepared by Horner-Emmons reaction of the sodium ylide of triethyl phosphonoacetate (Aldrich) with 3-phenylpropiophenone (Pfaltz & Bauer Chemicals Catalog, Waterbury, Conn.) followed by catalytic hydrogenation of the intermediate α,β-unsaturated ester, LiAlH$_4$ reduction and tosylation of the formed alcohol]; 13) 3-bis (4-phenoxyphenyl)propanol p-toluenesulfonate [prepared by Homer-Emmons reaction of the sodium ylide of triethyl phosphonoacetate (Aldrich) with 4,4'-diphenoxybenzophenone (Lancaster, Windham, N.H.) followed by catalytic hydrogenation of the intermediate α,β-unsaturated ester, LiAlH$_4$ reduction and tosylation of the formed alcohol]; 14) 3-bis(4-biphenyl)propanol p-toluenesulfonate [prepared by Homer-Emmons reaction of the sodium ylide of triethyl phosphonoacetate (Aldrich) with 4-benzoylbiphenyl (Aldrich) followed by catalytic hydrogenation of the intermediate α,β-unsaturated ester, LiAlH$_4$ reduction and tosylation of the formed alcohol]; 15) 3-(4-tert-butylphenyl-3-phenypropanol p-toluenesulfonate [prepared by Homer-Emmons reaction of the sodium ylide of triethyl phosphonoacetate with 4-tert-butylbenzophenone (Aldrich) followed by catalytic hydrogenation of the intermediate α,β-unsaturated ester, LiAlH$_4$ reduction and tosylation of the formed alcohol]; 16) 3,3,3-tris(4-chlorophenyl)propanol p-toluenesulfonate [prepared by LiAlH$_4$ reduction of 3,3,3-tris(4-chloropropionic acid) (Aldrich) followed by tosylation of the formed alcohol]; 17) 3-(2-naphthyl)-3-phenyl)propanol p-toluenesulfonate [prepared by Horner-Emmons reaction of the sodium ylide of triethyl phosphonoacetate with 2-benzoylnaphthalene (Aldrich) followed by catalytic hydrogenation of the intermediate -unsaturated ester, LiAlH$_4$ reduction and tosylation of the formed alcohol); 18) 3,3,3-triphenylpropanol p-toluenesulfonate [prepared by LiAlH$_4$ reduction of 3,3,3-triphenylpropionic acid (Aldrich) followed by tosylation of the formed alcohol]; 19) 3-(4-phenylphenyl)-3-phenylpropanol p-toluenesulfonate [prepared by Homer-Emmons reaction of the sodium ylide of triethyl phosphonoacetate with 4-benzoylbiphenyl (Aldrich) followed by catalytic hydrogenation of the intermediate α,β-unsaturated ester, LiAlH$_4$ reduction and tosylation of the formed alcohol]; 20) 1,2-diphenylbutan-1,4-diol p-toluenesulfonate [prepared by C-alkylation of deoxybenzoin (Aldrich) with ethyl bromoacetate (Aldrich) followed by LiAlH$_4$ reduction of the intermediate β-ketoester and tosylation of the formed diol]; 21) 3-phenyl-3-(4-trifluoromethylphenyl)propanol p-toluenesulfonate prepared by Horner-Emmons reaction of the sodium ylide of triethyl phosphonoacetate with 4-(trifluoromethyl)benzophenone (Aldrich) followed by catalytic hydrogenation of the intermediate α,β-unsaturated ester, LiAlH$_4$ reduction and tosylation of the formed alcohol]; 22) 3-chloro-1-(4-tert-butylphenoxy)-1-(4-fluorophenyl)propane [prepared analogously to the method of U.S. Pat. No. 5,281,624 by reduction of 3-chloro-4'-fluoropropiophenone (Aldrich) with 1.0 M borane-tetrahydrofuran complex ("BTC", Aldrich) followed by Mitzunobu reaction (diethyl azodicarboxylate ("DEAD"), Ph$_3$P, see Example 8C, Step 1) of the resulting alcohol with 4-tert-butylphenol (Aldrich)]; 23) 3-chloro-1-(2-methyl-5-pyridyloxy)-1-phenylpropane [prepared by reduction of 3-chloropropiophenone (Aldrich) with 1.0 M BTC followed by Mitzunobu reaction (DEAD, Ph$_3$P) of the resulting alcohol with 5-hydroxy-2-methylpyridine (Aldrich)]; 24) 3-chloro-1-(4-phenylphenoxy)-1-(4-fluorophenyl)propane [prepared by reduction of 3-chloro-4'-fluoropropiophenone with 1.0 M BTC followed by Mitzunobu reaction (DEAD, Ph$_3$P) of the resulting alcohol with 4-phenylphenol (Aldrich)]; 25) 3-chloro-1-(4-tert-octylphenoxy)-1-phenylpropane [prepared by reduction of 3-chloropropiophenone with 1.0 M BTC followed by Mitzunobu reaction (DEAD, Ph$_3$P) of the resulting alcohol with 4-tert-butylphenol]; 26) (R)-(+)-3-chloro-1-(4-phenylphenoxy)-1-phenylpropane [prepared by Mitzunobu reaction (DEAD, Ph$_3$P) of (R)-(+)-3chloro-1-phenyl-1-propanol (Aldrich) with 4-phenylphenol (Aldrich)(see, e.g., U.S. Pat. No. 5,068,432) (Reaction illustrated in FIG. 3, Reaction 27)]; Compound A61 was prepared with $[\alpha]_D^{25}$+ 54.9° (c 5.28, CHCl$_3$); 27) (S)(-)(-3chloro-1-(4-phenylphenoxy)-1-phenylpropane [prepared by Mitzunobu reaction (DEAD, Ph$_3$P) of (S)-(-)-3-chloro-1-phenyl-1-propanol (Aldrich) with 4-phenylphenol (see U.S. Pat. No. 5,068,432); Compound A63 was prepared with $[\alpha]_D^{25}$-54.6 (c 7.13, CHCl$_3$); 28) 3-chloro-1-(4-tert-butylphenoxy)-1-phenylpropane (prepared by reduction of 3-chloropropiophenone with 1.0 M BTC followed by Mitzunobu reaction (DEAD, Ph$_3$P) of the resulting alcohol with 4-tert-butylphenol]; 29) 3-chloro-1-{4-[4-(trifluoromethyl)phenoxy]phenoxy}-1-phenylpropane [prepared by reduction of 3-chloropropiophenone with 1.0 M BTC followed by Mitzunobu reaction (DEAD, Ph$_3$P) of the resulting alcohol with 4-[4-trifluoromethyl)phenoxy]phenol (Aldrich)]; 30) 3-chloro-1-[4-(phenoxy)phenoxy]-1-phenylpropane [prepared by reduction of 3-chloropropiophenone with 1.0 M BTC followed by Mitzunobu reaction (DEAD, Ph$_3$P) of the resulting alcohol with 4-phenoxyphenol (Aldrich)]; 31) 3-chloro-1-[4-(4-bromophenyl)phenoxy]-1-(4-fluorophenyl)propane [prepared by reduction of 3-chloropropiophenone with 1.0 M BTC followed by Mitzunobu reaction (DEAD, Ph$_3$P) of the resulting alcohol with 4-(4-bromophenyl)phenol (Aldrich)]; 32) 3-chloro-1-[4-[4-cyanophenyl)phenoxy]-1-phenylpropane [prepared by reduction of 3-chloropropiophenone with 1.0 M BTC followed by Mitzunobu reaction (DEAD, Ph$_3$P) of the resulting alcohol with 4'-hydroxy4-biphenylcarbonitrile (Aldrich)]; 33) 3-chloro-1-(3-trifluoromethylphenoxy)-1-phenylpropane [prepared by reduction of 3-chloropropiophenone with 1.0 M BTC followed by Mitzunobu reaction (DEAD, Ph$_3$P) of the resulting alcohol with 3-trifluoromethylphenol (Aldrich)]; 34) 3-chloro-12-naphthyloxy)-1-phenylpropane [prepared by reduction of 3chloropropiophenone with 1.0 M BTC followed by Mitzunobu reaction (DEAD, Ph$_3$P) of the resulting alcohol with 2-naphthol (Aldrich)]; 35) 3-chloro-1-1-naphthyloxy)-1-phenylpropane [prepared by reduction of 3-chloropropiophenone with 1.0 M BTC followed by Mitzunobu reaction (DEAD, Ph$_3$P) of the resulting alcohol with 1-naphthol (Aldrich)]; 36) 3-chloro-14-methylphenoxy)-1-phenylpropane [prepared by reduction of 3chloropropiophenone with 1.0 M BTC followed by Mitzunobu reaction (DEAD, Ph$_3$P) of the resulting alcohol with p-cresol (Aldrich)]; 37) 3-chloro-1-(4-phenylphenoxy)-1-phenylpropane [prepared by reduction of 3-chloropropiophenone with 1.0 M BTC followed by Mitzunobu reaction (DEAD, Ph$_3$P) of the resulting alcohol with 4-phenylphenol]; 38) 3-chloro-1-(4-amidosulfonylphenoxy)-1-phenylpropane [prepared by reduction of 3-chloropropiophenone with 1.0 M BTC followed by Mitzunobu reaction (DEAD, Ph$_3$P) of the resulting alcohol with 4-hydroxybenzenesulfonamide, (TCI America, Portland, Oreg.)]; 39) 3chloro-1-(4-nitrophenoxy)-phenylpropane [prepared by reduction of 3-chloropropiophenone with 1.0 M BTC followed by Mitzunobu reaction (DEAD, Ph$_3$P) of the resulting alcohol with 4-nitrophenol (Aldrich)]; 40) 3-chloro-1-(4-nitro-3-trifluoromethylphenoxy)-1-phenylpropane [prepared by reduction of 3-chloropropiophenone with 1.0 M BTC followed by Mitzunobu reaction (DEAD, Ph$_3$P) of the resulting alcohol with 4-nitro-3-trifluoromethylphenol (Aldrich)]; 41) 3-chloro-1-(4-cyanophenoxy)-1-phenylpropane [prepared by reduction of 3-chloropropiophenone with 1.0 M BTC followed by Mitzunobu reaction (DEAD, Ph$_3$P) of the resulting alcohol with 4-cyanophenol (Aldrich)]; 42) 3-chloro-1-phenoxy-1-phenylpropane [prepared by reduction of 3-chloropropiophenone with 1.0 M BTC followed by Mitzunobu reaction (DEAD, Ph₃P) of the resulting alcohol with phenol (Aldrich)); 43) 3-chloro-1-(4-trifluoromethylphenoxy)-1-phenylpropane [prepared by reduction of ³chloropropiophenone with 1.0 M BTC followed by Mitzunobu reaction (DEAD, Ph₃P) of the resulting alcohol with 4-trifluoromethylphenol; 44) 3chloro-1-[(4-trifluoromethoxy)phenoxy]-1-phenylpropane [prepared by reducing 3-chloropropiophenone with 1.0 M BTC, and Mitzunobu reaction (DEAD, Ph₃P) of resulting alcohol with 4(trifluoromethoxy)phenol (Aldrich)]; 45) 3-chloro-1-(4-trifluoromethylphenoxy)-1-(2,4-dimethoxy)phenylpropane [prepared by reduction of 3chloro 2',4'-dimethoxypropiophenone (Maybridge Chemical Co. Ltd., Cornwall, UK) with 1.0 M BTC followed by Mitzunobu reaction (DEAD, Ph₃P) of the resulting alcohol with 4-trifluoromethylphenol]; 46) 3-chloro-]-(3,4-methylenedioxyphenoxy)-1-(4-chlorophenyl)propane [prepared by reduction of 3,4'-dichloropropiophenone (Aldrich) with 1.0 M BTC followed by Mitzunobu reaction (DEAD, Ph₃P) of the resulting alcohol with sesamol (Aldrich)]; 47) 3chloro-1-phenoxy-1-(4-bromophenyl) propane [prepared by reduction of 4-bromo-p-chloropropiophenone (Lancaster) with 1.0 M BTC followed by Mitzunobu reaction (DEAD, Ph₃P) of the resulting alcohol with phenol); 48) 3chloro-1-(4-trifluoromethylphenoxy)-14-bromophenyl)propane [prepared by reduction of 4-bromo-β-chloropropiophenone, with 1.0 M BTC followed by Mitzunobu reaction (DEAD, Ph₃P) of the resulting alcohol with 4-trifluoromethylphenol]; 49)3-chloro-1-(4-methoxyphenoxy)-1-(4chlorophenyl)propane [prepared by reduction of 3,4'-dichloropropiophenone with 1.0 M BTC followed by Mitzunobu reaction (DEAD, Ph₃P) of the resulting alcohol with 4-methoxyphenol (Aldrich)]; 50) 3chloro-1-(4-cyanophenoxy)-1-(4chlorophenyl)propane [prepared by reducing 3,4'-dichloropropiophenone with 1.0 M BTC followed by Mitzunobu reaction (DEAD, Ph₃P) of the resulting alcohol with 4-cyanophenol]; 51) 3-chloro-1-(4-chlorophenoxy)-1-(4-bromophenyl)propane [prepared by reduction of 4-bromo-β-chloropropiophenone with 1.0 M BTC followed by Mitzunobu reaction (DEAD, Ph₃P) of the resulting alcohol with 4-chlorophenol (Aldrich)]; 52) 3-chloro-1-phenoxy-1-(4-chlorophenyl)propane [prepared by reduction of 3,4'-dichloropropiophenone with 1.0 M BTC followed by Mitzunobu reaction (DEAD, Ph₃P) of the resulting alcohol with phenol]; 53) 3-chloro-1-(4-methoxyphenoxy)-1-(4-fluorophenyl)propane [prepared by reducing 3-chloro-4'-fluoropropiophenone with 1.0 M BTC, and Mitzunobu reaction (DEAD, Ph₃P) of the resulting alcohol with 4-methoxyphenol]; 54) 3chloro-1-phenoxy-1-4-fluorophenyl)propane [prepared by reduction of 3-chloro-4'-fluoropropiophenone with 1.0 M BTC followed by Mitzunobu reaction (DEAD, Ph₃P) of the resulting alcohol with phenol]; 55) 3-chloro-1-(1trifluoromethylphenoxy)-1-(4-fluorophenyl)propane prepared by reduction of 3chloro-4'-fluoropropiophenone with 1.0 M BTC followed by Mitzunobu reaction (DEAD, Ph₃P) of the resulting alcohol with 4-trifluoromethylphenol]; 56) (R)-(+)-3-chloro-1-(4-nitrophenoxy)-1-phenylpropane [prepared (see, e.g., U.S. Pat. No. 5,068,432) by Mitzunobu reaction (DEAD, Ph₃P) of (R)-(+)3chloro-1-phenyl-1-propanol (Aldrich) with 4-nitrophenol]; Compound A171 was prepared with $[\alpha]_D^{25}$+ 19.7° (c 5.18, CHCl₃); 57) (S)-(–)-3-chloro-]-(4-phenylphenoxy)-1-(4-flurophenyl)propane [prepared with $[\alpha]_D^{25}$–46.3° (c 2.49, CHCl₃) analogously to U.S. Pat. No. 5,068,432 by reduction of 3-chloro-4'-fluoropropiophenone with (+) diisopinocampheylboron chloride (Aldrich) followed by Mitzunobu reaction (DEAD, Ph₃P) of the resulting (R)-(+)-3-chloro-1-(4-fluorophenyl)-1-propanol {$[\alpha]_D^{25}$+ 22.1° (c 8.07, CHCl₃)} with 4-phenylphenol, (Aldrich)]; Compound A173 was prepared with $[\alpha]_D^{25}$25.8° (c 3.03, CHCl₃); 58) (R)-(+)-3-chloro-1-(4-phenylphenoxy)-1-(4-fluorophenyl)propane [prepared with $[\alpha]_D^{25}$+46.6° (c 2.73, CHCl₃) analogously to U.S. Pat. No. 5,068,432 by reduction of 3-chloro-4'-fluoropropiophenone with (–) diisopinocampheylboron chloride (Aldrich) followed by Mitzunobu reaction (DEAD, Ph₃P) of the resulting (S)-(–)-3-chloro-1-(4-fluorophenyl)-1-propanol {$[\alpha]_D^{25}$–22.2° (c 2.37, CHCl₃)} with 4-phenylphenol, (Aldrich)]; Compound A177 was prepared with $[\alpha]_D^{25}$+26.8° (c 3.10, CHCl₃); Compound A178 was prepared with $[\alpha]_D^{25}$+20.0° (c 3.13,CHCl₃); 59)(P)-(+)-3-chloro-1-[4-(1-adamantyl)phenoxy]-]-(4-flurophenyl)propane [prepared with $[\alpha]_D^{25}$+24.3° (c 2.19, CHCl₃) analogously to U.S. Pat. No. 5,068,432 by reduction of 3-chloro-4-fluoropropiophenone with (–) diisopinocampheylboron chloride (Aldrich) followed by Mitzunobu reaction (DEAD, Ph₃P) of the resulting (S)-(–)-3-chloro-1-(4-fluorophenyl)-1-propanol {$[\alpha]_D^{25}$22.2° (c 2.37, CHCl₃)} with 4-(1-adamantyl)phenol, (Aldrich)]; Compound A179 was prepared with $[\alpha]_D^{25}$+17.8° (c 2.98, CHCl₃).

Amino acid or amino acid precursor

A) L-alanine methyl ester hydrochloride, (Fluka, Ronkonkoma, N.Y.); B) D-alanine methyl ester hydrochloride (Aldrich); C) sarcosine methyl ester hydrochloride, (Lancaster, Windham, N.H.); D) glycine methyl ester hydrochloride (Aldrich); E) glycine ethyl ester hydrochloride (Aldrich); F) sarcosine ethyl ester hydrochloride (Aldrich); and G) methylaminoacetaldehyde dimethyl acetal (Aldrich).

Solvent

X) acetonitrile; Y) methanol.

Figure 3:
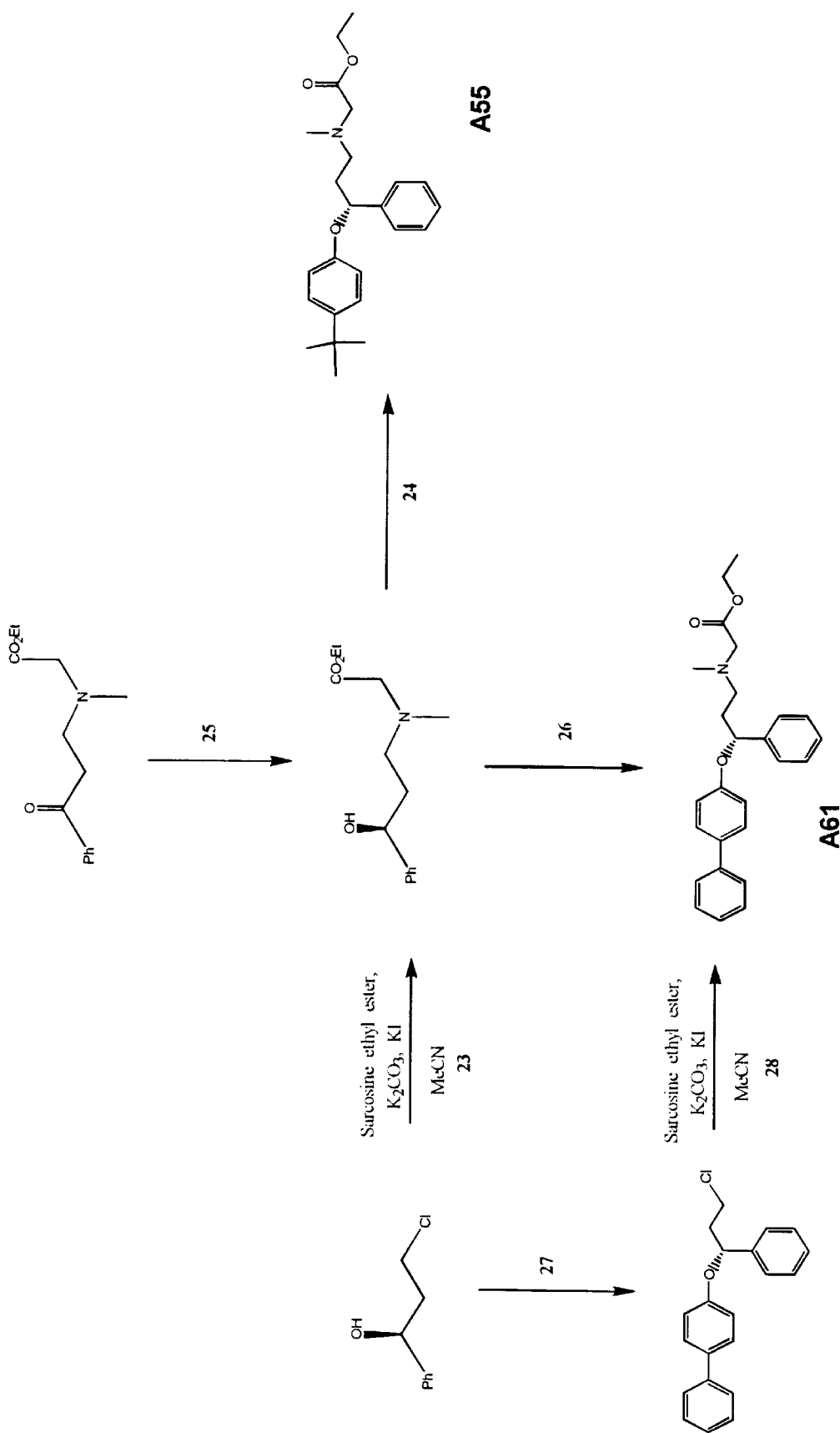
FIG. 3 shows additional representative syntheses utilized in making compounds of the invention.

For the synthesis of A61, the reaction is illustrated in FIG. 3 (Reaction 28).

EXAMPLE 3

Synthesis of N-[(3,3-Diphenyl)propyl]glycine Ethyl Ester (Compound A22)

2.132 g (10.1 mmol) 3,3-diphenylpropylamine (Aldrich, Milwaukee, Wis.) was added to a mixture of 0.853 g (5.11 mmol) ethyl bromoacetate (Aldrich) and 2.7 g (19.57 mmol) potassium carbonate in 14 ml acetonitrile at rom temperature. The mixture was stirred under argon for 18 hours. The reaction mire was filtered, the solvent evaporated and the residue chromatographed on a silica gel column with 40% ethyl acetate in hexanes to give 1.05 g (yield 69%) N-[(3, 3-diphenyl)propyl]glycine ethyl ester (Compound A22) as an oil. NMR spectra of the product showed: $^1$H NMR (CDCl₃, 300 MHz) 7.40–7.10 (m, 10 H), 4.14 (q, 2 H),4.03 (t, 1 H),3.33 (s, 2 H), 2.56 (t, 2 H), 2.24 (dt, 2 H), 1.22 (t, 3 H); $^{13}$C NMR (CDCl₃, 75 MHz) 172.44, 144.66, 128.43, 127.75, 126.15, 60.63, 50.93, 48.80, 47.92, 35.85, 14.17. 0.019 g of A28 was also isolated from the silica gel column.

EXAMPLE 4

Additional Syntheses Using Reaction 2

Additional compounds were synthesized using Reaction 2, as follows:

| Compound | Starting amine | Reagent | Solvent | Yield |
|---|---|---|---|---|
| A5 | 1 | A | X | 27% |
| A6 | 7 | B | Y | 89% |
| A10 | 9 | B | Y | 77% |
| A13 | 8 | B | Y | 95% |
| A15 | 6 | B | Y | 96% |
| A17 | 3 | B | X | 14% |
| A19 | 1 | C | X | 69% |
| A20 | 2 | E | X | 57% |
| A21 | 1 | B | X | 55% |
| A30 | 1 | H | X | 42% |
| A33 | 1 | D | X | 20% |
| A34 | 1 | G | X | 7% |
| A35 | 1 | F | X | 18% |
| A36 | 5 | B | X | 80% |
| A37 | 4 | B | X | 77% |
| A38 | 1 | E | X | 70% |
| A39 | 1 | I | X | 10% |
| A40 | 1 | J | X | 3% |
| A108 | 10 | B | X | 56% |
| A150 | 2 | K | X | 56% |
| A157 | 1 | L | X | 30% |
| A162 | 1 | K | X | 36% |
| A165 | 1 | M | X | 59% |
| A166 | 1 | N | X | 51% |
| A167 | 1 | O | X | 50% |
| A172 | 1 | P | X | 46% |

Starting amine

1) Fluoxetine [N-methyl-3-p-trifluoromethylphenoxy)-3-phenylpropylamine hydrochloride], (Sigma, St. Louis); 2) 3,3-diphenylpropylamine (Aldrich); 3) Nisoxetine hydrochloride [(±)-γ-(2-methoxyphenoxy)—N-methyl-benzenepropanamine hydrochloride], (RBI, Natick, Mass.); 4) 1,2-diphenyl-3-methyl4-(methylamino)-2-butanol hydrochloride, (Sigma-Aldrich Library of Rare Chemicals); 5) d-Norpropoxyphene (1,2-diphenyl-3-methyl4-methylamino-2-butyl propionate maleate salt), (Sigma); 6) Maprotyline hydrochloride [N-Methyl-9,10-ethanoanthracene-9(10H)-propanamine hydrochloride], (Sigma); 7) Nortriptyline hydrochloride {3-(10,11-dihydro-5H-dibenzo[a,d]cyclohepten-5-ylidene)—N-methyl-1-propanamine hydrochloride}, (Sigma); 8) Desipiramine hydrochloride {10,11-dihydro-N-methyl-5H-dibenz[b,f]azepine-5-propanamine hydrochloride}, (Sigma); 9) Protriptyline hydrochloride {N-Methyl-5H-dibenzo[a,d]cycloheptene-5-propanamine hydrochloride}, (Sigma); 10) 3-(1-naphthyl)-3-phenylpropylamine [prepared by Horner-Emmons reaction of the sodium ylide of diethyl cyanomethylphosphonate (Aldrich) with α-benzoylnaphthalene, (Pfaltz & Bauer, Waterbury, Conn.) followed by catalytic hydrogenation of the intermediate α,β-unsaturated nitrile].

Reagent

A) methyl bromoacetate (Aldrich); B) ethyl bromoacetate (Aldrich); C) propyl bromoacetate (Aldrich); D) phenyl bromoacetate (Aldrich); E) 2-bromoacetamide (Aldrich); F) 2chloro-N,N-diethylacetamide (Aldrich); G) N-ethylchloroacetamide (Lancaster); H) bromoacetonitrile (Aldrich); 1) 4-(bromomethylsulfonyl)morpholine, (Sigma—Aldrich Library of Rare Chemicals); J) diethyl chloromethylphosphonate (Aldrich); K) benzyl 2-bromoacetate, (Aldrich); L) p-nitrophenyl bromoacetate, (Lancaster); M) octyl chloroacetate, (Sigma-Aldrich Library of Rare Chemicals); N) isopropyl bromoacetate, (Aldrich); 0) n-butyl bromoacetate, (Pfatz & Bauer), Waterbury, Conn.); P) tert-butyl bromoacetate, (Aldrich).

Solvent

X) acetonitrile; Y) ethanol.

EXAMPLE 5A

Synthesis of N-{[3-Hydroxy-3-phenyl-3-(thien-2-yl)]propyl}sarcosine Ethyl Ester (Compound A32)

Step 1

Figure 2:
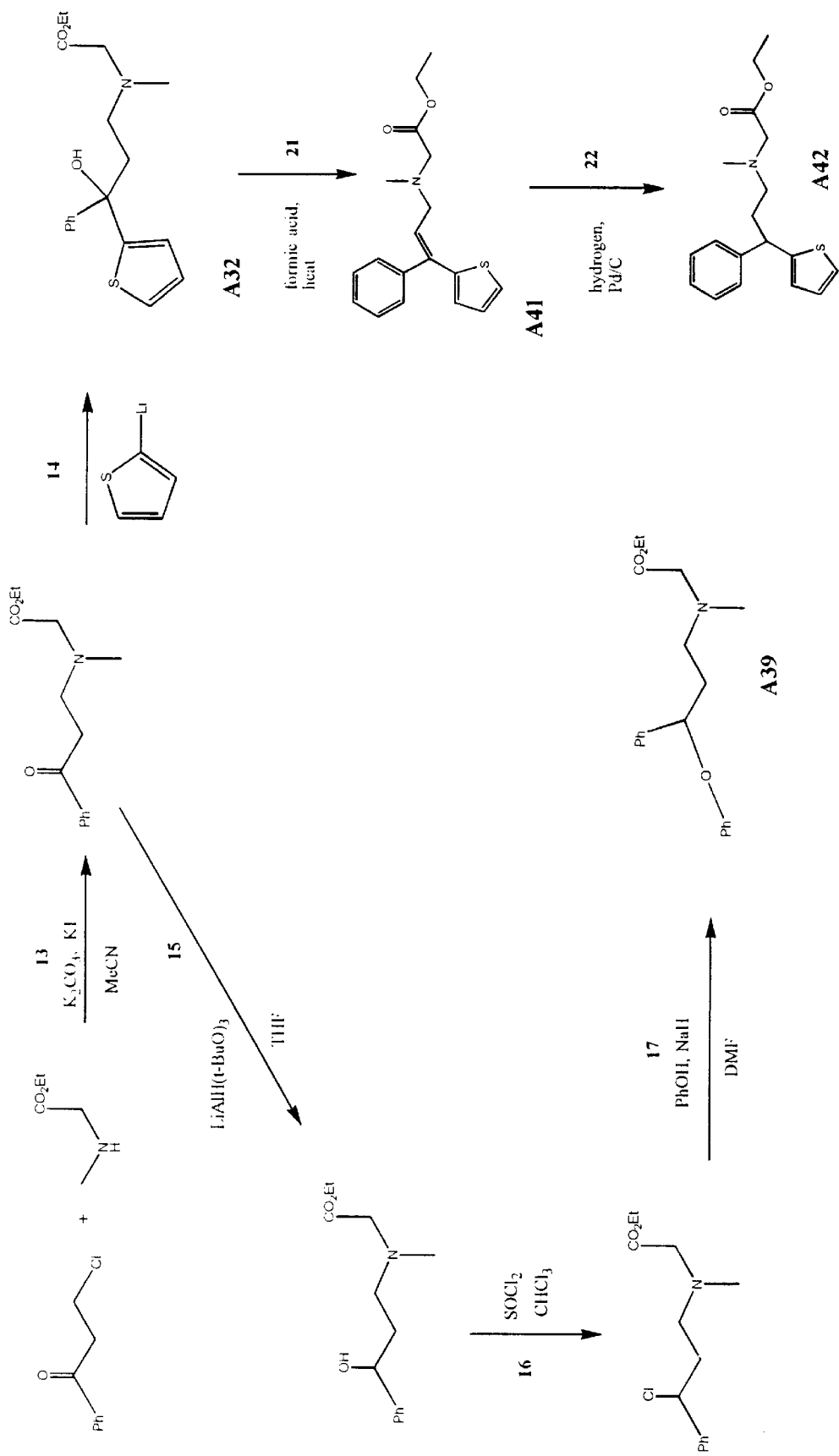
FIG. 2 depicts representative syntheses utilized in making compounds of the invention.

N-[(3-Oxo-3-phenyl)propyl]sarcosine ethyl ester: A mixture of 3.37 g (20 mmol) 3-chloropropiophenone (Aldrich), (3.07 g, (20 mmol) sarcosine ethyl ester hydrochloride, 3.32 g (20 mmol) potassium iodide and 2.5 g potassium carbonate in 140 ml acetonitrile was heated under reflux with stirring for 2 hours (see Reaction 13, FIG. 2). The reaction mixture was filtered and the solvent evaporated. The residue was dissolved in dichloromethane, washed with water and dried over sodium sulphate. Evaporation of the solvent gave N-[(3-oxo-3-phenyl)propyl]sarcosine ethyl ester as a yellow oil which was used in step 2 without purification.

Step 2

2-Thienyllithium [generated by adding 1 ml of butyl-lithium (2.5 M in tetrahydrofuran) to 0.21 g (2.5 mmol) thiophene in 10 ml tetrahydrofuran at −78° C.] was added dropwise into a solution of 0.623 g (2.5 mmol) of N-[(3-oxo-3-phenyl)propyl]sarcosine ethyl ester (from step 1) in 30 ml of tetrahydrofuran at −78° C. (see Reaction 14, FIG. 2). After stirring at −78° C. for 1 h and at 20° C. for 1 h, the reaction was quenched by adding 20 ml 10% ammonium hydroxide solution at 0° C. The mixture was extracted with methylene chloride, the solvent evaporated and the residue chromatographed on silica gel column with 16% ethyl acetate in hexanes to give 0.43 g (yield 52%) N-{[3-hydroxy-3-phenyl-3-(thien-2-yl)]propyl}sarcosine ethyl ester (compound A32) as a beige solid.

EXAMPLE 5B

Synthesis of N-{[3-Hydroxy-3-phenyl-3-(furan-2-yl)]propyl}sarcosine Ethyl Ester (Compound A161)

N-{[3-Hydroxy-3-phenyl-3-(furan-2-yl)]propyl}sarcosine ethyl ester was synthesized essentially as described in Example 5A (replacing 2-thienyllithium with 2-furanyllithium) (yield 14%).

EXAMPLE 6

Synthesis of N-[3-Phenyl-3(thien-2-yl)2-propenyl] sarcosine Ethyl Ester (Compound A41)

N-{[3-Hydroxy-3-phenyl-3-(thien-2-yl)]propyl}sarcosine ethyl ester (Compound 32 from Example 5), 0.118 g (0.354 mmol) was dissolved in 2 ml of formic acid. The solution was heated at 110° C. for 0.5 hour (see Reaction 19, FIG. 2). The deep red reaction mixture was concentrated and the residue was partitioned between water and $CH_2Cl_2$. The aqueous phase was extracted with $CH_2Cl_2$ and the $CH_2Cl_2$ solution was dried over $Na_2SO_4$. After evaporating the solvent, the residue was purified by preparative TLC with 1:3 ethyl acetate:hexanes to give 0.091 g (82%) N-[3-phenyl-3-(thien-2-yl)-2-propenyl]sarcosine ethyl ester (Compound A41) as a deep red oil.

EXAMPLE 7

Synthesis of N-[3-Phenyl-3-(thien-2-yl)propyl] sarcosine Ethyl Ester (Compound A42)

0.055 g (0.174 mmol) N-[3-Phenyl-3-(thien-2-yl)-2-propenyl]sarcosine ethyl ester (Compound 41 from Example 6) was hydrogenated over 0.055 g 10% Pd/C in 2 ml of EtOH. The hydrogenation was conducted at 40 psi for 16 hours at room temperature (see Reaction 20, FIG. 2). After filtering off the catalyst the solution was concentrated and the residue was purified by preparative TLC with 1:2 ethyl acetate:hexanes to give 0.012 g (22%) N-[3-phenyl-3-(thien-2-yl)propyl]sarcosine ethyl ester (Compound A42) as a yellow oil.

EXAMPLE 8A

Synthesis of N-[(3-Phenyl-3-phenoxy)propyl] sarcosine ethyl ester (compound A31)

Step 1

N-[(3-Hydroxy-3-phenyl)propyl]sarcosine ethyl ester: 2.40 ml of LiAl(t-BuO)$_3$ [lithium tri-tert-butoxyaluminohydride (Aldrich) (1 M in THF)] was added into a solution of 0.593 g (2.38 mmol) N-[(3-oxo-3-phenyl) propyl]sarcosine ethyl ester (step 1 of Example 5A) in 10 ml of tetrahydrofuran at −78° C. (see Reaction 15 in FIG. 2). After stirring at -78° C. for 1 h and 1 h at room temperature, the reaction was quenched by adding 10 ml 10% ammonium chloride solution at 0° C. and filtered through celite. The mixture was extracted with methylene chloride and dried over sodium sulphate. Evaporation of the solvent gave N-[(3-hydroxy-3-phenyl)propyl]sarcosine ethyl ester as a yellow oil which was used in the next step without further purification.

Step 2

N-[(3-Chloro-3-phenyl)propyl]sarcosine ethyl ester: The yellow oil of step 1 was dissolved in 20 ml of chloroform, 1 ml of SOCl$_2$ was added and the mixture heated under reflux for 2 h (see Reaction 16 in FIG. 2). After addition of crushed ice, the reaction mixture was neutralized with a saturated solution of potassium carbonate and extracted with methylene chloride. The combined extracts were evaporated and the residue purified by preparative silica gel TLC with 20% ethyl acetate in hexanes to give 0.165 g N-[(3-chloro-3-phenyl)propyl]sarcosine ethyl ester (yield 26% in two steps).

Step 3

N-[(3-Phenyl-3-phenoxy)propyl]sarcosine ethyl ester (compound A31): A solution of 0.075 g (0.278 mmol) N-[(3-chloro-3-phenyl)propyl]sarcosine ethyl ester (from step 2) in 3 ml of anhydrous dimethylformamide was added into a solution of sodium phenoxide (generated by adding 0.022 g of 60% NaH in mineral oil to 0.054 g phenol in 2 ml dimethylformamide) at room temperature (see Reaction 17 in FIG. 2). The reaction mixture was stirred at room temperature for 30 hours, the solvent was evaporated under vacuum and the residue purified by preparative silica gel TLC with 35% ethyl acetate in hexanes to give 0.014 g (yield 15%) N-[(3-phenyl-3-phenoxypropyl]sarcosine ethyl ester (compound A31) as a yellow oil.

EXAMPLE 8B

Additional Syntheses Using the Procedure of Example 8A

Compound A164 was prepared by alkylation of 4-methoxyphenol (Aldrich) with N-(3-chloro-3-phenylpropyl)sarcosine ethyl ester as described above in Example 8A (Step 3)—yield 5%.

Compound A119 was prepared by alkylation of thiophenol (Aldrich) with N-(3-chloro-3-phenylpropyl)sarcosine ethyl ester as described above in Example 8A (Step 3) yield 62%.

Compound A115 was prepared by alkylation of 4-(trifluoromethyl)thiophenol (Lancaster) with N-(3-chloro-3-phenylpropyl)sarcosine ethyl ester as described above in Example 8A (Step 3)—yield 93%.

Compound A68 was prepared by alkylation of 4-tert-butylthiophenol (Lancaster) with N-(3-chloro-3-phenylpropyl)sarcosine ethyl ester as described above in Example 8A (Step 3)—yield 5%.

EXAMPLE 8C

Synthesis of N-[3Phenyl-3-(phenylaminopropyl] sarcosine Ethyl Ester (Compound A47)

Step 1

N-[3-Phenyl-3-(p-toluenesulfonanilido)propyl]sarcosine ethyl ester: 0.465 g (2.67 mmol) diethyl azodicarboxylate ("DEAD", Aldrich) was added dropwise to a solution of 0.511 g (2.03 mmol) N-(3-hydroxy-3-phenylpropyl) sarcosine ethyl ester (from Example 8A, Step 1), 0.571 g (2.31 mmol) p-toluenesulfonanilide, (TCI America, Portland, Oreg.) and 0.712 g (2.71 mmol) triphenylphosphine in 2 ml anhydrous tetrahydrofuran with stirring under nitrogen and cooling with an ice bath. The mixture was stirred at room temperature for 4 hours, the solvent evaporated and the residue chromatographed on silica gel with 25% ethyl acetate in hexanes to give 0.730 g (yield 74%) N-[3-phenyl-3-(p-toluenesulfonanilido)propyl]sarcosine ethyl ester. $^1$H NMR (CDCl$_3$, 300 MHz) 7.58 (d, 2 H), 7.40–6.90 (m, 10 H), 6.62 (d, 2 H), 5.55 (t, 1 H), 4.14 (q, 2 H), 3.20 (s, 2 H), 2.60–2.20 (m, 2 H), 2.39 (s, 3 H), 2.33 (s, 3 H), 2.20–1.80 (m, 2 H), 1.12 (t, 3 H); $^{13}$C NMR (CDCl$_3$, 75 MHz) 170.74, 142.90, 138.33, 138.08, 134.88, 132.78, 129.14, 128.60, 128.36, 128.28, 127.93, 127.79, 127.46, 60.51, 60.26, 58.57, 53.93, 42.16, 30.60, 21.36, 14.12.

Step 2

N-[3-Phenyl-3-(phenylamino)propyl]sarcosine ethyl ester (Compound A47): A solution of 0.284 g (0.6 mmol) N-[3-phenyl-3-(p-toluenesulfonanilido)propyl]sarcosine ethyl ester (from Step 1) in 3 ml anhydrous ethylene glycol dimethyl ether was added dropwise within 1 hour into solution of sodium naphthalenide [prepared from 0.545 g (5.04 mmol) naphthalene and 0.110 g (5.16 mmol) sodium) in 8 ml anhydrous ethylene glycol dimethyl ether with stirring under nitrogen and cooling with an ice bath. The mixture was stirred at room temperature for 1 hour, quenched with ice and extracted with ethyl acetate. The combined organic extracts were washed with brine, the solvent evaporated and the residue chromatographed on silica gel with 25% ethyl acetate in hexanes to give 0.092 g (yield 47%) N-[3-phenyl-3-(phenylamino)propyl]sarcosine ethyl ester (Compound A47). $^1$H NMR (CDCl$_3$, 300 MHz) 7.50–7.00 (m, 7 H), 6.70–6.40 (m, 3 H), 5.75 (br. s, 1 H), 4.47 (t, 1 H), 4.18 (q, 2 H), 3.24 (s, 2 H), 2.57 (t, 2 H), 2.37 (s, 3 H), 2.10–1.70 (m, 2 H), 1.18 (t, 3 H); $^{13}$C NMR (CDCl$_3$, 75 MHz) 170.73, 147.82, 143.89, 128.87, 128.43, 126.69, 126.26, 116.57, 113.17, 60.47, 58.53, 57.92, 54.47, 42.32, 35.19, 14.18.

EXAMPLE 8D

Synthesis of [R]-(+)-N-[3-Phenyl-3-(4-tert-butylphenoxy)propyl]sarcosine Ethyl Ester (Compound A55) {[α]$_D^{25}$+18.6° (c 7.84, CHCl$_3$)}

Step 1

[S]-(−)-N-3-Hydroxy-3-phenylpropyl)sarcosine ethyl ester {[α]$_D^{25}$−35° (c 4.88, CHCl$_3$)}; prepared by alkylation of sarcosine ethyl ester with (R)-(+)-3-chloro-1-phenyl-1-propanol (Aldrich) under the conditions described in Example 1—yield 72%. See Reaction 23, FIG. 3.

Step 2

[R]-(+)-N-[3-Phenyl-3-(4-tert-butylphenoxy)propyl] sarcosine ethyl ester: prepared by Mitzunobu reaction (analogously to Example 8C, Step 1) of [S]-(−)-N-(3-hydroxy-3-phenylpropyl)sarcosine ethyl ester (from step 1) with 4-tert-butylphenol (Aldrich)—yield 41%; $[\alpha]_D^{25}$+18.6° (c 7.84, CHCl$_3$). See Reaction 24, FIG. 3.

EXAMPLE 8E

Synthesis of [R]-(+)-N-[3-Phenyl-3-(4-phenylphenoxy)propyl]sarcosine Ethyl Ester (Compound A61) {$[\alpha]_D^{25}$+22.3° (c 8.1. CHCl$_3$)}

Another synthesis of compound A61 with $[\alpha]_D^{25}$+54.9° (c 5.28, CHCl$_3$) was already described in Example 2.

Step 1

[S]-(−)—N-(3-Hydroxy-3-phenylpropyl)sarcosine ethyl ester: prepared analogously to the method of U.S. Pat. No. 5,068,432 by reduction of N-[(3-oxo3-phenyl)propyl] sarcosine ethyl ester (from step 1 of Example 5A) with (−) diisopinocampheylboron chloride (Aldrich)—yield 12%; $[\alpha]_D^{25}$−24.6° (c 3.63, CHCl$_3$) (see Reaction 25, FIG. 3). Another synthesis of [S]-(−)-N-(3-hydroxy-3-phenylpropyl) sarcosine ethyl ester with $[\alpha]_D^{25}$−35° (c 4.88, CHCl$_3$) was already described in Example 8D (Step 1). See Reaction 23, FIG. 3.

Step 2

[R]-(+)—N-[3-Phenyl-3-(4-phenylphenoxy)propyl] sarcosine ethyl ester (Compound A61): prepared by Mitzunobu reaction (analogously to Example 8C, Step 1) of [S]-(−)—N-(3-hydroxy-3-phenylpropyl)sarcosine ethyl ester (from step 1) with 4-phenylphenol (Aldrich)—yield 22%; $[\alpha]_D^{25}$+22.3° (c 8.1, CHCl$_3$). See Reaction 26, FIG. 3.

EXAMPLE 9A

Synthesis of N-1(4,4-Diphenyl)but-3-enyl]-N-ethylglycine Ethyl Ester (Compound A16)

A mixture of 0.158 g (0.5 mmol) of N-[(4,4-diphenyl) but-3-enyl]glycine ethyl ester (Compound A26), 0.234 g (2.1 mmol) bromoethane, 0.281 g (2 mmol) potassium carbonate and 0.068 g (0.4 mmol) potassium iodide was stirred under argon for 20 hours at room temperature. The reaction mixture was filtered, the solvent evaporated, and the residue chromatographed on a silica gel column with 20% ethyl acetate in hexanes to yield 0.112 g (66%) N-[(4,4-diphenyl)but-3-enyl]-N-ethylglycine ethyl ester (Compound A16) as an oil. NMR spectra showed: $^1$H NMR (CDCl$_3$, 300 MHz) 7.60–7.00 (m, 10 H), 6.09 (t, 1 H), 4.13 (q, 2 H), 3.27 (s, 2 H), 2.72 (t, 2 H), 2.61 (q, 2 H), 2.28 (dt, 2 H), 1.23 (t, 3 H), 1.01 (t, 3 H); $^{13}$C NMR (CDCl$_3$, 75 MHz) 171.77, 142.96, 142.86, 140.33, 130.09, 128.49, 128.35, 127.48, 127.27, 127.19, 60.58, 54.90, 53.98, 48.20, 28.19, 14.57, 12.70.

EXAMPLE 9B

Additional Syntheses Using the Procedure of Example 9A

Compound A147 was prepared by treatment of compound A150 with iodomethane under the conditions described in Example 9A—yield 30%.

EXAMPLE 10

Synthesis of N-[(4,4-Diphenyl)butyl]glycine Ethyl Ester (Compound A4)

0.072 g (0.23 mmol) of N-[(4,4 diphenyl)but-3-enyl] glycine ethyl ester (compound A26) was hydrogenated over 0.072 g 10% Pd/C in 5 ml ethanol under 40 psi for 3 hours at room temperature. The mixture was filtered from the catalyst through celite and the solvent evaporated to give 0.065 g (yield 90%) N-[(4,4-diphenyl)butyl]glycine ethyl ester (compound A4) as an oil. NMR spectra of the product showed: $^1$H NMR (CDCl$_3$, 300 MHz) 7.40–7.10 (m, 10 ), 4.17 (q, 2 H), 3.89 (t, 1 H), 3.34 (s, 2 H), 2.61 (t, 2 H), 2.08 (dt, 2 H), 1.50–1.40 (m, 2 1), 1.25 (t, 3 H), $^{13}$C NMR (CDCl$_3$, 75 MHz) 172.47, 144.89, 148.36, 127.77, 126.05, 60.63, 51.17, 50.90, 49.44, 33.19, 28.50, 14.17.

EXAMPLE 11

Additional Syntheses Using the Procedure of Example 10

Compound A25 was prepared by catalytic hydrogenation, using 10% palladium on carbon, of compound A2—yield 90%.

Compound A3 was prepared by catalytic hydrogenation, using 10% palladium on carbon, of compound A16—yield 90%.

EXAMPLE 12

Synthesis of N-[(4,4-Diphenyl)but-3enyl]glycine Hydrochloride (Compound A27)

To a solution of 0.093 g (0.3 mmol) of N-[(4,4-diphenyl) but-3-enyl]glycine ethyl ester (compound A26) in 2 ml methanol was added 3.4 ml 1N sodium hydroxide and the mixture was heated under reflux for four hours. The reaction mixture was concentrated to half volume, acidified with 4 N hydrochloric acid, and extracted 4 times with methylene chloride. The combined extracts were dried and evaporated to give 0.100 g (yield 86%) of N-[(4,4-diphenyl)but-3-enyl] glycine hydrochloride (compound A27). NMR spectra of the product showed: $^1$H NMR (CD$_3$OD, 300 MHz) 7.40–7.00 (m, 10 H), 5.96 (t, I H), 3.81 (s, 1 H), 3.69 (s, 2 H, 3.04 (br.s, 2 H), 2.42 (br.s, 2 H); $^{13}$C NMR (CD$_3$OD, 75 MHz) 166.78, 145.86, 145.82, 141.73, 139.34, 129.42, 128.42, 127.96, 127.41, 127.35, 127.02, 121.97, 121.87, 52.28, 26.43.

EXAMPLE 13A

Additional Syntheses Using the Procedure of Example 12

The following N-modified amino acids were prepared by hydrolysis of the corresponding esters with 1N sodium hydroxide in methanol, or with 1N lithium hydroxide in ethanol at room temperature, followed by acidification with hydrochloric acid as described above in Example 12, where the parenthetical lists the starting ester, yield, and—where applicable, $[\alpha]_D^{25}$:

| | | |
|---|---|---|
| A8 (A4, 86%) | A29 (A5, 70%) | A44 (A48, 98%) |
| A45 (A53, 98%) | A46 (A55, 98%, +2.38° (c 2.4, CHCl$_3$)) | A49 (A50, 95%) |

| | | |
|---|---|---|
| A51 (A52, 82%) | A54 (A68, 52%) | A56 (A57, 71%) |
| A58 (A59, 98%) | A60 (A61, 80%, +25.3° (c 2.13, MeOH) | A62 (A63, 69%, −25.6 (c 2.4, MeOH)) |
| A64 (A73, 90%) | A65 (A74, 90%) | A66 (A67, 60%) |
| A69 (A70, 99%) | A72 (A75, 98%) | A76 (A77, 75%) |
| A79 (A80, 62%) | A81 (A89, 64%) | A84 (A85, 93%) |
| A86 (A87, 98%) | A91 (A71, 54%) | A92 (A40, 90%) |
| A93 (A95, 95%) | A94 (A96, 95%) | |
| A98 (A100, 95%) | A101 (A118, 53%) | A102 (A108, 61%) |
| A103 (A104, 83%) | A105 (A106, 86%) | A107 (A115, 76%) |
| A109 (A123, 98%) | A110 (A169, 68%) | A112 (A117, 62%) |
| A113 (A119, 56%) | A114 (A120, 98%) | A116 (A122, 35%) |
| A124 (A126, 62%) | A131 (A132, 82%) | A135 (A134, 92%) |
| A136 (A145, 98%) | A137 (A164, 85%) | A144 (A158, 43%) |
| A152 (A156, 58%) | A154 (A160, 98%) | A174 (A43, 91%) |
| A175 (A171, 38%, +10 (c 2.9, MeOH)) | A176 (A88, 61%) | A181 (A173, 82%, −16.6° (c 3.11, MeOH)) |
| A182 (A177, 78%, +19.0° (c 2.93, MeOH)) | A183 (A178, 72%, +13.7° (c 2.68, MeOH)) | A184 (A179, 98%, +13.5° (c 2.5, MeOH)) |

EXAMPLE 13B

Synthesis of N-Methyl-N-[(1H-tetrazol-yl)methyl]-3,3-diphenylpropylamine Hydrochloride (Compound A146)

Step 1

A mixture of 2.11 g (10 mmol) 3,3-diphenylpropylamine (Aldrich), (0.54 g, 4.54 mmol) bromoacetonitrile (Aldrich), and 2.5 g potassium carbonate in 5 ml acetonitrile was stirred at room temperature for 16 hours. The reaction mixture was diluted with dichloromethane, washed with water, the solvent evaporated, and the residue chromatographed on silica gel column with 30% ethyl acetate in hexanes to give 1.24 g (yield 50%) N-cyanomethyl-3,3-diphenylpropylamine as an oil which solidified on standing. $^1$H NMR (CDCl$_3$, 300 MHz) 7.45–7.10 (m, 10 H), 4.05 (t, 1 H), 3.50 (s, 2 H), 2.67 (t, 2 H), 2.23 (dt, 2H); $^{13}$C NMR (CDCl$_3$, 75 MHz) 144.25, 128.53, 127.68, 126.33, 117.72, 48.58, 47.13, 37.19, 35.14.

Step 2

A mixture of 0.72 g (2.9 mmol) N-cyanomethyl-3,3-diphenylpropylamine (from step 1), 0.49 g (3.4 mmol) iodomethane and 1.6 g potassium carbonate in 5 ml acetonitrile was stirred at room temperature for 16 hours. The reaction mixture was diluted with dichloromethane, washed with water, the solvent evaporated, and the residue chromatographed on silica gel column with 20% ethyl acetate in hexanes to give 0.33 g (yield 43%) N-methyl-N-cyanomethyl-3,3-diphenylpropylamine as an oil which solidified on standing. $^1$H NMR ((CDCl$_3$, 300 MHz) 7.30–7.10 (m, 10 H), 4.02 (t, 1 H, 3.47 (s, 3 H), 2.38 (t, 2 H), 2.32 (s, 3H), 2.19 (dt, 2H);

Step 3

A mixture of 0.132 g (0.5 mmol) N-methyl-N-cyanomethyl-3,3-diphenylpropylamine (from step 2) and 0.183 g (0.55 mmol) azidotributyltin (Aldrich) was stirred at 80° C. under argon for 16 hours. The reaction mixture was suspended with 1 M solution of hydrogen chloride in diethyl ether (Aldrich) and the precipitated yellow wax was purified by preparative TLC with 10% methanol in ethyl acetate to give 0.06 g (yield 35%) N-methyl-N-[(1H-tetrazol-5-yl) methyl]-3,3-diphenylpropylamine hydrochloride (Compound A146)as a white powder. $^1$H NMR (DMSO-d$_6$, 300 MHz) 7.30–7.16(m, 10H),4.11 (s, 2H), 3.97 (t, I H), 2.60 (br. s, 2 H), 2.45 (s, 3H), 2.36 (br. s, 2H).

EXAMPLE 13C

Additional Syntheses Using the Procedure of Example 13B

Compound A133 was prepared by treatment of compound A30 with azidotributyltin as described above in Example 13B (Step 3)—yield 11%.

EXAMPLE 13D

Synthesis of Dimethyl(ethoxycarbonylmethyl)[3-phenyl-3-(4-trifluoromethylphenoxy)propyl] ammonium Iodide (Compound A148)

A solution of 0.152 g (0.38 mmol) N-[3-phenyl-3-(4-trifluoromethylphenoxy)propyl]sarcosine ethyl ester (Compound A2 ) and 0.273 g (1.93 mmol) iodomethane in 2 ml benzene was heated under reflux for 2 hours and the solvent evaporated. The residue was washed three times with anhydrous diethyl ether and dried under vacuum to give 0.175 g (yield 85%) dimethyl(ethoxycarbonylmethyl)[3-phenyl-3-(4trifluoromethylphenoxy)propyl]ammonium iodide (Compound A148) as a pale yellow hygroscopic powder.

EXAMPLE 14

Preparation of Cells Expressing GlyT-1 and GlyT-2

This example sets forth methods and materials used for growing and transfecting QT-6 cells.

QT-6 cells were obtained from American Type Culture Collection (Accession No. ATCC CRL-1708). Complete QT-6 medium for growing QT-6 is Medium 199 (Sigma Chemical Company, St. Louis, Mo.; hereinafter "Sigma") supplemented to be 10% tryptose phosphate; 5% fetal bovine serum (Sigma); 1% penicillin-streptomycin (Sigma); and 1% sterile dimethylsulfoxide (DMSO; Sigma). Other solutions required for growing or transfecting QT-6 cells included:

DNA/DEAE Mix

450 μl TBS, 450 μl DEAE Dextran (Sigma), and 100 μl of DNA (4 μg) in TE, where the DNA includes GlyT-1a, GlyT-1b, GlyT-1c, or GlyT-2, in a suitable expression vector. The DNA used was as defined below.

PBS

Standard phosphate buffered saline, pH 7.4 including 1 mM CaCl$_2$ and I mM MgCl$_2$ sterilized through 0.2 g filter.

TBS

One ml of Solution B, 10 ml of Solution A; brought to 100 ml with distilled H$_2$O; filter-sterilized and stored at 4° C.

TE 0.01 M Tris, 0.001 M EDTA, pH 8.0.

DEAE dextran

Sigma, #D-9885. A stock solution was prepared consisting of 0.1% (1 mg/ml) of the DEAE dextran in TBS. The stock solution was filter sterilized and frozen in 1 ml aliquots.

Chloroquine

Sigma, #C-6628. A stock solution was prepared consisting of 100 mM chloroquine in H$_2$O. The stock solution was filter-sterilized and stored in 0.5 ml aliquots, frozen.

Solution A (10×)

| | |
|---|---|
| NaCl | 8.00 g |
| KCl | 0.38 g |
| $Na_2HPO_4$ | 0.20 g |
| Tris base | 3.00 g |

The solution was adjusted to pH 7.5 with HCl, brought to 100.0 ml with distilled $H_2O$, and filter-sterilized and stored at room temperature.

Solution B (100×)

| | |
|---|---|
| $CaCl_2 \cdot 2H_2O$ | 1.5 g |
| $MgCl_2 \cdot 6H_2O$ | 1.0 g |

The solution was brought to 100 ml with distilled $H_2O$, and filter-sterilized; the solution was then stored at room temperature.

HBSS 150 mM NaCl, 20 mM HEPES, 1 mM $CaCl_2$, 10 mM glucose, 5 mM KCl, 1 mM $MgCl_2$ $H_2O$; adjusted with NaOH to pH 7.4.

Standard growth and passaging procedures used were as follows: Cells were grown in 225 ml flasks. For passaging, cells were washed twice with warm HBSS (5 ml each wash). Two ml of a 0.05% trypsin/EDTA solution was added, the culture was swirled, then the trypsin/EDTA solution was aspirated quickly. The culture was then incubated about 2 minutes (until cells lift off), then 10 ml of QT-6 media was added and the cells were further dislodged by swirling the flask and tapping its bottom. The cells were removed and transferred to a 15 ml conical tube, centrifuged at 1000×g for 10 minutes, and resuspended in 10 n11 of QT-6 medium. A sample was removed for counting, the cells were then diluted further to a concentration of $1\times10^5$ cells/ml using QT-6 medium, and 65 ml of the culture was added per 225 ml flask of passaged cells.

Transfection was accomplished using cDNA's prepared as follows:

The rat GlyT-2 (rGlyT-2) clone used contains the entire sequence of rGlyT-2 cloned into pBluescript SK+ (Stratagene) as an Eco RI-Hind III fragment, as described in Liu et al., *J. Biol. Chem.* 26A 22802–22808 (1993). GlyT-2 was then subcloned into the pRc/RSV vector as follows: A PCR fragment corresponding to nucleotides 208 to 702 of the rGlyT-2 sequence was amplified by PCR using the oligonucleotide: 5'GGGGGAAGCTTATGGATTGCAGT-GCTCC3' as the 5' primer and the oligonucleotide: 5' GGGGGGGTACCCAACACCACTGTGCTCTG 3' as the 3' primer. This created a Hind III site immediately upstream of the translation start site. This fragment which contained a Kpn I site at the 3' end, along with a Kpn 1-Pvu II fragment containing the remainder of the coding sequence of rGlyT-2, were cloned into pBluescript SK+ previously digested with Hind III and Sma I, in a three part ligation. A Hind III-Xba 1 fragment from this clone was then subcloned into the pRc/RSV vector. The resulting construct contains nucleotides 208 to 2720 of the rGlyT-2 nucleic acid in the pRc/RSV expression vector.

The human GlyT-1a (hGlyT-1a) clone used contains the sequence of hGlyT-1a from nucleotide position 183 to 2108 cloned into the pRc/CMV vector (Invitrogen, San Diego, Calif.) as a Hind III-Xba I fragment as described in Kim et al., *Mol. Pharmacol.* 45, 608–617, 1994. This cDNA encoding GlyT-1a actually contained the first 17 nucleotides (corresponding to the first 6 amino acids) of the GlyT-1a sequence from rat. To determine whether the sequence of human GlyT-1a was different in this region, the 5' region of hGlyT-1a from nucleotide 1 to 212 was obtained by rapid amplification of cDNA end using the 5' RACE system supplied by Gibco BRL (Gaithersburg, Md.). The gene specific primer: 5' CCACATTGTAGTAGATGCCG 3' corresponding to nucleotides 558 to 539 of the hGlyT-1a sequence, was used to prime cDNA synthesis from human brain mRNA, and the gene specific primer: 5' GCAAACTGGCCGAAGGAGAGCTCC3', corresponding to nucleotides 454 to 431 of the hGlyT-1a sequence, was used for PCR amplification. Sequencing of this 5' region of GlyT-1a confirmed that the first 17 nucleotides of coding sequence are identical in human and rat GlyT-1a.

The human GlyT-1b (hGlyT-1b) clone used contains the sequence of hGlyT-1b from nucleotide position 213 to 2274 cloned into the pRc/CMV vector as a Hind III-Xba I fragment as described in Kim et al., *Mol. Pharmacol.* 45, 608–617, 1994.

The human GlyT-1c (hGlyT-1c) clone used contains the sequence of hGlyT-1c from nucleotide position 213 to 2336 cloned into the pRc/CMV vector (Invitrogen) as a Hind III-Xba I fragment as described in Kim et al., *Mol. Pharmacol.* 45, 608–617, 1994. The Hind III-Xba fragment of hGlyT-1c from this clone was then subcloned into the pRc/RSV vector. Transfection experiments were performed with GlyT-1c in both the pRc/RSV and pRc/CMV expression vectors.

The following four day procedure for the tranfections was used:

On day 1, QT-6 cells were plated at a density of $1\times10^6$ cells in 10 ml of complete QT-6 medium in 100 mm dishes.

On day 2, the media was aspirated and the cells were washed with 10 ml of PBS followed by 10 ml of TBS. The TBS was aspirated, and then 1 ml of the DEAE/DNA mix was added to the plate. The plate was swirled in the hood every 5 minutes. After 30 minutes, 8 ml of 80 $\mu$M chloroquine, in QT-6 medium was added and the culture was incubated for 2.5 hours at 37° C. and 5% $CO_2$. The medium was then aspirated and the cells were washed two times with complete QT-6 media, then 100 ml complete QT-6 media was added and the cells were returned to the incubator.

On day 3, the cells were removed with trypsin/EDTA as described above, and plated into the wells of 96-well assay plates at approximately $2\times10^5$ cells/well.

On day 4, glycine transport was assayed (see Example 15).

EXAMPLE 15

Assay of Transport Via GlyT-1 or GlyT-2 Transporters

This example illustrates a method for the measurement of glycine uptake by transfected cultured cells.

Transient GlyT-transfected cells grown in accordance with Example 14 were washed three times with HEPES buffered saline (HBS). The cells were then incubated 10 minutes at 37° C., after which a solution was added containing 50 nM [$^3$H]glycine (17.5 Ci/mmol) and either (a) no potential competitor, (b) 10 mM nonradioactive glycine or (c) a concentration of a candidate drug. A range of concentrations of the candidate drug was used to generate data for calculating the concentration resulting in 50% of the effect (e.g., the $IC_{50}s$, which are the concentrations of drug inhibiting glycine uptake by 50%). The cells were then incubated another 10 minutes at 37° C., after which the cells were aspirated and washed three times with ice-cold HBS. The cells were harvested, scintillant was added to the cells, the cells were shaken for 30 minutes, and the radioactivity in the cells was counted using a scintillation counter. Data were compared between the same cells contacted or not contacted by a candidate agent, and between cells having GlyT-1 activity versus cells having GlyT-2 activity, depending on the assay being conducted.

EXAMPLE 16

Assay of Binding to NMDA Receptors

This example illustrates binding assays to measure interaction of compounds with the glycine site on the NMDA receptor.

Direct binding of [$^3$H]glycine to the NMDA-glycine site was performed according to the method of Grimwood et al., *Molecular Pharmacology* 4, 923–930 (1992); Yoneda et al., *J. Neurochem*, 62, 102–112 (1994).

Preparation of membranes for the binding test required application of a series of standard methods. Unless otherwise specified, tissues and homogenates were kept on ice and centrifugations were conducted at 4° C. Homogenizations were conducted with an effort to minimize resulting rise in tissue/homogenate temperature. The membrane preparation included the following steps:

A. Sacrifice and decapitate four rats; remove cortices and hippocampi.

B. Homogenize tissue in twenty volumes of 0.32 M sucrose/5 mM Tris-Acetate (pH 7.4) with 20 strokes of a glass/teflon homogenizer.

C. Centrifuge tissue at 1000×g, 10 minutes. Save supernatant. Resuspend pellet in small volume of buffer and homogenize again. Centrifuge the homogenized pellet and combine the supernatant with the previous supernatant.

D. Centrifuge the combined supernatants at 40,000×g, for 30 minutes. Discard the supernatant.

E. Resuspend the pellet in 20 volumes of 5 mM Tris-Acetate (pH 7.4). Stir the suspension on ice for one hour. Centrifuge the suspension at 40,000×g for 30 minutes. Discard the supernatant and freeze the pellet for at least 24 hours.

F. Resuspend the pellet from step 5 in Tris Acetate buffer (5 mM, pH 7.4) containing 0.1% saponin (w/v; Sigma Chemical Co., St. Louis) to a protein concentration of 1 mg/ml. Leave on ice for 20 minutes. Centrifuge the suspension at 40,000×g for 30 minutes. Resuspend the pellet in saponin-free buffer and centrifuge again. Resuspend the pellet in Tris-Acetate buffer at a concentration of 10 mg/ml and freeze in aliquots.

G. On day three, remove an aliquot of membranes and thaw on ice. Dilute the suspension into 10 ml Tris-Acetate buffer and centrifuge at 40,000×g for 30 minutes. Repeat the wash step twice more for a total of 3 washes. Resuspend the final pellet at a concentration of 1 mg/ml in glycine-free Tris-Acetate buffer.

The binding test was performed in eppendorf tubes containing 150 µg of membrane protein and 50 nM [$^3$H]glycine in a volume of 0.5 ml. Non-specific binding was determined with 1 mM glycine. Drugs were dissolved in assay buffer (50 mM Tris-acetate, pH 7.4) or DMSO (final concentration of 0.1%). Membranes were incubated on ice for 30 minutes and bound radioligand was separated from free radioligand by filtration on Whatman GF/B glass fiber filters or by centrifugation (18,000×g, 20 min). Filters or pellet was washed three times quickly with ice-cold 5 mM Tris-acetate buffer. Filters were dried and placed in scintillation tubes and counted. Pellets were dissolved in deoxycholate/NaOH (0.1 N) solution overnight, neutralized and radioactivity was determined by scintillation counting.

A second binding test for the NMDA-glycine site used [$^3$H]dichlorokynurenic acid (DCKA) and membranes prepared as above. See, Yoneda et al., *J. Neurochem.*, 60,634–645 (1993). The binding assay was performed as described for [$^3$H]glycine above except that [$^3$H]DCKA was used to label the glycine site. The final concentration of [$^3$H]DCKA was 10 nM, and the assay was performed for 10 minutes on ice.

A third binding test used for the NMDA-glycine site used indirect assessment of affinity of ligands for the site by measuring the binding of [$^3$H]MK-801 (dizocilpine). See, Palmer and Burns, *J. Neurochem.*, 62, 187–196 (1994). Preparation of membranes for the test was the same as above. The binding assay allowed separate detection of antagonists and agonists.

The third binding test was operated to identify antagonists as follows: 100 µg of membranes were added to wells of a 96-well plate, along with glutamate (10 µM) and glycine (200 nM) and various concentrations of the ligand to be tested. The assay was started by the addition of 5 nM [3H]MK-801 (23.9 Ci/mmol), which binds to the ion channel associated with NMDA receptors. The final volume of the assay was 200 µl. The assay was performed for 1 hour at room temperature. Bound radioactivity was separated from free by filtration, using a TOMTEC harvester. Antagonist activity was indicated by decreasing radioactivity associated with the NMDA receptor with increasing concentration of the tested ligand.

The third binding test was operated to identify agonists by performing the test as above, except that the concentration of glycine was 200 nM. Agonist activity was indicated by increasing radioactivity associated with the NMDA receptor with increasing concentration of the tested ligand.

EXAMPLE 17

Assay of Calcium Flux

This example illustrates a protocol for measuring calcium flux in primary neuronal calls.

The calcium flux measurement is performed in primary neuronal cell cultures, which are prepared from rat fetal cortices dissected from pregnant rats using standard procedures and techniques that require sterile dissecting equipment, a microscope and defined medium. The protocol used was adapted from Lu et al., *Proc. Natl. Acad. Sci. USA*, 88, 6289–6292 (1991).

Defined medium is prepared in advance in accordance with the following recipe:

| Components | Source (catalogue #) | Final Concentration |
|---|---|---|
| D-glucose | Sigma (G-7021) | 0.6% |
| transferrin | Sigma (T-2252) | 100 µg/ml |

| Components | Source (catalogue #) | Final Concentration |
|---|---|---|
| insulin | Sigma (I-5500) | 25 µg/ml |
| progesterone | Sigma (P-6149) | 20 nM |
| putrescine | Sigma (P-7505) | 60 µM |
| selenium | Sigma (S-5261) | 30 nM |
| pen-strep▲ | GIBCO (15070-014) | 0.5 U-0.5 µg/ml |
| L-glutamine★ | GIBCO (25030-016) | 146 mg/l |
| MEM° | GIBCO (11095 or 11090) | 500 ml/l |
| F-12 | GIBCO (11765) | 500 ml/l |

▲pen-strep: 5,000 U/ml penicillin and 5,000 µg/ml steptomycin
★add only when MEM without L-glutamine is used
°with L-glutamine or without L-glutamine, respectively Before starting the dissection, tissue culture plates were treated with polylysine (100 µg/ml for at least 30 minutes at 37° C.) and washed with distilled water. Also, a metal tray containing two sets of sterile crude dissecting equipment (scissors and tweezers) and several sets of finer dissecting tools was autoclaved. A pair of scissors and tweezers were placed into a sterile beaker with 70% alcohol and brought to the dissecting table. A petri dish with cold phosphate buffered saline (PBS) was placed on ice next to the place of dissection.

A pregnant rat (E15 or 16 on arrival from Hilltop Lab Animals (Scottdale, Pa.), E17 or 18 at dissection) was placed in a $CO_2$/dry ice chamber until it was unconscious. The rat was removed, pinned to a backing, the area of dissection was swabbed with 70% alcohol, and skin was cut and removed from the area of interest. A second pair of scissors was used to cut through and remove the prenatal pups in their sacs. The string of sacs was placed into the cold PBS and transported to a sterile hood.

The prenatal pups were removed from the sacs and decapitated. The skulls were then removed and the brains were carefully dislodged and placed into a clean petri dish with cold PBS. At this point, it was necessary to proceed with a dissecting microscope. The brain was turned so that the cortices were contacting the plate and the tissue between the dissector and the cortex (striatum and other brain parts) was scooped out. The hippocampus and olfactory bulb were cut away from the cortex. Then the tissue was turned over and the meninges were removed with tweezers. The remaining tissue (cortex) was placed in a small petri dish with defined media.

The tissue was chopped with a scalpel and then triturated with a glass pipet that had been fire polished. The chopped, triturated tissue was then transferred to a sterile plastic tube and continued to be triturated with a glass pipet with a finer opening. Cells were counted in a suitable counting chamber. Cells were plated at roughly 40,000 cells/well in 100 µl of defined medium for 96-well plates, 200,000 cells/well in 500 µl in 24-well plates, 400,000 cells/well in 1 ml in 12-well plates, $1.5 \times 10^8$ cells/35 mm dish in 1.5 µl and $10 \times 10^8$ cells/100 mm dish in 10 ml. To inhibit glia growth, cultures were treated with 100 µM 5-flouro-2-deoxyuridine (FDUR, Sigma (F-0503)) or 50/µM uridine (Sigma (U-3003)) and 50 µM FDUR.

The cortical cultures for the standard calcium flux assay were grown in 24-well plates in the defined medium described above for 7 days and fed once with serum coining media (10% heat inactivated fetal calf serum, 0.6% glucose in MEM) by exchanging half of the medium. Cultures were used after 12 days of incubation in vitro. The cultures were rinsed three times with HCSS (i.e. HEPES-buffered control salt solution, containing 120 MM NaCl, 5.4 mM KCl, 1.8 mM $CaCl_2$ 25 mM HEPES, and 15 mM glucose, in HPLC water and adjusted to pH 7.4 by NaOH, which was also made in HPLC water). In the third wash, the culture was incubated at 37° C. for 20 to 30 minutes.

Solutions containing $^{45}Ca^{++}$ (5000 dpm/ml) and drugs for testing or controls were prepared in HCSS. Immediately before the above $^{45}Ca^{++}$ solutions were added, cultures were washed twice with HCSS, and 250 µl of $^{45}Ca^{++}$ solution per well was added, one plate at a time. The cultures were incubated for 10 minutes at room temperature, rinsed three times with HCSS, and 1 ml scintillation liquid per well was added, followed by shaking for at least 15 minutes. Retained radioactivity was counted in a scintillation counter.

EXAMPLE 18

Synthesis of N-(3-Cyano-3,3-diphenyl)propyl-2-piperidinecarboxylic Acid Methyl Ester (Compound B9)

A mixture of 0.3 g (1 mmol) of 4-bromo2,2diphenyl butyronitrile (Aldrich, Milwaukee, Wis.), 0.359 g (2 mmol) methyl pipecolinate hydrochloride (Aldrich), 0.553 g (4 mmol) potassium carbonate and 0.166 g (1 mmol) potassium iodide in 5 ml acetonitrile was refluxed under argon for 20 hours. The reaction mixture was filtered, the solvent evaporated and the residue chromatographed on silica gel column with 30% ethyl acetate in hexanes to give 0.173 g (yield 48%) of N-(3-cyano-3,3-diphenyl)propyl-2-piperidinecarboxylic acid methyl ester (compound B9) as an oil. NMR spectra of the product showed: $^1H$ NMR ($CDCl_3$, 300 MHz) 7.50–7.20 (m, 10H), 3.58 (s. 3 H), 3.10–3.00 (m, 2H), 2.70–2.50(m, 3 H), 2.50–2.35 (m, 1 H), 2.25–2.10 (m, 1 H), 1.90–1.50 (m, 4 H), 1.40–1.20 (m, 2 H); $^{13}C$ NMR ($CDCl_3$, 75 MHz) 173.59, 140.00, 139.00, 128.71, 127.72, 126.58, 126.46, 121.73, 103.85, 65.09, 52.88, 51.47, 50.92, 49.70, 36.35, 29.27, 24.82, 22.27.

EXAMPLE 19

Additional Syntheses Using Reaction 1

Additional compounds were synthesized using Reaction 1 as follows:

| Compound | Reagent | Aminoacid | Solvent | Yield |
|---|---|---|---|---|
| B1 | A | 1 | X | 70% |
| B2 | E | 1 | X | 28% |
| B3 | B | 2 | Y | 13% |
| B4 | B | 1 | X | 57% |
| B6 | C | 3 | Z | 24% |
| B7 | C | 1 | Z | 48% |
| B8 | D | 1 | X | 77% |
| B11 | D | 4 | X | 61% |
| B12 | B | 3 | X | 43% |
| B13 | B | 4 | X | 39% |
| B14 | C | 5 | Z | 63% |
| B17 | F | 1 | X | 65% |

Reagent: A) 1,1'-(4-chlorobutylidene)bis(4-fluorobenzene) (Acros Organics, Pittsburgh, Pa.); B) 4-bromo-1,1-diphenyl-1-butene [prepared as described in F. A. Ali et al., J. Med. Chem. 28: 653–660, 1985]; C) benzydryl 2-bromoethyl ether, [prepared as described in M. R. Pavia et al., J. Med. Chem. 35: 4238–4248, 1992]; D) 3,3-diphenylpropyl tosylate [prepared by $LiAlH_4$ reduction of 3,3-diphenylpropionic acid (Aldrich) to 3,3-diphenylpropanol, followed by tosylation]; E)

9-fluorenylethyl tosylate [prepared by LiAlH$_4$ reduction of 9-fluoreneacetic acid methyl ester (Aldrich) to 2-(9-fluorenyl)ethanol, followed by tosylation]; and F) 3,3-bis(4-fluorophenyl)propyl tosylate [prepared by alkylation of diethyl malonate (Aldrich) with chlorobis(4-fluorophenyl)methane (Aldrich), followed by hydrolysis and decarboxylation, LiAlH$_4$ reduction of the monocarboxylic acid, and tosylation of the formed alcohol).

Amino acid: 1) methyl pipecolinate hydrochloride (Aldrich); 2) methyl (S-(-)2-azetidinecarboxylate hydrochloride [prepared by methylation of S-(-)-2-azetidinecarboxylic acid (Aldrich) with chlorotrimethylsilane (Aldrich) in methanol according to the general procedure described in M. A. Brook et al., *Synthesis*, p. 201, 1983]; 3) L-proline methyl ester hydrochloride (Aldrich); 4) methyl (±)-trans-3-azabicyclo[3.1.0]hexane-2-carboxylate hydrochloride [prepared by methylation of (±)-trans-3-azabicyclo[3.1.0]hexane-2-carboxylic acid (Aldrich) with chlorotrimethylsilane (Aldrich) in methanol according to the general procedure described in M. A. Brook et al., *Synthesis*, 201, 1983]; 5) indole-2-carboxylic acid methyl ester hydrochloride prepared by methylation of indole-2-carboxylic acid (Aldrich) with chlorotrimethylsilane (Aldrich) in methanol according to the general procedure described in M. A. Brook et al., *Synthesis* 201, 1983].

Solvent

X) acetonitrile; Y) dioxane; Z) methanol

EXAMPLE 20A

Synthesis of N-(3,3-Diphenyl-3-hydroxy)propyl] pipecolic Acid Methyl Ester (Compound B18)

Step 1

N-[(3-Oxo-3-phenyl)propyl]pipecolic acid methyl ester: A mixture of 3.37 g (20 mmol) 3-chloropropiophenone (Aldrich), 3.59 g (20 mmol) methyl pipecolinate hydrochloride (Aldrich), 3.32 g (20 mmol) potassium iodide and 2.5 g potassium carbonate in 140 ml of acetonitrile was heated under reflux with stirring for 2h (Reaction 29, FIG. 4). The reaction mixture was filtered, the solvent evaporated and the residue dissolved in dichloromethane, washed with water and dried over sodium sulphate. Evaporation of the solvent gave N-[(3-oxo-3-phenyl)propyl]pipecolic acid methyl ester as a yellow oil which was used in the next step without further purification.

Step 2

0.21 ml of phenyllithium (1.8 M in cyclohexane-ether, Aldrich) was added dropwise into a solution of 0.101 g (0.367 mmol) of N-[(3-oxo3-phenyl)propyl]pipecolic acid methyl ester (from step 1) in 5 ml of tetrahydrofuran at −78+ C. (Reaction 30, FIG. 4). After stirring at −78° C. for 0.5 h and at 20° C. for 0.5 h, the reaction was quenched by adding 5 ml 10% ammonium chloride solution at 0° C. The mixture was extracted with methylene chloride, the solvent evaporated and the residue purified by preparative TLC with 40% ethyl acetate in hexanes to give 0.072 g (yield 56%) N-[(3, 3-diphenyl-3-hydroxy)propyl]pipecolic acid methyl ester (compound B 18) as a pale yellow oil.

EXAMPLE 20B

N-[3-(4-Chlorophenyl)-3-(4-fluorophenyl)3-hydroxypropyl]pipecolic Acid Methyl Ester (Compound B30)

Step 1

N-[3-(4-Fluorophenyl)-3-oxopropyl]pipecolic acid methyl ester was prepared in 92% yield by alkylation of methyl pipecolinate with 3chloro-4'-fluoropropiophenone (Aldrich) as described in Example 20A (Step 1).

Step 2

N-[3-(4-Chlorophenyl)-3-(4-fluorophenyl)-3-hydroxypropyl]pipecolic acid methyl ester (Compound B30): 7 ml (2 mmol) of 0.28 M solution of 4-chlorophenylmagnesium iodide in diethyl ether [prepared from 1-chloro-4-iodobenzene (Aldrich) and magnesium] was added dropwise to an ice-cooled solution of 0.605 g (2 mmol) N-[3-(4-fluorophenyl)-3-oxopropyl]pipecolic acid methyl ester (from Step 1) in 12 ml anhydrous diethyl ether with stirring under nitrogen. The mixture was stirred at room temperature for 16 hours, poured onto crushed ice and extracted with dichloromethane. The combined organic extracts were washed with brine, concentrated and the residue purified by preparative silica gel TLC with 25% ethyl acetate in hexanes to give 0.037 g (yield 4.5%) N-[3-(4-chlorophenyl)-3-(4-fluorophenyl)3-hydroxypropyl] pipecolic acid methyl ester (Compound B30).

Compound B21 was prepared in 4% yield analogously to Step 2 by reaction of N-(3-oxo-3-phenylpropyl)pipecolic acid methyl ester [synthesized analogously to Step 1 of Example 20A from ethyl pipecolinate (Aldrich)] with 4-chlorophenylmagnesium iodide.

EXAMPLE 20C

N-[3-(4-Chlorophenyl)-3-(4-fluorophenyl)prop-2-enyl]pipecolic Acid Methyl Ester (Compound B20)

A solution of 0.035 g (0.086 mmol) N-[3-(4-chlorophenyl)-3-(4 fluorophenyl)-3-hydroxypropyl] pipecolic acid methyl ester (Compound B30) in 1 ml 99% formic acid was heated under reflux for 0.5 hours. The mixture was concentrated under vacuum the residue dissolved in ethyl acetate, washed with saturated sodium bicarbonate solution and brine, and the solvent evaporated. The residue was purified by preparative silica gel TLC with 5% diethyl ether in dichlorometane to give 0.018 g (yield 54%) N-[3-(4-chlorophenyl)-3-(4-fluorophenyl)prop-2-enyl] pipecolic acid methyl ester (Compound B20)

EXAMPLE 21A

Synthesis of N-[3-Phenyl-3-(p-trifluoromethylphenoxy)propyl]pipecolic Acid Methyl Ester (Compound B16)

Step 1

0.70 ml of lithium tri-tert-butoxyaluminohydride (Aldrich) (1 M in THF) was added into a solution of 0.190 g, (0.69 mmol) N-[(3-oxo-3-phenyl)propyl]pipecolic acid methyl ester (prepared in step 1 of Example 20A) in 10 ml of THF at −78° C. (Reaction 31, FIG. 4). After stirring at −78° C. for 0.5 h and at room temperature for 20 h, the reaction was quenched by adding 10 ml 10% ammonium chloride solution at 0° C., filtered, and extracted with methylene chloride. After evaporation of the solvent, the residue was chromatographed on silica gel column with 30% ethyl acetate in hexanes to give 0.171 g (yield 89%) N-[(3-hydroxy-3-phenyl)propyl]pipecolic acid methyl ester as a pale yellow oil.

Step 2

Figure 4:
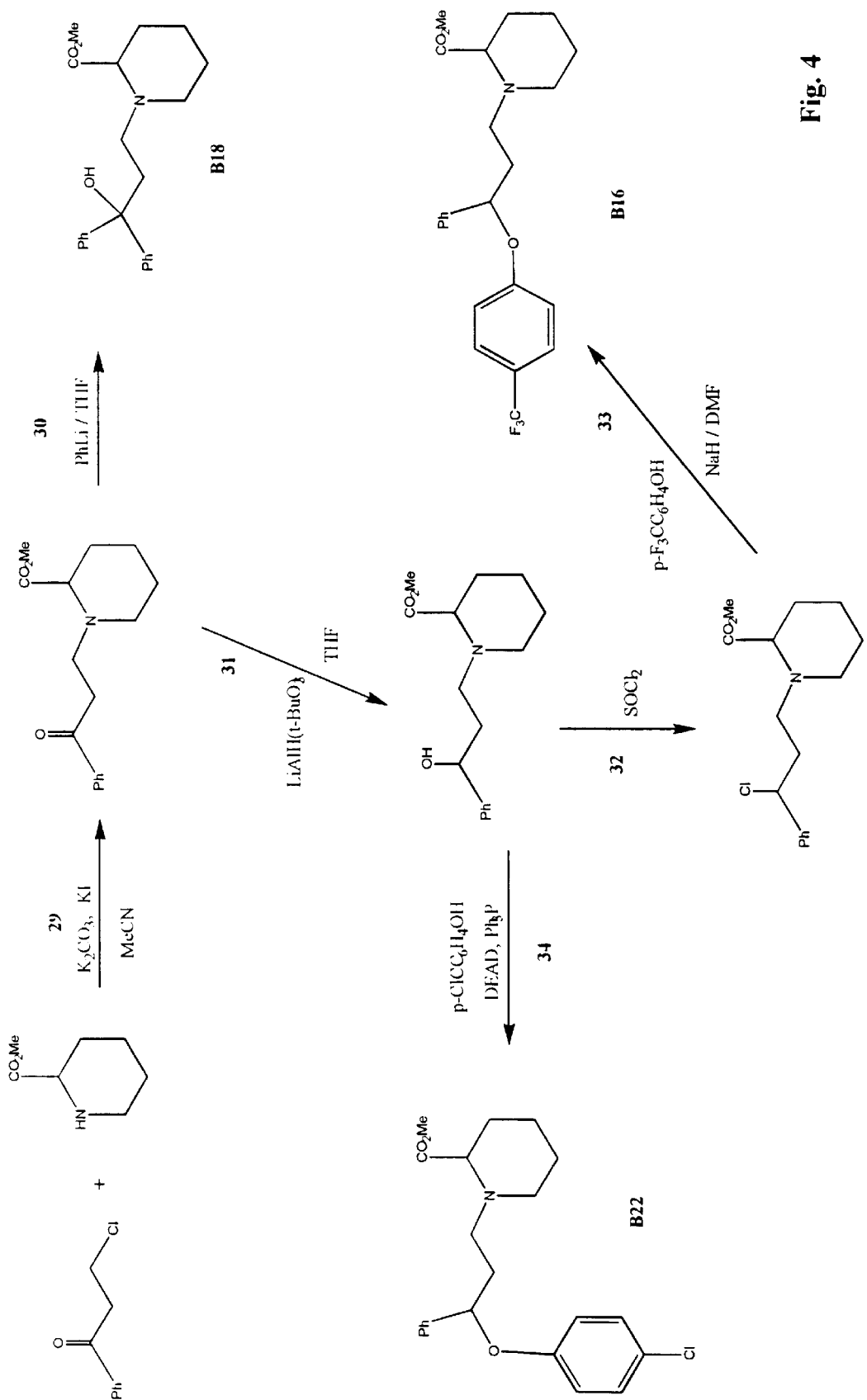
FIG. 4 shows additional representative syntheses utilized in making compounds of the invention.

To an ice cooled solution of 2.27 g (8.2 mmol) of N-[(3-hydroxy-3-phenyl)propyl]pipecolic acid methyl ester (from step 1) in 10 ml anhydrous methylene chloride was added dropwise 4 ml (51 mmol) thionyl chloride and the mixture heated under reflux for one hour (Reaction 32, FIG. 4). After addition of crushed ice, the reaction mixture was neutralized with saturated solution of potassium carbonate and extracted with methylene chloride. The combined extracts were evaporated and the residue chomatographed on silica gel column with 20% diethyl ether in hexanes to give 1.45 g (yield 60%) N-[(3-chloro-3-phenyl)propyl] pipecolic acid methyl ester as an oil.

Step 3

A solution of 0.082 g (0.28 mmol) of N-[(3-chloro-3-phenyl)propyl]pipecolic acid methyl ester (from step 2) in 1 ml of anhydrous dimethylformamide was added into a solution of sodium 4-trifluoromethylphenoxide in 2 ml anhydrous dimethylformamide at room temperature (Reaction 33, FIG. 4). The sodium 4-trifluoromethylphenoxide was generated by adding 0.040 g of 60% sodium hydride in mineral oil to a solution of 0.165 g (1 mmol) of α,α,α-trifluoro-p-cresol (Aldrich) in 2 ml of dimethylformamide. The reaction mixture was stirred at room temperature for 30 h, the solvent evaporated under vacuo and the residue purified by preparative TLC with 30% ethyl acetate in hexanes to give 0.079 g (yield 68%) N-[3-phenyl-3-(p-trifluoromethylphenoxy)propyl]pipecolic acid methyl ester (Compound B16) as a pale yellow oil.

EXAMPLE 21B

Additional Syntheses Using the Procedure of Example 21A

Compound B23 was prepared by alkylation of 4-trifluoromethylphenol (Aldrich) with N-(3-chloro-3-phenylpropyl)pipecolic acid ethyl ester as described above in Example 21A (Step 3)—yield 6.5%.

Compound B24 was prepared by alkylation of phenol (Aldrich) with N-(3-chloro-3-phenylpropyl)pipecolic acid ethyl ester as described above in Example 21A (Step 3)—yield 4%.

Compound B25 was prepared by alkylation of 4-methoxyphenol (Aldrich) with N-(3-chloro-3-phenylpropyl)pipecolic acid ethyl ester as described above in Example 21A (Step 3)—yield 8%.

Compound B29 was prepared by alkylation of thiophenol (Aldrich) with N-(3chloro-3-phenylpropyl)pipecolic acid ethyl ester as described above in Example 21A (Step 3)—yield 12%.

EXAMPLE 21C

Synthesis of N-[3-(4-chlorophenoxy)-3-phenylpropyl]pipecolic Acid Ethyl Ester (Compound B22)

0.133 g (0.76 mmol) diethyl azodicarboxylate (Aldrich) was added dropwise to a solution of 0.142 g (0.51 mmol) N-(3-hydroxy-3-phenylpropyl)pipecolic acid methyl ester (from Example 21A, Step 1), 0.083 g (0.64 mmol) p-chlorophenol (Aldrich) and 0.197 g (0.75 mmol) triphenylphosphine in 5 ml anhydrous tetrahydrofuran with stirring under nitrogen and cooling with an ice bath. The mixture was stirred at room temperature for 4 hours, the solvent evaporated and the residue purified by preparative silica gel TLC with 30% ethyl acetate in hexanes to give 0.09 g (yield 46%) N-[3-(4-chlorophenoxy)-3-phenylpropyl]pipecolic acid ethyl ester (Compound B22). (See Reaction 34, FIG. 4.)

Synthesis of N-[3-(4-chlorophenoxy)-3-phenylpropyl]pipecolic Acid Ethyl Ester (Compound B22)

0.040 g (0.11 mmol) of N-[4,4-diphenyl)but-3-enyl]-2-piperidine carboxylic acid methyl ester (compound B4) was hydrogenated over 0.030 g 10% Pd/C in 5 ml ethanol under 40 psi for 4 hours at room temperature. The mixture was separated from the catalyst by filtration through celite and the solvent evaporated to give 0.028 g (yield 70%) N-(4,4-diphenyl)butyl-2-piperidine carboxylic acid methyl ester (compound B10) as an oil. NMR spectra of the product showed: $^1$H NMR (CDCl$_3$, 300 MHz) 7.40–7.10 (m, 10 H), 3.X8 (t, 1 H), 3.65 (s, 3 H), 3.10–2.90 (n, 2 H), 2.60–2.45 (m, 1 H), 2.35–2.20 (m, 1 H), 2.10–1.90 (m, 3 H), 1.85–1.10 (m, 8 H); $^{13}$C NMR (CDCl$_3$, 75 MHz) 174.57, 145.36, 145.23, 128.66, 128.12, 128.10, 126.34, 126.33, 65.66, 56.81, 51.78, 51.44, 50.78, 33.81, 29.88, 25.53, 25.39, 22.92.

EXAMPLE 23

Synthesis of N-[4,4-Diphenyl)but-3enyl]-L-2-azetidine Carboxylic Acid Hydrochloride (Compound B15)

To a solution of 0.050 g (0.3 mmol) of N-[(4,4-diphenyl)but-3-enyl]-L-2-azetidine carboxylic acid methyl ester (compound B3) in 2.4 ml ethanol was added 1.2 ml 1N lithium hydroxide and the mixture was stirred at room temperature for 20 hours. The reaction mixture was concentrated to half volume, acidified with 4 N hydrochloric acid, and extracted 4 times with methylene chloride. The combined extracts were dried and evaporated to give 0.041 g (yield 80%) of N-[(4,4-diphenyl)but-3-enyl]-L-2-azetidine carboxylic acid hydrochloride (compound B15). $^1$H NMR (CD$_3$OD, 300 MHz) 7.50–7.00 (m, 10 H), 6.08 (t, 1 H), 4.62 (t, 1 H), 4.00–3.75 (m, 3 H), 3.30–3.20 (m, 1 H), 2.75–2.55 (m, 1 H), 2.50–2.30 (m, 3 H).

Compound B5 was prepared by hydrolysis of the corresponding ester, compound B14.

Compound B19 was prepared by hydrolysis of the corresponding ester, compound B23.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:
1. A compound of the following formula:

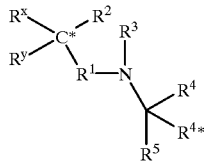

or a pharmaceutically acceptable salt thereof,
wherein:
(1) C* is a substituted carbon;
(2) $R^2$ (a) is hydrogen, (C1–C6) alkyl, (C1–C6) alkoxy, cyano, (C2–C7) alkanoyl, aminocarbonyl, (C1–C6) alkylaminocarbonyl, or dialkylaminocarbonyl wherein each alkyl is independently C1 to C6, (b) comprises (where $R^1$ is not aminoethylene, —O—$R^8$ or —S—$R^{8*}$) hydroxy, fluoro, chloro, bromo or (C2–C7) alkanoyloxy, (c) forms a double bond with an adjacent carbon or nitrogen from one of either $R^1$, $R^{xb}$ or $R^{yb}$, (d) is $R^{2a}$ linked by $R^{2b}$ to C*, or (e) is ethylene forming a third bridging structure as set forth in (2$^{iii}$)(b)(i);
(2$^i$) $R^x$ is $R^{xa}$ linked by $R^{xb}$ to C*;
(2$^{ii}$) $R^y$ is $R^{ya}$ linked by $R^{yb}$ to C*;
(2$^{iii}$) $R^{xa}$, $R^{ya}$ and $R^{2a}$, are independently Ar, which is phenyl or naphthyl, or a 5 to 7-membered non-aromatic ring having 0 heteroatoms wherein:
  (a) each of $R^{xa}$ and $R^{ya}$ can be independently substituted with one of $R^q$, $R^rO$— or $R^sS$—, wherein each of $R^q$, $R^r$ and $R^s$ are independently Ar or adamantyl, and
  (b) $R^{xa}$, $R^{ya}$, $R^{2a}$, $R^q$, $R^r$ and $R^s$ can be substituted or additionally substituted with one or more substituents selected from the group consisting of fluoro, chloro, bromo, nitro, hydroxy, cyano, trifluoromethyl, amidosulfonyl which can have up to two independent (C1–C6) N-alkyl substitutions, (C1–C12) alkyl, (C2–C12) alkenyl, amino, (C1–C6) alkylamino, dialkylamino wherein each alkyl of dialkylamino is independently C1 to C6, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be substituted for hydrogen with up to two independent (C1–C6) alkyl, (C1–C6) alkylsulfonyl, or amidino wherein the amidino can be independently substituted with up to three (C1–C6) alkyl groups, wherein:
    (i.) the substitutions of $R^{xa}$ and $R^{ya}$ can be combined to form a second bridge between $R^{xa}$ and $R^{ya}$ comprising (1) methylene or ethylene, which methylene or ethylene can be substituted by an $R^2$ when $R^2$ is ethylene to form the third bridging structure, or (2) —CH=CH— or wherein $R^{xa}$ and $R^{ya}$ can be directly linked by a single bond;
(2$^{iv}$) $R^{xb}$ and $R^{2b}$ are independently a single bond or (C1–C2) alkylene;
(2$^v$) $R^{yb}$ is a single bond, oxy, (C1–C2) alkylene, ethenylene or —CH= (where the double bond is with C*), thio, methyleneoxy or methylenethio, or either —N($R^6$)— or —CH$_2$—N($R^{6*}$)—, wherein $R^6$ and $R^{6*}$ are hydrogen or (C1–C6) alkyl;
(3) $R^1$ comprises: a straight-chained (C2–C3) aliphatic group; =N—O-(ethylene), wherein the unmatched double bond is linked to C*; —O—$R^8$ or —S—$R^{8*}$ wherein $R^8$ or $R^{8*}$ is a ethylene or ethenylene and O or S is bonded to C*; aminoethylene where the amino is bonded to C*:
  wherein $R^1$ can be substituted with up to one hydroxy, up to one (C1–C6) alkoxy or up to one (C2–C7) alkanoyloxy, with up to two independent (C1–C6) alkyl, with up to one oxo, up to one (C1–C6) alkylidene, with the proviso that the hydroxy, alkoxy, alkanoyloxy or oxo substituents are not bonded to a carbon that is bonded to a nitrogen or oxygen;
  wherein if $R^1$ contributes a heteroatom linked to C*, then $R^{yb}$ does not contribute a heteroatom linked to C*; and
  wherein the alkyl or alkylidene substituents of $R^1$ can be linked to form a 3 to 7-membered non-aromatic ring;
(4) $R^3$ (a) is hydrogen, (C1–C6) alkyl, or phenyl or phenylalkyl wherein the alkyl is C1 to C6 and the phenyl or phenyl of phenylalkyl can be substituted with the same substituents defined above for the phenyl of $R^{xa}$, (b) is —$R^{12}$C($R^{xx}$)($R^{yy}$)($R^{11}$), wherein $R^{12}$ is bonded to N, $R^{xx}$ is independently the same as $R^x$, $R^{yy}$ is independently the same as $R^y$, $R^{11}$ is independently the same as $R^2$ and $R^{12}$ is independently the same as $R^1$;
(5) $R^4$ and $R^{4*}$ are independently hydrogen or (C1–C6) alkyl, or one of $R^4$ and $R^{4*}$ can be (C1–C6) hydroxyalkyl; and
(6) $R^5$ is (CO)NR$^{13}$R$^{14}$, (CO)OR$^{15}$, (CO)SR$^{16}$, (SO$_2$)NR$^{17}$R$^{18}$, (PO)(OR$^{19}$)(OR$^{20}$), (CR$^{22}$)(OR$^{23}$)(OR$^{24}$), CN or tetrazol-5-yl, wherein (a) $R^{13}$, $R^{14}$, $R^{15}$, $R^{16}$, $R^{17}$, $R^{18}$ $R^{19}$ and $R^{20}$ are independently hydrogen, (C1–C8) alkyl which can include a (C3–C8) cycloalkyl, wherein the carbon linked to the oxygen of $R^{15}$ or the sulfur of $R^{16}$ has no more than secondary branching and, (C2–C6) hydroxyalkyl, aminoalkyl where the alkyl is C2 to C6 and the amino can be substituted with up to two independent (C1–C6) alkyls, Ar-alkyl wherein the alkyl is C1–C6, or Ar, and (b) $R^{22}$ is hydrogen or OR$^{25}$ and $R^{23}$, $R^{24}$ and $R^{25}$ are independently (C1–C6) alkyl, phenyl, benzyl or acetyl or, the alkyls of $R^{23}$ and $R^{24}$ can be combined to include 1,3-dioxolane or 1,3-dioxane:
  wherein the phenyl or naphthyl groups of $R^{13}$, $R^{14}$, $R^{15}$, $R^{16}$, $R^{17}$, $R^{18}$, $R^{19}$, $R^{20}$, $R^{22}$, $R^{23}$ or $R^{24}$ can be substituted with substituents selected from the group consisting of fluoro, chloro, bromo, nitro, cyano, hydroxy, trifluoromethyl, amidosulfonyl which can have up to two independent (C1–C6) N-alkyl substitutions, (C1–C6) alkyl, (C2–C6) alkenyl, (C1–C6) alkylamine, dialkylamine wherein each alkyl is independently C1 to C6, amino, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be N-substituted with up to two independent (C1 –C6) alkyl, (C1–C6) alkylsulfonyl, or amidino that can substituted with up to three (C1–C6) alkyl;
  wherein $R^{13}$ and $R^{14}$ together with the attached nitrogen can form a 5 to 7-membered ring;
and wherein further the following provisos apply:
  if $R^{15}$ is hydrogen and $R^1$ is propylene, then at least one of the following applies (1) both $R^{xa}$ and $R^{ya}$ are not fluorophenyl, (2) $R^y$ is Ar—(C1–C2)alkyl, Ar-oxy, Ar-methoxy, Ar-thio, Ar-methylthio, Ar—N($R^6$)— or Ar—CH$_2$—N($R^{6*}$)—, (3) $R^2$ is $R^{2a}$ $R^{2b}$—, (4) $R^2$ is not hydrogen, or (5) $R^3$ is not hydrogen;

if $R^{15}$ is hydrogen and $R^1$ is ethylene or $C*R^1$ is prop-1-enylene, then at least one of the following applies (1) an Ar of at least one of $R^{xa}$ and $R^{ya}$ is substituted with a radical different from hydrogen, (2) $R^y$ is Ar—(C1–C2)alkyl, Ar-oxy, Ar-methoxy, Ar-thio, Ar-methylthio, Ar—N($R^6$)— or Ar—CH$_2$—N($R^{6*}$)—, (3) $R^2$ is $R^{2a}$ $R^{2b}$—, (4) $R^2$ is not hydrogen, or (5) $R^3$ is not hydrogen;

if $R^5$ is C(O)NR$^{13}$R$^{14}$ wherein $R^{13}$ and $R^{14}$ are hydrogen, (C1–C8) alkyl, phenyl or substituted phenyl, then at least one of the following applies (1) an Ar of at least one of $R^x$ and $R^y$ is substituted with a radical different from hydrogen, fluoro, chloro, or bromo (2) $R^y$ is Ar—(C1–C2)alkyl, Ar-oxy, Ar-methoxy, Ar-thio, Ar-methylthio, Ar—N($R^6$)— or Ar—CH$_2$—N($R^{6*}$)—, (3) $R^2$ is $R^{2a}$ $R^{2b}$—, (4) $R^2$ is not hydrogen, (5) $R^3$ is not hydrogen, or (6) $R^1$ is not ethylene;

if $R^2$ is phenyl or p-methylphenyl, then at least one of the following applies (1) the Ar of $R^x$ and $R^y$ are not substituted with p-methylphenyl or p-methoxyphenyl, (2) an Ar of at least one of $R^x$ and $R^y$ is substituted with a radical different from hydrogen, (3) $R^y$ is Ar—(C1–C2)alkyl, Ar-oxy, Ar-methoxy, Ar-thio, Ar-methylthio, Ar—N($R^6$)— or Ar—CH2—N($R^{6*}$)—, or (4) $R^1$ is not aminoethylene, OR$^8$ or SR$^{8*}$;

if $R^2$ is p-methoxyphenyl, then at least one of the following applies (1) an Ar of at least one of $R^x$ and $R^y$ is substituted with a radical different from hydrogen, (2) $R^y$ is Ar—(C1–C2)alkyl, Ar-oxy, Ar-methoxy, Ar-thio, Ar-methylthio, Ar—N($R^6$)— or Ar—CH$_2$—N($R^{6*}$)—, or (3) $R^1$ is not OR$^8$ or —SR$^{8*}$, and the compound is not N-(1,1-diphenylpropyl)-glycinamide or N-(1,1-diphenylpropyl)-glycinamide having one or more halo substitutions on one or more of the phenyls and differs therefrom by at least two of the following: (a) substitutions or (b) differences in $R^x$, $R^y$, $R^1$, $R^3$, $R^4$, $R^{4*}$ or $R^5$.

2. The compound of claim 1, wherein (A) at least one of $R^{xa}$, $R^{ya}$ and $R^{2a}$ is substituted with fluoro, chloro, bromo, hydroxy, trifluoromethyl, trifluoromethoxy, nitro, cyano or (C3–C8) alkyl, (B) at least one of $R^{xa}$ and $R^{ya}$ is substituted with $R^q$, $R^rO$— or $R^sS$—, (B) $R^3$ is hydrogen, (C1–C6) alkyl, or phenyl or phenylalkyl wherein the alkyl is C1 to C6 and either such phenyl can be substituted with the same substituents defined above for the phenyl of $R^{xa}$ or (C) the ring structures of $R^{xa}$, $R^{ya}$ and $R^{2a}$, including substituents thereto, otherwise include at least two aromatic ring structures that together include from 15 to 20 ring atoms.

3. The compound of claim 2, wherein at least one of $R^{xa}$, $R^{ya}$ and $R^{2a}$ is substituted with fluoro, trifluoromethyl, trifluoromethoxy, nitro, cyano, or (C3–C8) alkyl.

4. The compound of claim 1, wherein at least one of $R^{xa}$ and $R^{ya}$ is substituted with $R^q$, $R^rO$—, or $R^sS$—.

5. The compound of claim 1, wherein an Ar of at least one of $R^{xa}$, $R^{ya}$ and $R^{2a}$ is phenyl.

6. The compound of claim 1, wherein $R^{yb}$ is oxy, methyleneoxy, thio, or methylenethio.

7. The compound of claim 6, wherein $R^{yb}$ is oxy or thio.

8. The compound of claim 1, wherein $R^5$ is (CO)NR$^{13}$R$^{14}$, (CO)OR$^{15}$ or (CO)SR$^{16}$.

9. The compound of claim 8, wherein $R^{15}$ is (C2–C6) alkyl, (C2–C4) hydroxyalkyl, phenyl, phenylalkyl wherein the alkyl is C1–C3, or aminoalkyl where the alkyl is C2–C6 and the amino can be substituted with up to two independent (C1–C3) alkyls, wherein the phenyl or the phenyl of phenylalkyl can be substituted.

10. The compound of claim 8, wherein $R^{15}$ is hydrogen.

11. The compound of claim 1, wherein $R^4$ is hydrogen, methyl or hydroxymethyl and $R^{4*}$ is hydrogen.

12. The compound of claim 1, wherein $R^1$ is —O—$R^8$ or —S—$R^{8*}$.

13. The compound of claim 12, wherein $R^{xa}$—$R^{xb}$—, $R^{ya}$—$R^{yb}$— and C* form:

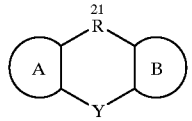

wherein A and B are Ar ring structures consistent with the definitions of $R^{xa}$ and $R^{ya}$, respectively, and Y is C* wherein $R^{21}$ either (i.) completes a single bond linking two Ar rings of $R^{xa}$ and $R^{ya}$, or (ii.) is (C1–C2) alkylene or —CH=CH—, and wherein $R^{xa}$ and $R^{ya}$ can be substituted.

14. The compound of claim 13, wherein $R^{21}$ is CH$_2$CH$_2$ or CH=CH.

15. The compound of claim 1, wherein $R^{xa}$ and $R^{ya}$ together can be substituted with up to six substituents, $R^{2a}$, $R^q$, $R^r$ and $R^s$ can each be substituted with up to 3 substituents, and wherein the presence of each of $R^q$, $R^rO$— or $R^sS$— is considered a substitution to the respective ring structure of $R^{xa}$ and $R^{ya}$.

16. The compound of claim 1, wherein a phenyl of $R^3$ is substituted with up to three substituents.

17. The compound of claim 1, wherein the Ar of $R^{13}$, $R^{14}$, $R^{15}$, $R^{16}$ $R^{17}$, $R^{18}$ $R^{19}$ or $R^{20}$ is substituted with up to three substituents.

18. The compound of claim 1, wherein the compound is an optically pure enantiomer.

19. A pharmaceutical composition comprising the compound of claim 1 and a pharmaceutically acceptable excipient.

20. The pharmaceutical composition of claim 19, wherein the compound is present in an effective amount for:
 (1) treating schizophrenia,
 (2) treating epilepsy,
 (3) treating spasticity,
 (4) treating muscle spasm,
 (5) treating pain,
 (6) treating mood disorders,
 (7) enhancing memory or learning, or
 (8) treating learning disorders.

21. The compound of claim 1 wherein:
 (1) $R^2$ is hydrogen,
 (2) $R^{xa}$ and $R^{ya}$ are both phenyl and at least one of $R^{xa}$ and $R^{ya}$ is substituted with one of phenyl, phenoxy, or phenylthio,
 (3) $R^{xb}$ is a single bond and $R^{yb}$ is a single bond or oxy, and
 (4) $R^5$ is (CO)NR$^{13}$R$^{14}$ or (CO)OR$^{15}$, wherein $R^{13}$, $R^{14}$, and $R^{15}$ are independently hydrogen; (C1–C8) alkyl which can include a (C3–C8) cycloalkyl, wherein the carbon linked to the oxygen of OR$^{15}$ has no more than secondary branching; (C2–C6) hydroxyalkyl or aminoalkyl mere the alkyl is C2 to C6 and the amino can be substituted with up to two independent (C1–C6) alkyl or phenylalkyl, wherein the alkyl is C1–C6 and the phenyl can be substituted with substituents selected from the group consisting of fluoro, chloro, bromo, nitro, cyano, hydroxy, trifluoromethyl, amidosulfonyl which can have up to two independent (C1–C6) N-alkyl substitutions, (C1–C6) alkyl, (C2–C6) alkenyl, (C1–C6) alkylamine, dialkylamine wherein each alkyl is independently C1 to C6, amino, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be N-substituted with up to two independent (C1–C6) alkyl, (C1–C6) alkylsulfonyl, amidino that can substituted with up to three (C1–C6) alkyl.

22. A method of (1) treating schizophrenia comprising administering a schizophrenia treating effective amount of a compound, (2) of treating epilepsy comprising administering an epilepsy treating effective amount of a compound, (3) treating spasticity comprising administering a spasticity treating effective amount of a compound, (4) treating muscle spasm comprising administering a muscle spasm treating effective amount of a compound, (5) treating pain comprising administering a pain treating effective amount of a compound, (6) treating mood disorders comprising administering a mood disorder treating effective amount of a compound, (7) enhancing memory or learning comprising administering a memory or learning enhancing effective amount of a compound, or (8) treating learning disorders, comprising administering an amount effective for said treating or enhancing of a compound of formula:

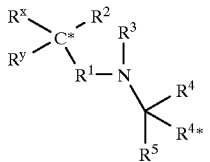

or a pharmaceutically acceptable salt thereof, wherein:
(1) $C^*$ is a substituted carbon;
(2) $R^2$ (a) is hydrogen, (C1–C6) alkyl, (C1–C6) alkoxy, cyano, (C2–C7) alkanoyl, aminocarbonyl, (C1–C6) alkylaminocarbonyl, or dialkylaminocarbonyl wherein each alkyl is independently C1 to C6, (b) comprises (where $R^1$ is not aminoethylene, —O—$R^8$ or —S—$R^{8*}$) hydroxy, fluoro, chloro, bromo or (C2–C7) alkanoyloxy, (c) forms a double bond with an adjacent carbon or nitrogen from one of either $R^1$, $R^{xb}$ or $R^{yb}$, (d) is $R^{2a}$ linked by $R^{2b}$ to $C^*$, or (e) is ethylene forming a third bridging structure as set forth in $(2^{iii})(b)(i)$;
$(2^i)$ $R^x$ is $R^{xa}$ linked by $R^{xb}$ to $C^*$;
$(2^{ii})$ $R^y$ is $R^{ya}$ linked by $R^{yb}$ to $C^*$;
$(2^{iii})$ $R^{xa}$, $R^{ya}$ and $R^{2a}$, are independently Ar, which is phenyl or naphthyl, or a 5 to 7-membered non-aromatic ring having 0 heteroatoms wherein:
  (a) each of $R^{xa}$ and $R^{ya}$ can be independently substituted with one of $R^q$, $R^rO$— or $R^sS$—, wherein each of $R^q$, $R^r$ and $R^s$ are independently Ar or adamantyl, and
  (b) $R^{xa}$, $R^{ya}$, $R^{2a}$, $R^q$, $R^r$ and $R^s$ can be substituted or additionally substituted with one or more substituents selected from the group consisting of fluoro, chloro, bromo, nitro, hydroxy, cyano, trifluoromethyl, amidosulfonyl which can have up to two independent (C1–C6) N-alkyl substitutions, (C1–C12) alkyl, (C2–C12) alkenyl, amino, (C1–C6) alkylamino, dialkylamino wherein each alkyl of dialkylamino is independently C1 to C6, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be substituted for hydrogen with up to two independent (C1–C6) alkyl, (C1–C6) alkylsulfonyl, or amidino wherein the amidino can be independently substituted with up to three (C1–C6) alkyl groups, wherein:
    (i.) the substitutions of $R^{xa}$ and $R^{ya}$ can be combined to form a second bridge between $R^{xa}$ and $R^{ya}$ comprising (1) methylene or ethylene, which methylene or ethylene can be substituted by an $R^2$ when $R^2$ is ethylene to form the third bridging structure, or (2) —CH═CH— or wherein $R^{xa}$ and $R^{ya}$ can be directly linked by a single bond;
$(2^{iv})$ $R^{xb}$ and $R^{2b}$ are independently a single bond or (C1–C2) alkylene;
$(2^v)$ $R^{yb}$ is a single bond, oxy, (C1–C2) alkylene, ethenylene or —CH═(where the double bond is with $C^*$), thio, methyleneoxy or methylenethio, or either —N($R^6$) or —CH$_2$—N($R^{6*}$)—, wherein $R^6$ and $R^{6*}$ are hydrogen or (C1–C6) alkyl;
(3) $R^1$ comprises: a straight-chained (C2–C3) aliphatic group; ═N—O—(ethylene), wherein the unmatched double bond is linked to $C^*$; —O—$R^8$or —S—$R^{8*}$ wherein $R^8$ or $R^{8*}$ is a ethylene or ethenylene and O or S is bonded to $C^*$; aminoethylene where the amino is bonded to $C^*$:
  wherein $R^1$ can be substituted with up to one hydroxy, up to one (C1–C6) alkoxy or up to one (C2–C7) alkanoyloxy, with up to two independent (C1–C6) alkyl, with up to one oxo, up to one (C1–C6) alkylidene, with the proviso that the hydroxy, alkoxy, alkanoyloxy or oxo substituents are not bonded to a carbon that is bonded to a nitrogen or oxygen;
  wherein if $R^1$ contributes a heteroatom linked to $C^*$, then $R^{yb}$ does not contribute a heteroatom linked to $C^*$; and
  wherein the alkyl or alkylidene substituents of $R^1$ can be linked to form a 3 to 7-membered non-aromatic ring;
(4) $R^3$ (a) is hydrogen, (C1–C6) alkyl, or phenyl or phenylalkyl wherein the alkyl is C1 to C6 and the phenyl or phenyl of phenylalkyl can be substituted with the same substituents defined above for the phenyl of $R^{xa}$, (b) is —$R^{12}$C($R^{xx}$)($R^{yy}$)($R^{11}$), wherein $R^{12}$ is bonded to N, $R^{xx}$ is independently the same as $R^x$, $R^{yy}$ is independently the same as $R^y$, $R^{11}$ is independently the same as $R^2$ and $R^{12}$ is independently the same as $R^1$;
(5) $R^4$ and $R^{4*}$ are independently hydrogen or (C1–C6) alkyl, or one of $R^4$ and $R^{4*}$ can be (C1–C6) hydroxyalkyl;
(6) $R^5$ is (CO)NR$^{13}$R$^{14}$, (CO)OR$^{15}$, (CO)SR$^{16}$, (SO$_2$)NR$^{17}$R$^{18}$, (PO)(OR$^{19}$)(OR$^{20}$), (CR$^{22}$)(OR$^{23}$)(OR$^{24}$), CN or tetrazol-5-yl, wherein (a) $R^{13}$, $R^{14}$, $R^{15}$, $R^{16}$, $R^{17}$, $R^{18}$ $R^{19}$ and $R^{20}$ are independently hydrogen, (C1–C8) alkyl which can include a (C3–C8) cycloalkyl, wherein the carbon linked to the oxygen of $R^{15}$ or the sulfur of $R^{16}$ has no more than secondary branching and, (C2–C6) hydroxyalkyl, aminoalkyl where the alkyl is C2 to C6 and the amino can be substituted with up to two independent (C1–C6) alkyls, Ar-alkyl wherein the alkyl is C1–C6, or Ar, and (b) $R^{22}$ is hydrogen or $OR^{25}$ and $R^{23}$, $R^{24}$ and $R^{25}$ are independently (C1–C6) alkyl, phenyl, benzyl or acetyl or, the alkyls of $R^{23}$ and $R^{24}$ can be combined to include 1,3-dioxolane or 1,3-dioxane:

wherein the phenyl or naphthyl groups of $R^{13}$, $R^{14}$, $R^{15}$, $R^{16}$, $R^{17}$, $R^{18}$, $R^{19}$, $R^{20}$, $R^{22}$, $R^{23}$ or $R^{24}$ can be substituted with substituents selected from the group consisting of fluoro, chloro, bromo, nitro, cyano, hydroxy, trifluoromethyl, amidosulfonyl which can have up to two independent (C1–C6) N-alkyl substitutions, (C1–C6) alkyl, (C2–C6) alkenyl, (C1–C6) alkylamine, dialkylamine wherein each alkyl is independently C1 to C6, amino, (C1–C6) alkoxy, (C2–C7) alkanoyl, (C2–C7) alkanoyloxy, trifluoromethoxy, hydroxycarbonyl, (C2–C7) alkyloxycarbonyl, aminocarbonyl that can be N-substituted with up to two independent (C1–C6) alkyl, (C1 –C6) alkylsulfonyl, or amidino that can substituted with up to three (C1–C6) alkyl wherein $R^{13}$ and $R^{14}$ together with the attached nitrogen can form a 5 to 7-membered ring;

and wherein further the following provisos apply:

if $R^5$ is $C(O)NR^{13}R^{14}$ wherein $R^{13}$ and $R^{14}$ are hydrogen, (C1–C8) alkyl, phenyl or substituted phenyl, then at least one of the following applies (1) an Ar of at least one of $R^x$ and $R^y$ is substituted with a radical different from hydrogen, fluoro, chloro, or bromo (2) $R^y$ is Ar—(C1–C2)alkyl, Ar-oxy, Ar-methoxy, Ar-thio, Ar-methylthio, Ar—$N(R^6)$— or Ar—$CH_2$—$N(R^{6*})$—, (3) $R^2$ is $R^{2a}$ $R^{2b}$—, (4) $R^2$ is not hydrogen (5) $R^3$ is not hydrogen, or (6) $R^1$ is not ethylene; and the compound is not N-(1,1-diphenylpropyl)-glycinamide or N-(1,1-diphenylpropyl)-glycinamide having one or more halo substitutions on one or more of the phenols and differs therefrom by at least two of the following: (a) substitutions or (b) differences in $R^x$, $R^y$, $R^1$, $R^3$, $R^4$, $R^{4*}$ or $R^5$.

23. The method of claim 22, wherein the spasticity is associated with epilepsy, stroke, head trauma, multiple sclerosis, spinal cord injury or dystonia.

24. The method of claim 22 of (1) treating schizophrenia comprising administering a schizophrenia treating effective amount of a compound, (5) treating pain comprising administering a pain treating effective amount of a compound or (6) treating mood disorders comprising administering a mood disorder treating effective amount of a compound.

25. The method of claim 22 of treating schizophrenia comprising administering a schizophrenia treating effective amount of the compound.

26. The pharmaceutical composition of claim 19, wherein the compound is present in an effective amount for treating schizophrenia.

27. The compound of claim 1, wherein $R^1$ is a straight-chained (C2–C3) aliphatic group.

28. The compound of claim 27, wherein $R^2$ forms a double bond with an adjacent carbon from $R^1$.

* * * * *